)

US011254974B2

(12) United States Patent
Deisseroth et al.

(10) Patent No.: US 11,254,974 B2
(45) Date of Patent: Feb. 22, 2022

(54) RNA FIXATION AND DETECTION IN CLARITY-BASED HYDROGEL TISSUE

(71) Applicant: The Board of Trustees of the Leland Stanford Junior University, Stanford, CA (US)

(72) Inventors: Karl A. Deisseroth, Stanford, CA (US); Emily L. Sylwestrak, Redwood City, CA (US); Priya Rajasethupathy, Stanford, CA (US); Matthew Wright, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/075,895

(22) PCT Filed: Feb. 9, 2017

(86) PCT No.: PCT/US2017/017251
§ 371 (c)(1),
(2) Date: Aug. 6, 2018

(87) PCT Pub. No.: WO2017/139501
PCT Pub. Date: Aug. 17, 2017

(65) Prior Publication Data
US 2019/0119735 A1    Apr. 25, 2019

Related U.S. Application Data

(60) Provisional application No. 62/293,490, filed on Feb. 10, 2016.

(51) Int. Cl.
| C12Q 1/6841 | (2018.01) |
| C12Q 1/6806 | (2018.01) |
| G02B 21/06 | (2006.01) |
| C12Q 1/6837 | (2018.01) |
| G01N 1/30 | (2006.01) |
| C12Q 1/68 | (2018.01) |
| G02B 21/00 | (2006.01) |

(52) U.S. Cl.
CPC ............ *C12Q 1/6841* (2013.01); *C12Q 1/68* (2013.01); *C12Q 1/6806* (2013.01); *C12Q 1/6837* (2013.01); *G01N 1/30* (2013.01); *G02B 21/06* (2013.01); *G01N 2001/305* (2013.01); *G02B 21/0024* (2013.01)

(58) Field of Classification Search
CPC ....... C12Q 1/6841; C12Q 1/6837; G01N 1/30
See application file for complete search history.

(56) References Cited

U.S. PATENT DOCUMENTS

| 3,129,158 A | 4/1964 | Raymond et al. |
| 3,208,929 A | 9/1965 | Raymond et al. |
| 3,346,479 A | 10/1967 | Natelson |
| 3,375,187 A | 3/1968 | Buchler |
| 3,563,880 A | 2/1971 | Anderson |
| 3,576,727 A | 4/1971 | Evatt |
| 3,616,454 A | 10/1971 | Levy et al. |
| 3,616,457 A | 10/1971 | Hjerten et al. |
| 3,674,678 A | 7/1972 | Post et al. |
| 3,865,712 A | 2/1975 | Davies |
| 3,989,613 A | 11/1976 | Gritzner |
| 4,088,561 A | 5/1978 | Anderson |
| 4,151,065 A | 4/1979 | Kaplan et al. |
| 4,292,161 A | 9/1981 | Hoefer et al. |
| 4,339,327 A | 7/1982 | Tyler |
| 4,375,401 A | 3/1983 | Catsimpoolas |
| 4,415,418 A | 11/1983 | Turre et al. |
| 4,479,861 A | 10/1984 | Hediger |
| 4,588,491 A | 5/1986 | Kreisher et al. |
| 4,685,025 A | 8/1987 | Carlomagno |
| 5,475,426 A | 12/1995 | Kodama |
| 6,219,575 B1 | 4/2001 | Nemati |
| 6,232,092 B1 | 5/2001 | Rogers |
| 6,472,216 B1 | 10/2002 | Chiang |
| 7,660,620 B2 | 2/2010 | Zeijlemaker et al. |
| 8,105,778 B2 | 1/2012 | Dirks et al. |
| 8,124,751 B2 * | 2/2012 | Pierce .................... C12Q 1/682 536/24.3 |
| 8,852,614 B2 | 10/2014 | Frank et al. |
| 2004/0137613 A1 | 7/2004 | Vacanti et al. |

(Continued)

FOREIGN PATENT DOCUMENTS

| CN | 103513411 A | 1/2014 |
| EP | 1438976 | 7/2004 |

(Continued)

OTHER PUBLICATIONS

Sylwestrak et al. (post art), Multiplexed Intact-Tissue Transcriptional Analysis at Cellular Resolution, 2016, cell, 164, 792-804 (Year: 2016).*
Ackerly et al. (2000) "Glutamate slows axonal transport of neurofilaments in transfected neurons" *J Cell Biol* 150(1):165-176.
Albrecht et al. (2005) "Photo- and Electropatterning of Hydrogel-Encapsulated Living Cell Arrays" *Lab Chip* 5:111-118.
Barth et al. (2004) "Alteration of neuronal firing properties after in vivo experience in a FosGFP transgenic mouse" *I Neurosci.* 24, 6466-6475.

(Continued)

*Primary Examiner* — Narayan K Bhat
(74) *Attorney, Agent, or Firm* — Edward J. Baba; Bozicevic, Field & Francis LLP

(57) ABSTRACT

Methods, kits, and systems for fixation of RNA permitting its detection in intact tissue, such as, large volume of mammalian tissue are disclosed. The methods, kits, and systems utilize carbodiimide-based chemistry to stably retain RNAs in tissue clarified using CLARITY. Also provided herein are methods, kits, and systems for detection of RNAs in clarified tissue.

19 Claims, 33 Drawing Sheets
Specification includes a Sequence Listing.

(56) References Cited

U.S. PATENT DOCUMENTS

| | | |
|---|---|---|
| 2004/0267362 A1 | 12/2004 | Hwang et al. |
| 2005/0119736 A1 | 6/2005 | Zilla et al. |
| 2005/0130317 A1 | 6/2005 | Ventzki et al. |
| 2005/0181973 A1 | 8/2005 | Genove et al. |
| 2005/0256588 A1 | 11/2005 | Sawa et al. |
| 2007/0134798 A1 | 6/2007 | McCormick et al. |
| 2008/0124374 A1 | 5/2008 | Freyman |
| 2010/0055733 A1 | 3/2010 | Lutolf et al. |
| 2012/0081518 A1 | 4/2012 | Liu et al. |
| 2012/0112069 A1 | 5/2012 | Piltch |
| 2012/0196320 A1 | 8/2012 | Seibel et al. |
| 2012/0270214 A1* | 10/2012 | Bernitz .............. C12Q 1/6841 435/6.11 |
| 2013/0065030 A1 | 3/2013 | Tallant et al. |
| 2013/0094755 A1 | 4/2013 | Lippert et al. |
| 2014/0030192 A1 | 1/2014 | Deisseroth et al. |
| 2014/0099659 A1 | 4/2014 | Keller |
| 2014/0220574 A1 | 8/2014 | Tuschl et al. |
| 2015/0087001 A1 | 3/2015 | Gradinaru et al. |
| 2015/0144490 A1 | 5/2015 | Deisseroth et al. |
| 2015/0153560 A1 | 6/2015 | Lippert et al. |
| 2015/0267251 A1 | 9/2015 | Cai et al. |
| 2016/0290899 A1 | 10/2016 | Deisseroth et al. |
| 2017/0068086 A1 | 3/2017 | Tomer et al. |
| 2017/0219465 A1 | 8/2017 | Deisseroth et al. |

FOREIGN PATENT DOCUMENTS

| | | |
|---|---|---|
| JP | 2003502649 | 1/2003 |
| WO | WO 1999036559 | 7/1999 |
| WO | WO 2000017355 | 3/2000 |
| WO | WO 2000077293 | 12/2000 |
| WO | WO 2005062938 | 7/2005 |
| WO | WO 2007030012 | 3/2007 |
| WO | WO 2009022133 | 2/2009 |
| WO | WO 2010014244 | 2/2010 |
| WO | WO 2010030358 | 3/2010 |
| WO | WO 2011111876 | 9/2011 |
| WO | WO 2012103343 | 8/2012 |
| WO | WO 2013191274 | 12/2013 |
| WO | WO 2014005866 | 1/2014 |
| WO | WO 2014025392 | 2/2014 |
| WO | WO 2014056992 | 4/2014 |
| WO | WO 2012147965 | 7/2014 |
| WO | WO 2012161143 | 7/2014 |
| WO | WO 2014182528 | 11/2014 |
| WO | WO 2015028453 | 3/2015 |
| WO | WO 2015041755 | 3/2015 |
| WO | WO 2016023009 | 2/2016 |
| WO | WO 2016073941 | 5/2016 |
| WO | WO 2016117614 | 7/2016 |
| WO | WO 2016147812 | 9/2016 |
| WO | WO 2015022883 | 3/2017 |
| WO | 2017096248 | 6/2017 |

OTHER PUBLICATIONS

Battich et al. (2013) "Image-based transcriptomics in thousands of single human cells at single-molecule resolution" Nat Meth 1-10.
Bergen et al. (2008) "Nonviral Approaches for Neuronal Delivery of Nucleic Acids" Pharm Res 25(5):983-998.
Bevis and Glick (2002) "Rapidly maturing variants of the Discosoma red fluorescent protein (DsRed)" Nature Biotechnology 20:83-87.
Bloodgood et al. (2013) "The activity-dependent transcription factor NP AS4 regulates domain-specific Inhibition" Nature 503, 121-125.
Bouard et al. (2009) "Viral vectors: from virology to transgene expression" British journal of pharmacology 157(2):153-165.
Choi et al. (2014) "Next-Generation in Situ Hybridization Chain Reaction: Higher Gain, Lower Cost Greater Durability" ACS Nano 8, 4284-4294.
Choi et al. (2010) "Programmable in situ amplification for multiplexed imaging of mRNA Expression" Nat. Biotechnol. 28, 1208-1212.
Chung et al. (2013) "Structural and molecular interrogation of intact biological systems" Nature 497, 332-337.
Ciafre et al. (2005) "Extensive modulation of a set of microRNAs in primary glioblastoma" Biochem. Biophys. Res. Commw1. 334, 1351-1358.
Davidson and Breakefield (2003) "Viral vectors for gene delivery to the central nervous system" Nat Rev Neurosci 4(5):353-364.
Denk et al. (2004) "Serial block-face scanning electron microscopy to reconstruct three-dimensional tissue nanostructure" PLoS Biol2, e329.
Dodt et al. (2007) "Ultramicroscopy: three-dimensional visualization of neuronal networks in the whole mouse brain" Nat Methods 4(4):331-336.
Egen et al. (2012) "Three-dimensional imaging of solvent-cleared organs using 3D1SCO" Nature Protocols 7, 1983-1995.
Elsabahy et al. (2011) "Non-viral nucleic acid delivery: key challenges and future directions" Curr Drug Deliv 8(3):235-244.
Ertürk et al. (2012) "Three-dimensional imaging of solvent-cleared organs using 3DISCO" Nature Protocols; 7(11):1983-1995.
Ertürk et al. (2012) "Three-Dimensional Imaging of the Unsectioned Adult Spinal Cord to Assess Axon Regeneratoin and Glial Reponses after Injury" Nature Medicine 18(1):166-171.
Esteller et al. (2011). Non-coding RI'I'As in human disease. Nat Rev Genet 12, 861-874.
Fletcher et al. (2010) "Cell mechanics and cytoskeleton" Nature 463(7280):485-492.
Garner et al. (2012) "Generation of a synthetic memory trace" Science 335, 1513-1516.
Giacca (2010) "Gene therapy" Dordrecht ; New York: Springer pp. 1-303.
Gradinaru et al. (2009) "Optical Deconstruction of Parkinsonian Neural Circuitry" Science, 324(5925):354-359.
Guenthner et al. (2013) "Permanent genetic access to transiently active neurons via TRAP: targeted recombination in active populations" Neuron 78, 773-784.
Guzowski et al. (1999) "Environment-specific expression of the immediate-early gene Arc in hippocampal neuronal ensembles" Nat Neurosci 2, 1120-1124.
Hama et al. (2011). Scale: a chemical approach for fluorescence imaging and reconstruction of transparent mouse brain. Nat Neurosci 14, 1481-1488.
Hama et al. (2015) "ScaleS: an optical clearing palette for biological imaging" Nat Neurosci 1-14.
Hern and Hubbell (1998) "Incorporation of adhesion peptides into nonadhesive hydrogels useful for tissue resurfacing" J. Biomed. Mater. Res. 39(2):266-276.
Huh and Bae (1999) "Synthesis and characterization of poly(ethylene glycol)/poly(l-lactic acid) alternating multiblock copolymers" Polymer 40(22):6147-6155.
Jäderstad et al. (2010) "Communication via gap junctions underlies early functional and beneficial interactions between grafted neural stem cells and the host" Proc Natl Acad Sci USA 107(11):5184-5189.
Ke et al. (2013) "In situ sequencing for RNA analysis in preserved tissue and cells" Nat Meih 10, 857-860.
Kuwajima et al. (2013) "ClearT: a detergent- and solvent-free clearing method for neuronal and nonneuronal Tissue" Development 140, 1364-1368.
Landgraf et al. (2007) "A mammalian microRNA expression atlas based on small RNA library sequencing". Cell 129, 1401-1414.
Lee et al. (2010) "Hydrophobic nanoparticles improve permeability of cell-encapsulating poly(ethylene glycol) hydrogels while maintaining patternability" PNAS USA 107(48):20709-20714.
Lee et al. (2014) "Highly Multiplexed Subcellular Rt\JA Sequencing in Situ" Science 343, 1360-1363.
Li et al. (2015) "Fast immmo-labeling by electrophoreticaHy driven infiltration for intact tissue imaging" Sci Rep 5, 10640.
Lin et al. (2011) "Functional identification of an aggression locus in the mouse hypothalamus" Nature 470, 221-226.
Lyford et al. (1995) "Arc, a growth factor and activity-regulated gene, encodes a novel cytoskeleton-associated protein that is enriched in neuronal dendrites" Neuron 14, 433-445.

(56) References Cited

OTHER PUBLICATIONS

Ma et al. (2005) "Potential of Nanofiber Matrix as Tissue-Engineering Scaffolds" *Tissue Eng* 11(1-2):101-109.
Masuda et al. (1999) "Analysis of chemical modification of RNA from formalin-fixed samples and optimization of molecular biology applications for such samples" Nucleic Acids.
Mattson et al. (1993) "Apractical approach to crosslinking" Mol. Biol. Rep. 17, 167-183.
Matz et al. (1999) "Fluorescent proteins from nonbioluminescent *Anthozoa* species" *Nature Biotechnology* 17: 969-973.
McLean et al. (2014) "Widespread neuron-specific transgene expression in brain and spinal cord following synapsin promoter-driven AAV9 neonatal intracerebroventricular injection" *Neurosci Lett* 576:73-78.
Nagai et al. (2002) "A variant of yellow fluorescent protein with fast and efficient maturation for cell-biological applications" *Nature Biotechnology* 20(1):87-90.
Nedivi et al. (2009). The Function of Activity-Regulated Genes in the Nervous System. Physiological Reviews 89, 1079-1103.
Nedivi et al. (1993) "Numerous candidate plasticity-related genes revealed by difierential eDNA cloning" Nature 363, 718-722.
Nguyen and Daugherty (2005) "Evolutionary optimization of fluorescent proteins for intracellular FRET" *Nature Biotechnology* 23(3):355-360.
Oh et al. (2014) "A mesoscale connectome of the mouse Brain" Nature 508, 207-214.
Oosthuysen et al. (2006) "Bioprosthetic tissue preservation by filling with a poly (acrylamide) hydrogel" *Biomaterials* 27(9):2123-2130.
Pang et al. (2009) "Oncogenic role of microRNAs in brain tumors" Acta Neuropathol. 117, 599-611.
Papadakis et al. (2004) "Promoters and control elements: designing expression cassettes for gene therapy" *Curr Gene Ther* 4(1):89-113.
Pena et al. (2009) "miRNA in situ hybridization in formaldehyde and EDC-fixed tissues". Nat Meth 6, 139-141.
Ramirez et al. (2013) "Creating a false memory in the hippocampus" Science 34L 387-391.
Reijmers et al. (2007) "Localization of a stable neural correlate of associative memory" Science 317, 1230-1233.
Renier et al. (2014) "iDISCO: a simple, rapid method to immunolabel-large tissue samples for volume Imaging". CellI59, 896-910.
Renwick et al. (2013) "Multicolor microRNA FISH effectively differentiates tumor types". J. Clin. Invest. 123, 2694-2702.
Resch-Genger et al. (2008) "Quantum dots versus organic dyes as fluorescent labels". Nat Meth 5, 763-775.
Richardson et al. (2015) Clarifying Tissue Clearing Cell 162, 246-257.
Rizzo (2004) "An improved cyan fluorescent protein variant useful for FRET" *Nature Biotechnology* 22(4) :445-449.
Seddon et al. (2004) "Membrane proteins, lipids and detergents: not just a soap opera" *Biochimica et Biophysica Acta* 1666:105-117.
Shaner et al. (2005) "A guide to choosing fluorescent proteins" *Nature Methods* 102(12):905-909.
Shen et al. (2004) "X-ray photoelectron spectroscopy and infrared spectroscopy study of maleimide-activated supports for immobilization of oligodeoxyribonudeotides". Nucleic Acids Research 32, 5973-5980.
Sheng et al. (1990) "Membrane depolarization a.nd calcium induce c-fos transcription via phosphorylation of transcription factor CREB". Neuron 4, 571-582.
Shkrob et al. (2005) "Far-red fluorescent proteins evolved from a blue chromoprotein from Actinia equine" *Biochem J.* 392(Pt 3):649-654.
Simard et al. (2001) "Urea substitutes toxic fonnamide as destabilizing agent in nucleic acid hybridizations with RNA probes" Electrophoresis 22, 2679-2683.

Smeyne et al. (1992) "Fos-lacZ transgenic mice: mapping sites of gene induction in the central nervous system" Neuron 8, 13-23.
Song et al. (2012) "Hybridization chain reaction-based aptameric system for the highly selective and sensitive detection of protein". Analyst 137, 1396-1396.
Srinivasan et al. (2002) "Effect of fixatives and tissue processing on the content and integrity of nucleic acids" The American Journal of Pathology 161, 1961-1971.
Staudt et al. (2007) "2,2'-thiodiethanol: a new water soluble mounting medium for high resolution optical Microscopy" Microsc. Res. Tech. 70, 1-9.
Susaki et al. (2014) "Whole-brain imaging with single-cell resolution using chemical cocktails and computational analysis" Cell 157, 726-739.
Tainaka et al. (2014). "Whole-body imaging with single-cell resolution by tissue decolorization" Cell 159,911-924.
Tomer and Deisseroth (2014). "Advanced CLARITY Methods for Rapid and High-Resolution Imaging of Intact Tissues." pp. 37-44.
Tomer et al. (2014) "Advanced CLARITY for rapid and high-resolution imaging of intact tissues" Nature Protocols 9, 1682-1697.
Turano (2012) "Role of Chitin in Alzheimer's disease: a new cytotoxic pathway" Dissertation submitted to University of Verona 74 pages.
Tymianski et al. (1997) "A novel use for a carbodiimide compound for the fixation of fluorescent and non-t1uorescent calcium indicators in situ following physiological experiments" Cell Calcium 21, 175-183.
Wang et al. (2004) "Evolution of new nonantibody proteins via iterative somatic hypermutation" *PNAS USA* 101(48):16745-16749.
Wanner et al. (2015). "Challenges of microtome-based serial block-face scanning electron microscopy in neuroscience" J Microsc 259, 137-142.
Wemersson et al. (2007) "Probe selection for DNA microarrays using OligoWiz" Nature Protocols 2, 2677-2691.
West and Hubbell (1999) "Polymeric Biomaterials with Degradation Sites for Proteases Involved in Cell Migration" *Macromolecules* 32(1):241-244.
Wiedenmann et al. (2002) "A far-red fluorescent protein with fast maturation and reduced oligomerization tendency from *Entacmaea quadricolor* (Anthozoa, Actinaria)" *PNAS USA* 99(18):11646-11651.
Wittmer et al. (2009) "Silk Nanofibers for Biomaterials" *Material Research Society Conference* Session WW7: Polymer Nanofibers for Medicine and Biology I.
Yang et al. (2014) "Single-cell phenotyping within transparent intact tissue through whole-body clearing" Cell 158, 945-958.
Zaber (2013) "Three-Axis Stages with Built in Controllers" Zaber Technologies Inc., pp. 1-3.
Zeisel et al. (2015) "Cell types in the mouse cortex and hippocampus revealed by single-cell RNA-seq" Science 347, 1138-1142.
Zhang et al. (2006) "Viral vectors for gene delivery in tissue engineering" *Adv Drug Deliv Rev.* 58(4):515-534.
Zhang et al. (2010) "Optogenic interrogation of neural circuits: technology for probing mammalian brain structures" *Nat Protoc* 5(3):439-456.
Zheng et al. (2005) "Molecular cloning and functional characterization of mouse chitotriosidase" Gene 29:357(1):37-46.
Zheng et al. (2015) "Simplified CLARITY for visualizing immunofluorescence labeling in the developing rat brain" Brain Struct Funct, 1-9.
Zhou et al. (2009) "Evidence for selective microRNAs and their effectors as common long-term targets for the actions of mood stabilizers" Neuropsychopharmacology 34, 1395-1405.

* cited by examiner

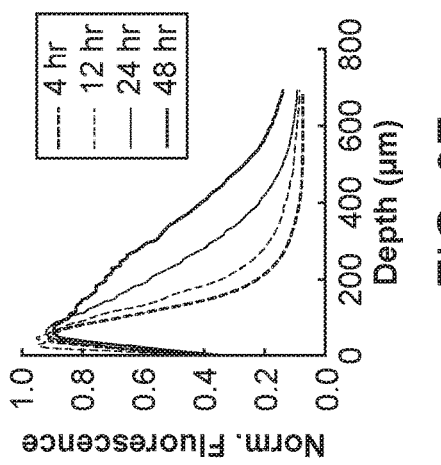
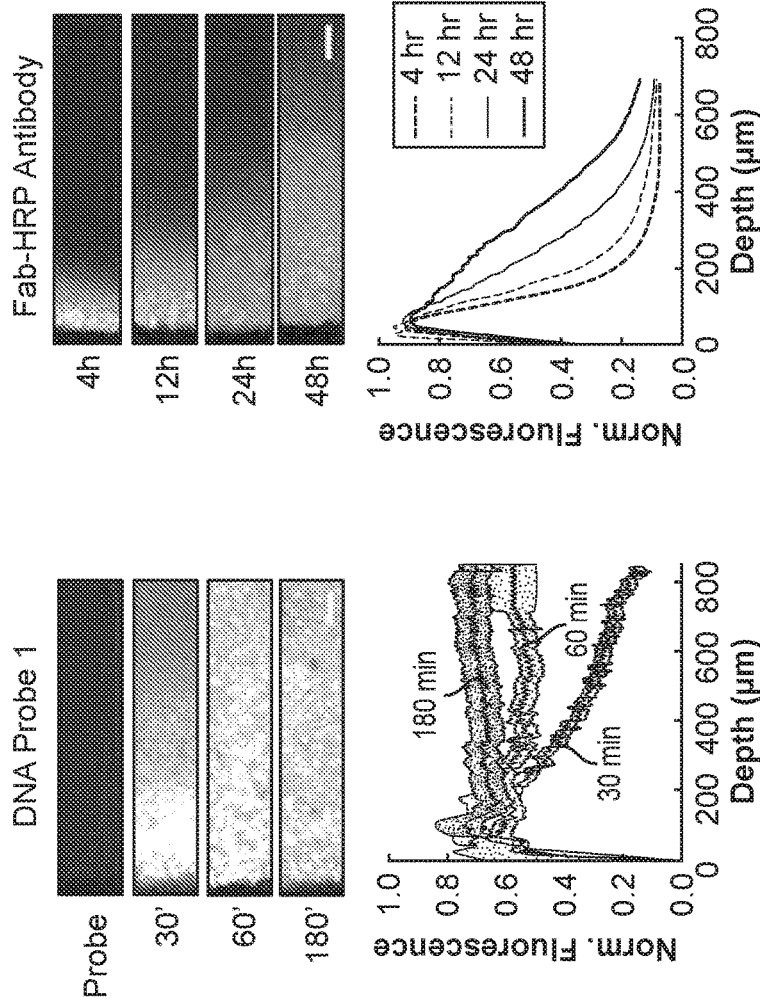
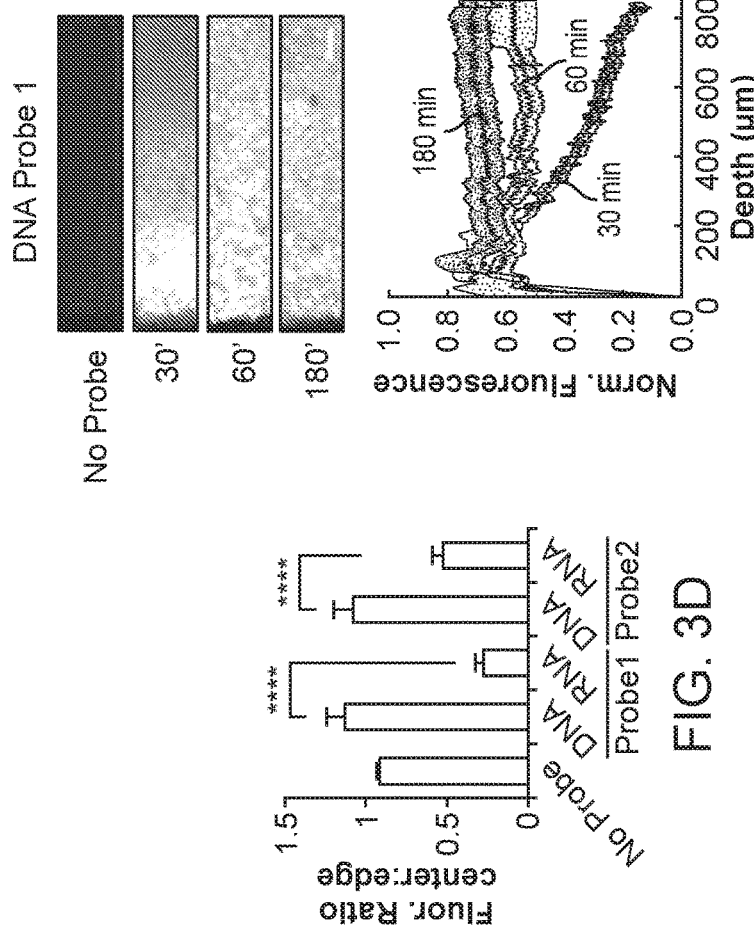

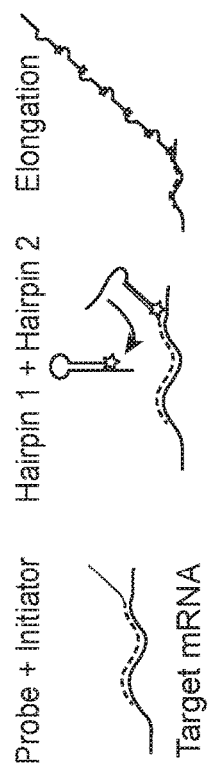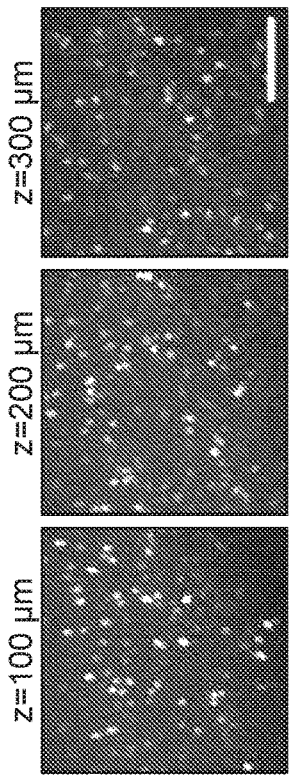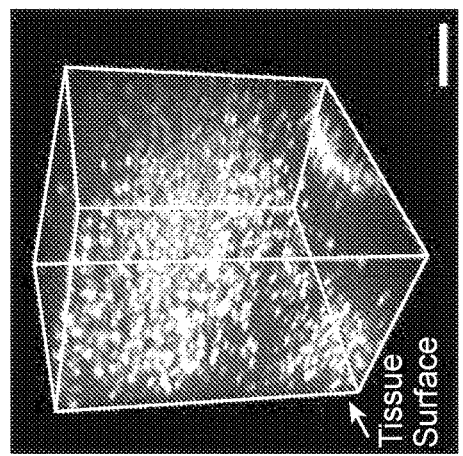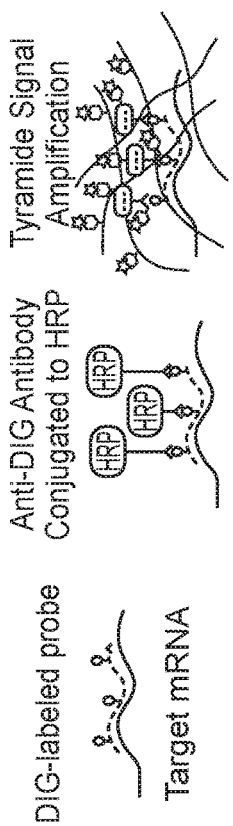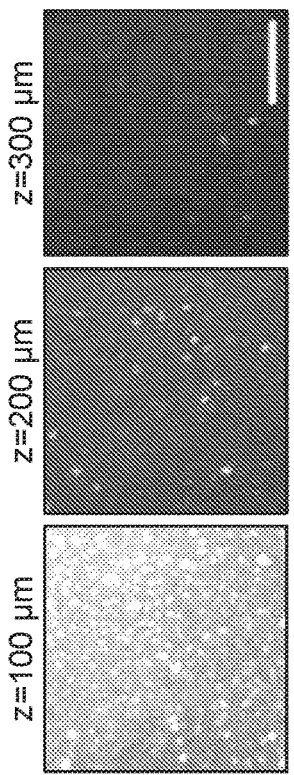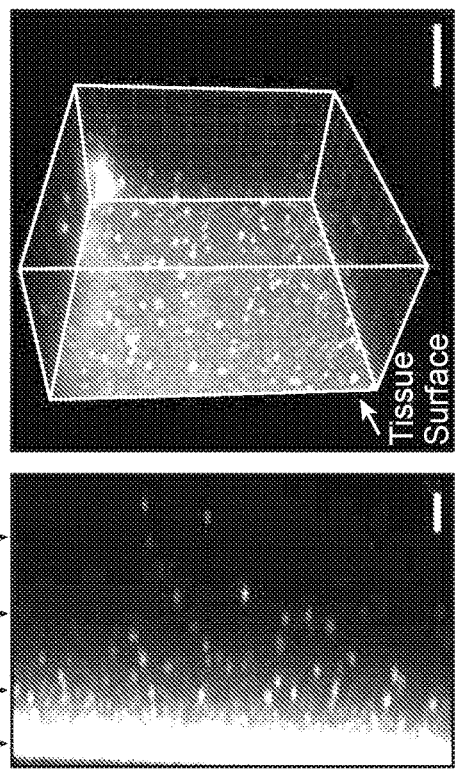
FIG. 4A  FIG. 4B  FIG. 4C  FIG. 4D

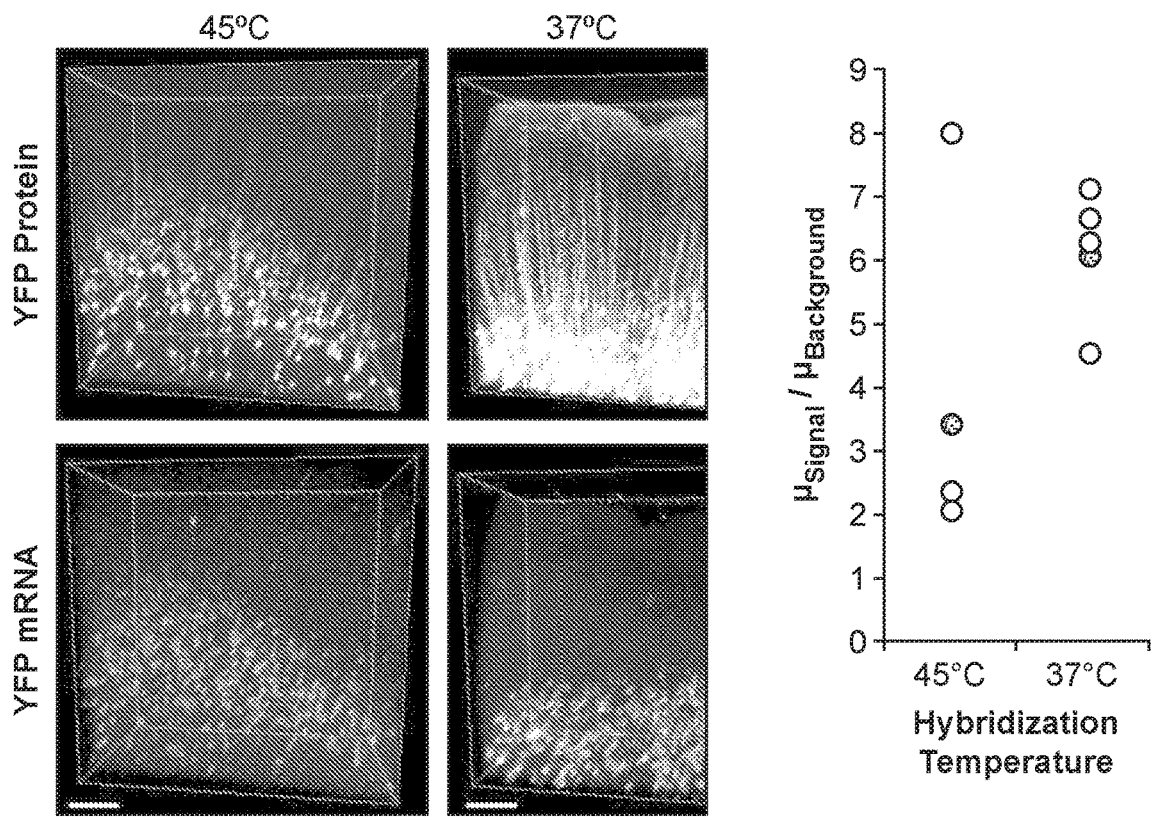
FIG. 5A
FIG. 5B
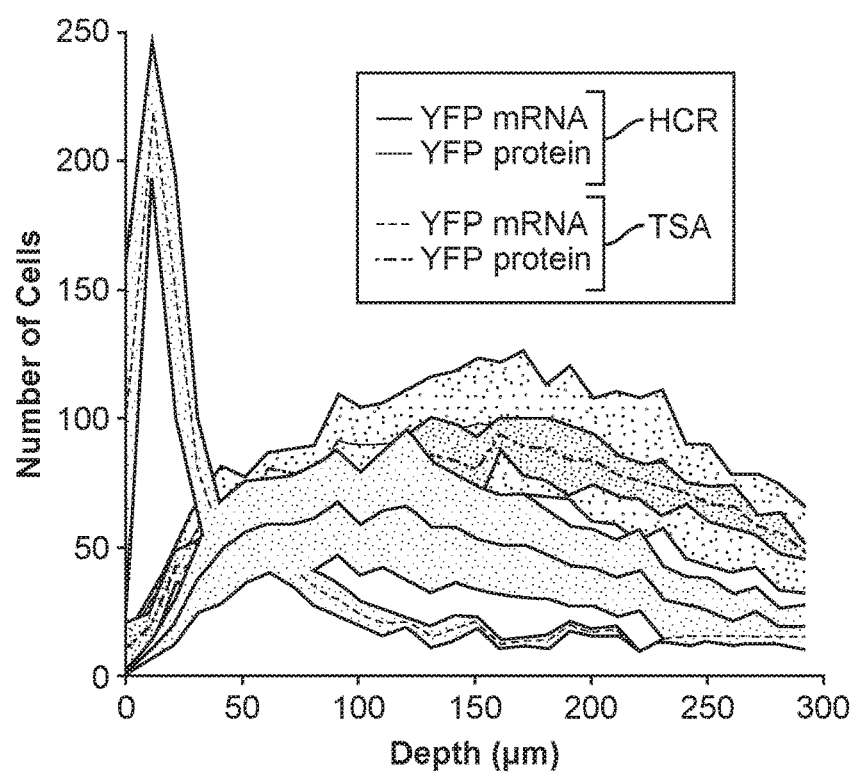
FIG. 5C

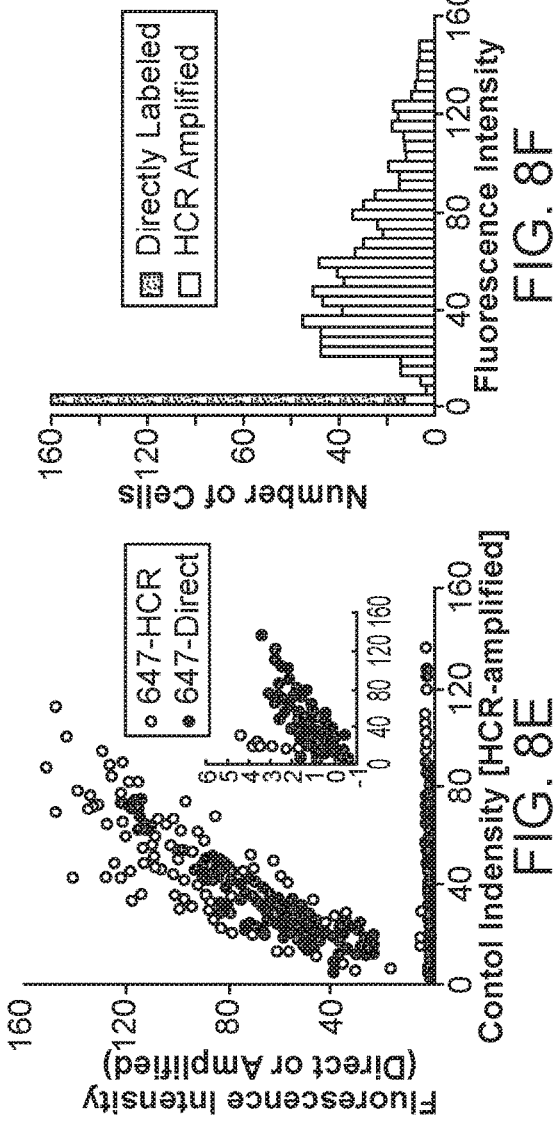
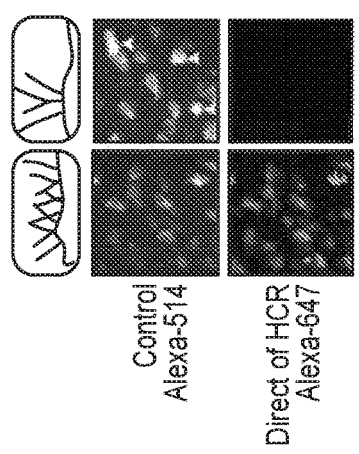
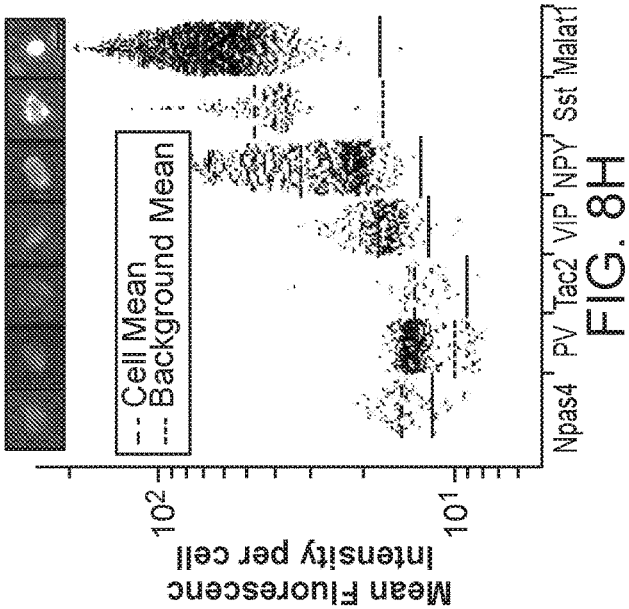
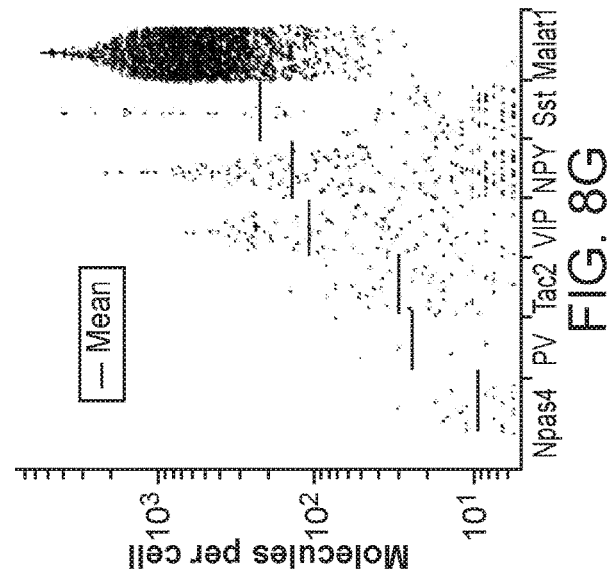

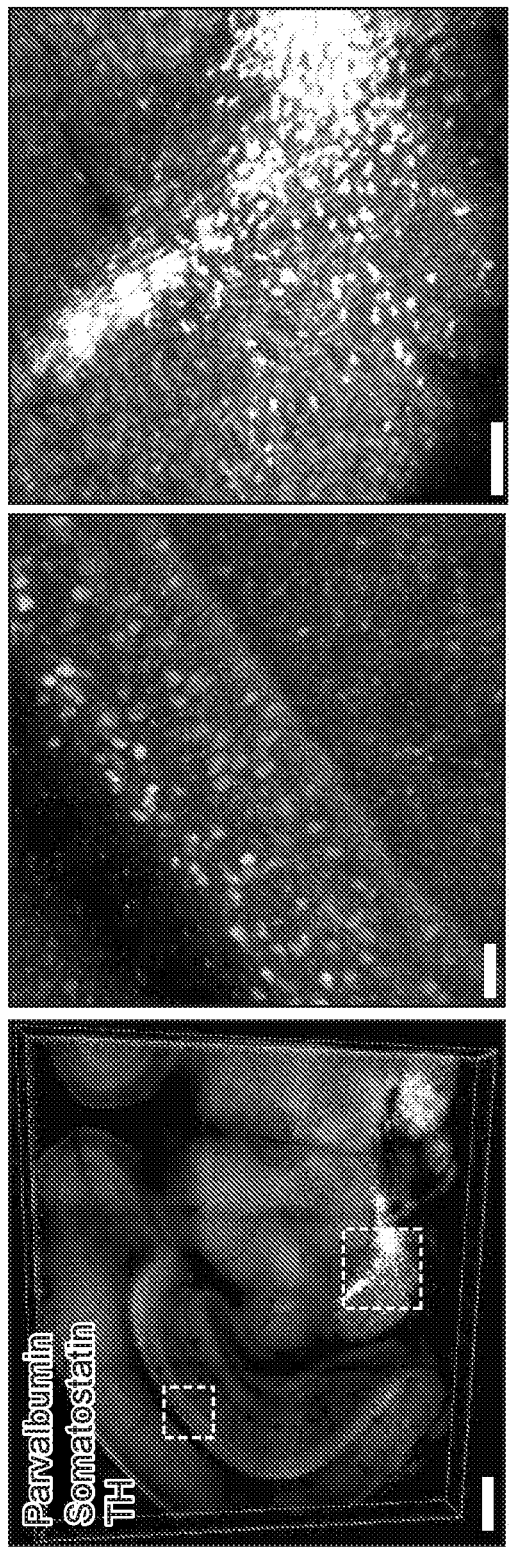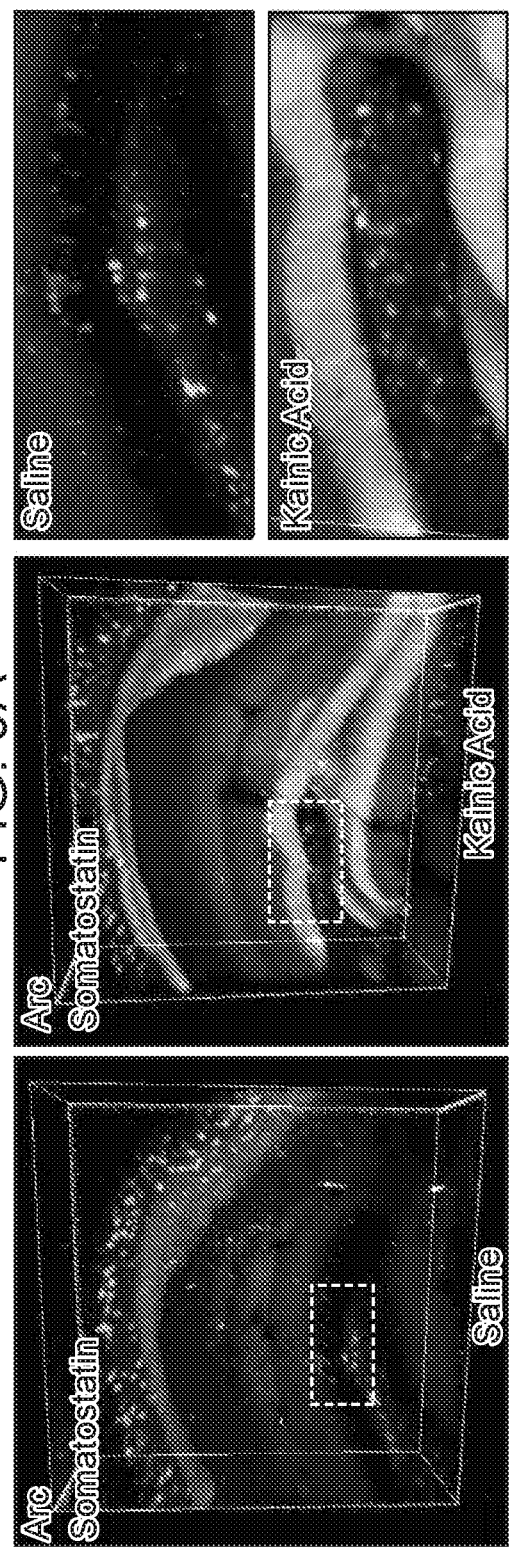
FIG. 9A
FIG. 9B

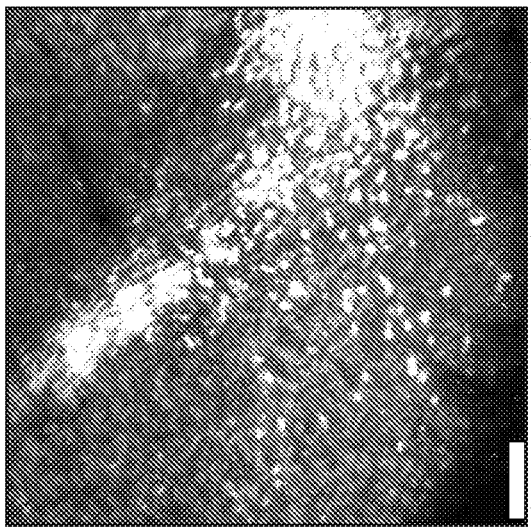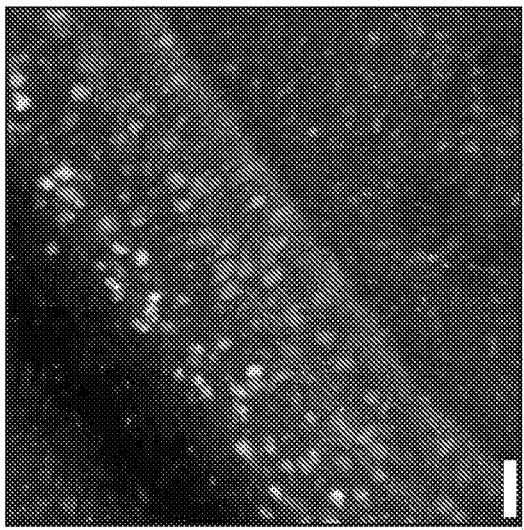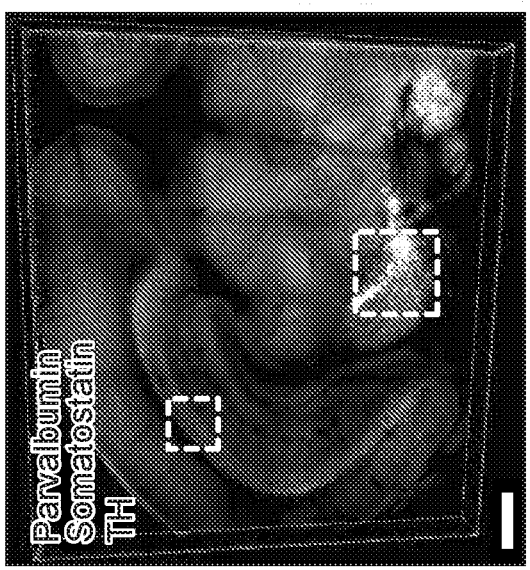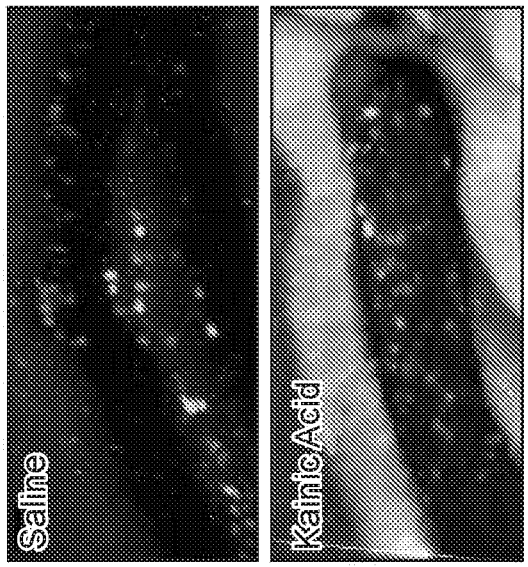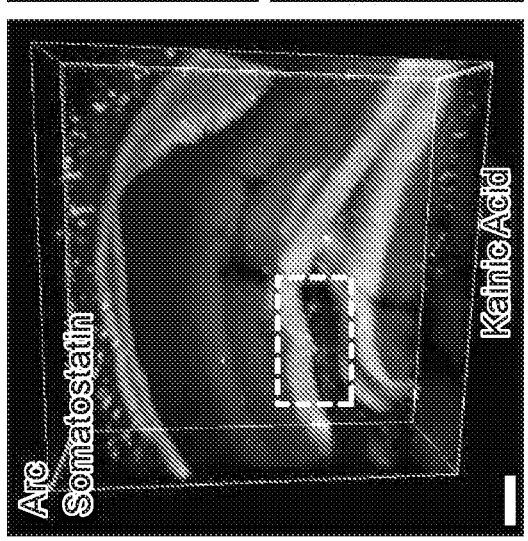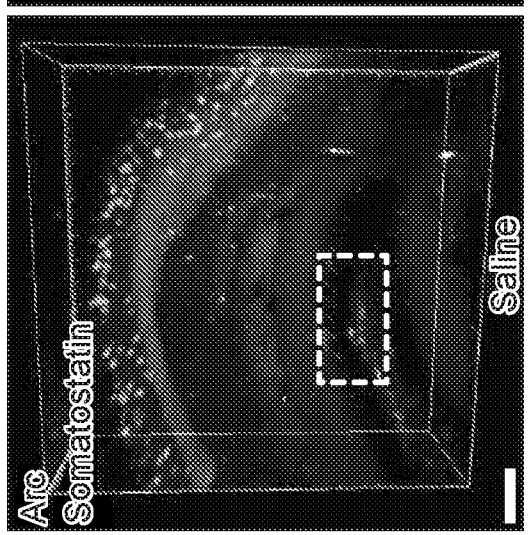
FIG. 11A
FIG. 11B

| Target | Accession # | Probe Position | Probe type | Amplification Type | Hairpin Set | [Probe] | Figure | Region | Sequences |
|---|---|---|---|---|---|---|---|---|---|
| Somatostatin | BC010770 | 380-429 | DIG-labled riboprobe | anti-DIG+TSA | - | 200ng/ul | | Cortex, Hippocampus, Striatum, pancreas, weak in stomach | gaatgtcttccagaagaagttcttgcagccagctttgcgttcccggggtg (SEQ ID NO:1) |
| | | 330-429 | DIG-labled riboprobe | anti-DIG+TSA | - | 200ng/ul | | | gaatgtcttccagaagaagttcttgcagccagctttgcgttcccggggtgccattgctgagtcgagttggcagacctctgcagctccagcctcattccg (SEQ ID NO:2) |
| | | 280-429 | DIG-labled riboprobe | anti-DIG+TSA | - | 200ng/ul | | | gaatgtcttccagaagaagttcttgcagccagctttgcgttcccggggtgccattgctgagtcgagttggcagacctctgcagctccagcctcatccgtcctgctcagtgcctcagggggcaaatctcggctcaggggcatcattctc (SEQ ID NO:3) |
| | | 265 | DIG-labeled DNA 50mer | anti-DIG+TSA | - | 50nM | 3 | | gcaaatcccggggctccagggcatcattctgtcgttggggctc (SEQ ID NO:4) |
| | | 322 | | | | | | | gttcgagttggcagacctctgcagctccagctcatctgtcctgctc (SEQ ID NO:5) |
| | | 31 | | | | | | | cagccaagctggagcgcggtgggtcagtcgagtccagtcctca (SEQ ID NO:6) |
| | | 265 | ~50mer DNA oligonucleotide | HCR | B1 | 4nM | 11 | | GAGGAGGGCAGCAAACGGAAGAGTCTTCCTTTACGATATTcaaatcctcggctccagggcatcattctgtctgttgggctcATATAGCATTCTTCTTGAGGAGGGCAGCAAACGGAAGAG (SEQ ID NO:7) |
| | | 322 | | | | | | | GAGGAGGGCAGCAAACGGAAGAGTCTTCCTTTACGATATTgttcgagttggcagacctctgcagctccagcctcatctcgtcctgctcATATAGCATTCTTCTTGAGGAGGGCAGCAAACGGAAGAG (SEQ ID NO:8) |
| | | 31 | | | | | | | GAGGAGGGCAGCAAACGGAAGAGTCTTCCTTTACGATATTcagccaagctggagcgcggtgggtcagtcgagtcctcaATATAGCATTCTTCTTGAGGAGGGCAGCAAACGGAAGAG (SEQ ID NO:9) |
| | | 430 | | | | | | | GAGGAGGGCAGCAAACGGAAGAGTCTTCCTTTACGATATTccagaagaagttcttgcagccagctttgcgttcccggggtccaATATAGCATTCTTCTTGAGGAGGGCAGCAAACGGAAGAG (SEQ ID NO:10) |

FIG. 13

| | | | | | |
|---|---|---|---|---|---|
| 265 | HCR | B2 | 4nM | 6 | CCTCGTAAATCCTCATCAATCCAGTAAACCGCC AAAAgcaaatcctcggctccagggcatcattcctgtctggttg ggctcaAAAAAGCTCAGTCCAATCCGTAAATCCTCA TCAATCATC (SEQ ID NO:11) |
| 322 | | | | | CCTCGTAAATCCTCATCAATCCAGTAAACCGCC AAAAgttcagttggcagacctctgcagctccagcctcatctcgt cctgctcaAAAAAGCTCAGTCCAATCCCTCGTAAATCCTC ATCAATCATC (SEQ ID NO:12) |
| 31 | | | | | CCTCGTAAATCCTCATCAATCCAGTAAACCGCC AAAAcagccaagctgagccggtggctcagtctagtcgcagg tcccaAAAAAGCTCAGTCCAATCCTCGTAAATCCTA TCAATCATC (SEQ ID NO:13) |
| 430 | | | | | CCTCGTAAATCCTCATCAATCCAGTAAACCGCCA AAAtccagaagaagttcttgcagccagctttgcttcccggggtg ccaAAAAAACTCAGTCCATCCTCGTAAATCCATCA ATCATC (SEQ ID NO:14) |
| 265 | HCR | B2 | 4nM | 6 | CTCACTCCCAATCTCATCTACCCTACAAATCCAATA AAAAgcaaatcctcggctccagggcatcattcctgtctgttggg gctcaATTTTCACTTCATATCACTCACTCCCAATCTCTAT CTACCC (SEQ ID NO:15) |
| 322 | | | | | CTCACTCCCAATCTCATCTACCCTACAAATCCAATA AAAAgttcgattggcagacctcgcacctccagcctcatctcgtc ctgctcATTTTCACTTCATATCACTCACTCCCAATCTCT ATCTACCC (SEQ ID NO:16) |
| 31 | | | | | CTCACTCCCAATCTCATCTACCCTACAAATCCAATA AAAAcagccaagctgagccggtggctcagtctagtcgcaggt cctcATTTTCACTTCATATCACTCACTCCCAATCTCTA TCTACCC (SEQ ID NO:17) |
| 430 | | | | | CTCACTCCCAATCTCATCTACCCTACAAATCCAATA AAAAcccagagaagttcttgcagccacctttgcttcccggggtg ccaATTTTCACTTCATATCACTCACTCCCAATCTCTAT CTACCC (SEQ ID NO:18) |
| 510 | | | | | CTCACTCCCAATCTCATCTACCCTACAAATCCAATA AAAAgtcttcaatttctaatgcaggtcaagttgagcatcgggg gccggATTTTCACTTCATATCACTCACTCCCAATCTCT ATCTACCC (SEQ ID NO:19) |
| 499 | | | | | CTCACTCCCAATCTCATCTACCCTACAAATCCAATA AAAAttcaattctctaatgcaggtcaagttgagcatcggggccca ggagttaaggaagATTTTCACTTCATATCACTCACTCCC ATCTCTATCTACCC (SEQ ID NO:20) |

FIG. 13 (Cont. 1)

| | | | | | | | |
|---|---|---|---|---|---|---|---|
| Parvalbumin | BC027424 | 14 | ~50mer DNA oligonucleotide | HCR | B1 | 0.5nM | 6,11 | Cortex, TRN, Cerebellum, weaker in hippocampus | GAGGAGGGCAGCAAACGGGAAGAGTCTTCCTTTAC GATATTtctgatgtcctcagcgctgaccacgtcgtcatcgaca tcctcaactATATAGCATTCTTTCTTGAGGAGGCAG CAAACGGGAAGAG (SEQ ID NO:21) |
| | | 72 | | | | | | | GAGGAGGGCAGCAAACGGGAAGAGTCTTCCTTTAC GATATTtgtctccagcgccagaagcgtcctttgttcttagcaga caagctctgATATAGCATTCTTTCTTGAGGAGGCAG CAAACGGGAAGAG (SEQ ID NO:22) |
| | | 210 | | | | | | | GAGGAGGGCAGCAAACGGGAAGAGTCTTCCTTTAC GATATTtgtctccagcgccagagcgtctttgttcttagcaga caagctctgATATAGCATTCTTTCTTGAGGAGGCAG CAAACGGGAAGAG (SEQ ID NO:23) |
| | | 303 | | | | | | | GAGGAGGGCAGCAAACGGGAAGAGTCTTCCTTTAC GATATTtggaggtggggaccccaagcagtcagcgccacttag cttcagccaccATATAGCATTCTTTCTTGAGGAGGCA GCAAACGGGAAGAG(SEQ ID NO:24) |
| | Tested and removed | 400 | | | | | 7 | | tacagtgtgtccgattgtacgccttatgtgttctccagcatttc c (SEQ ID NO:25) |
| | | 473 | | | | | | | agtaccaagcaggaggagatcgggcgttgtcccttgactatc tca (SEQ ID NO:26) |
| | | 683 | | | | | | | aagatgacgatccatcaccccccatctccttgtggaaagtgcag agat (SEQ ID NO:27) |
| | | 762 | | | | | | | ggactcctttgatctagctagtcctgaagactcaaccctccctc cc (SEQ ID NO28) |
| | | 550 | | | | | | | aagaagaaaaaacttgccaaccaacacccctgccaggcctg ggtcct (SEQ ID NO:29) |
| Tyrosine Hydroxylase | M69200 | 303 | ~50mer DNA oligonucleotide | HCR | B1 | 2nM | 6 | Midbrain | GAGGAGGGCAGCAAACGGGAAGAGTCTTCCTTTAC GATATTactctcgccgcctccaatgaacctgggacgtgacagc ctcggcctgtcATATAGCATTCTTTCTTGAGGAGGCAG CAAACGGGAAGAG (SEQ ID NO:30) |
| | | 817 | | | | | | | GAGGAGGGCAGCAAACGGGAAGAGTCTTCCTTTAC GATATTctgaggcctgaaccggcgttcttcttcagaagtgagacacatc ctccagctgtcATATAGCATTCTTTCTTGAGGAGGCA GCAAACGGGAAGAG (SEQ ID NO:31) |

FIG. 13 (Cont. 2)

| | | | | | | |
|---|---|---|---|---|---|---|
| 1277 | | | | | | GAGGAGGGCAGCAAACGGAAGAGTCTTCCTTTAC GATATTcatcactgaagctctctgacacgaagtacaccggctggt agtttgatctATATAGCATTCTTTCTTGAGGAGGCAG CAAACGGGAAGAG (SEQ ID NO:32) |
| 1398 | | | | | | GAGGAGGGCAGCAAACGGAAGAGTCTTCCTTTAC GATATTtctaaggagcccgatggtgtgaggactgtccagtac atcaatgccagATATAGCATTCTTTCTTGAGGAGGGC AGCAAACGGGAAGAG (SEQ ID NO:33) |
| 307 | | | | | | GAGGAGGGCAGCAAACGGAAGAGTCTTCCTTTAC GATATTccggtctctaagtgtggatttggcttcaaatgtctca aacacttttcATATAGCATTCTTTCTTGAGGAGGCAG CAAACGGGAAGAG (SEQ ID NO:34) |
| 956 | | | | | | GAGGAGGGCAGCAAACGGAAGAGTCTTCCTTTAC GATATTgcagctcgtgcagcagtctgcctcggtgagtgcatag gtgaggaggcaATAGCATTCTTTCTTGAGGAGGCA GCAAACGGGAAGAG (SEQ ID NO:35) |
| 1332 | | | | | | GAGGAGGGCAGCAAACGGAAGAGTCTTCCTTTAC GATATTtcacagagaatggccgtcgatacgaggagcatagtt cctgcttgtCATATAGCATTCTTTCTTGAGGAGGCA GCAAACGGGAAGAG (SEQ ID NO:36) |
| 387 | | | | | | GAGGAGGGCAGCAAACGGAAGAGTCTTCCTTTAC GATATTgcagccagtctgccactggcacctcgaagcgcacaaa gtactccagtgATATAGCATTCTTTCTTGAGGAGGCA GCAAACGGGAAGAG (SEQ ID NO:37) |
| 1158 | | | | | | GAGGAGGGCAGCAAACGGAAGAGTCTTCCTTTAC GATATTaggagctctccataggaagacagcccctgcaccgta agccctcagtcATAGCATTCTTTCTTGAGGAGGCA GCAAACGGGAAGAG (SEQ ID NO:38) |
| 514 | | | | | | GAGGAGGGCAGCAAACGGAAGAGTCTTCCTTTAC GATATTagggtcaaacttggtgaccagtgtgacacttatccaa ctctgacactATATAGCATTCTTTCTTGAGGAGGCAG CAAACGGGAAGAG (SEQ ID NO:39) |
| 76 | ~50mer DNA oligonucl eotide | HCR | B2 | 2nM | 11 | Midbrain |
| | | | | | | GAGGAGGGCAGCAAACGGAAGAGTCTTCCTTTAC GATATTactctgccgccgtccaatgaacttgggacgtgacagc ctcggcctgcATATAGCATTCTTTCTTGAGGAGGCAG CAAACGGGAAGAG (SEQ ID NO:40) |

FIG. 13 (Cont. 3)

| | |
|---|---|
| 817 | GAGGAGGGCACCAAACGGGAAGAGTCTTCCTTTAC<br>GATATTctggagccagtccgttccttcaagaagtgagacacatc<br>ctccagctgtcATATAGCATTCTTTCTTGAGGAGGCA<br>GCAAACGGGAAGAG (SEQ ID NO:41) |
| 1277 | GAGGAGGGCACCAAACGGGAAGAGTCTTCCTTTAC<br>GATATTcatcactgaagctctctgacacgaagtaccggctggt<br>agtttgatcATATAGCATTCTTTCTTGAGGAGGCAG<br>CAAACGGGAAGAG (SEQ ID NO:42) |
| 1398 | GAGGAGGGCACCAAACGGGAAGAGTCTTCCTTTAC<br>GATATTctaaggagccccgatgtgtgaggactgtccagtac<br>atcaatgccagATATAGCATTCTTTCTTGAGGAGGGC<br>AGCAAACGGGAAGAG (SEQ ID NO:43) |
| 307 | GAGGAGGGCACCAAACGGGAAGAGTCTTCCTTTAC<br>GATATTccggtctctcaagtgtggattttggcttcaaatgtctca<br>aacactttcATATAGCATTCTTTCTTGAGGAGGCA<br>CAAACGGGAAGAG (SEQ ID NO:44) |
| 956 | GAGGAGGGCACCAAACGGGAAGAGTCTTCCTTTAC<br>GATATTgcagctcgtgcagcagtctgctcgggtgagtgcatag<br>gtgagaggcATATAGCATTCTTTCTTGAGGAGGCA<br>GCAAACGGGAAGAG (SEQ ID NO:45) |
| 1332 | GAGGAGGGCACCAAACGGGAAGAGTCTTCCTTTAC<br>GATATTttccacagagaatgggcgctggatacgacggcatagtt<br>cctcagcttcATATAGCATTCTTTCTTGAGGAGGCA<br>GCAAACGGGAAGAG (SEQ ID NO:46) |
| 387 | GAGGAGGGCACCAAACGGGAAGAGTCTTCCTTTAC<br>GATATTgcagccaggtcgccactggcacctcgcaagcgcacaaa<br>gtactccagtgATATAGCATTCTTTCTTGAGGAGGCA<br>GCAAACGGGAAGAG (SEQ ID NO:47) |

FIG. 13 (Cont. 4)

| | | | | | | |
|---|---|---|---|---|---|---|
| | 1158 | | | | | GAGGAGGGCACCAAACGGAAGAGTCTTCCTTTAC GATATTaggagcctctccataggaagaacagccctgcacgta agccttcagctCATATAGCATTCTTCTTGAGGAGGCA (SEQ ID NO:48) |
| | 514 | | | | | GAGGAGGGCACCAAACGGAAGAGTCTTCCTTTAC GATATTaggtcaaactggtgaccagtggtgacacttatccaa ctctgacactATATAGCATTCTTCTTGAGGAGGGCAG CAAACGGGAAGAG (SEQ ID NO:49) |
| Tachykini n 1 | NM_009312 50 | ~50mer DNA oligonucl eotide | HCR | B1 | 2nM | 6 | Striatum, Cortex | GAGGAGGGCACCAAACGGAAGAGTCTTCCTTTAC GATATTatccaagaactgctaggctggtcttcgggcgattc tctccagaacaATATACCATTCTTCTTGAGGAGGCA GCAAACGGGAAGAG (SEQ ID NO:50) |
| | 441 | | | | | GAGGAGGGCACCAAACGGAAGAGTCTTCCTTTAC GATATTtagtctctcttcgtagttctgcatcgccttctttcata agccacagaATATAGCATTCTTCTTGAGGAGGCAG AAACGGGAAGAG (SEQ ID NO:51) |
| | 528 | | | | | GAGGAGGGCACCAAACGGAAGAGTCTTCCTTTAC GATATTatcattcctcataggccacattttatttaccgttcactgc tcactgacaATATAGCATTCTTCTTGAGGAGGCAG AAACGGGAAGAG (SEQ ID NO:52) |
| | 799 | | | | | GAGGAGGGCACCAAACGGAAGAGTCTTCCTTTAC GATATTccagggtacgcgaagagaccacagagtctctgc ttccagcgacATATAGCATTCTTCTTGAGGAGGCAG AGCAAACGGGAAGAG (SEQ ID NO:53) |
| | 874 | | | | | GAGGAGGGCACCAAACGGAAGAGTCTTCCTTTAC GATATTacaggaaacatgctgtaggatacaaatagagtcaaat accgaagtctcaATATAGCATTCTTCTTGAGGAGGC AGCAAACGGGAAGAG (SEQ ID NO:54) |

FIG. 13 (Cont. 5)

| Tachykni n2 | BC051476 | 253 | ~50mer DNA oligonucl eotide | HCR | B1 | 1nM | 6 | BNST, Cortex | GAGGAGGGCAGCCAAACGGAAGAGTCTTCCTTTAC GATATTgctcagcactttcagcaatcttcagagagacagggc ggctgtATATAGCATTCTTTCTTGAGGAGGCAGC ACGGGAAGAG (SEQ ID NO:55) |
|---|---|---|---|---|---|---|---|---|---|
| | | 324 | | | | | | | GAGGAGGGCAGCCAAACGGAAGAGTCTTCCTTTAC GATATTccataagtcccacaagaagtcgtgcatgtcacgtttct gtggaagtgaTATAGCATTCTTTCTTGAGGAGGCAG CAAACGGGAAGAG (SEQ ID NO:56) |
| | | 379 | | | | | | | GAGGAGGGCAGCCAAACGGAAGAGTCTTCCTTTAC GATATTgggtgtctcttcaaccacgtcgtgggagtgtgttg gctgttccATATAGCATTCTTTCTTGAGGAGGCAGCA AACGGGAAGAG (SEQ ID NO:57) |
| | | 489 | | | | | | | GAGGAGGGCAGCCAAACGGAAGAGTCTTCCTTTAC GATATTgggaggaagaggaagcaggacgactgctttta tgatcaatATATAGCATTCTTTCTTGAGGAGGCAGC AAACGGGAAGAG (SEQ ID NO:58) |
| | Tested and removed | 184 | | | | | | | GAGGAGGGCAGCCAAACGGAAGAGTCTTCCTTTAC GATATTgagccagctgatatagaatcagcagtcctactgagcctcc ctccctATATAGCATTCTTTCTTGAGGAGGCAGCAA ACGGGAAGAG (SEQ ID NO:59) |
| | | 549 | | | | | | | GAGGAGGGCAGCCAAACGGAAGAGTCTTCCTTTAC GATATTgttcattcatatcagcttctatgcagagtgggaaggagc caacagagagATATAGCATTCTTTCTTGAGGAGGCAG CAAACGGGAAGAG (SEQ ID NO:60) |
| Arc | BC023127 | 281 | ~50mer DNA oligonucl eotide | anti-DIG + TSA | - | 50nM | | | gccgttgggtcctccgtacgtgttccagccatctcagctcggcactta cc (SEQ ID NO:61) |
| | | 942 | | | | | | | Tccttcttgactccaccagttcttcaccgagccgcttgaactcc caccact (SEQ ID NO:62) |
| | | 1061 | | | | | | | cccgcttgcccagaggaactgtcgagtggttcacctgcttctg (SEQ ID NO:63) |
| | | 1284 | | | | | | | gctcgtaagacaggttgagtgcctccgtctcatcctctgtgggca gtgggtgccag (SEQ ID NO:64) |

FIG. 13 (Cont. 6)

| BC023127 | 29 | ~50mer DNA oligonucleotide | HCR | B1 | 0.5nM | 9 | GAGGAGGGCAGCAAACGGGAAGAGTCTTCCTTTACGATATTaggagcttagcagtcggcaggctcccgctgaagctagagaggcCATATAGCCATTCTTTCTTGAGGAGGCAGCAAACGGGAAGAG (SEQ ID NO:65) |
|---|---|---|---|---|---|---|---|
| | 1064 | | | | | | GAGGAGGGCAGCAAACGGGAAGAGTCTTCCTTTACGATATTacagtcccgcttgcccagagaactggtcgagtggttcaccctgctTATATAGCCATTCTTTCTTGAGGAGGCAGCAAACGGGAAGAG (SEQ ID NO:66) |
| | 395 | | | | | | GAGGAGGGCAGCAAACGGGAAGAGTCTTCCTTTACGATATTcgctgtgagtcgccggtcgggcactagccttccaagttgttctccagcttATATAGCCATTCTTTCTTGAGGAGGCAGCAAACGGGAAGAG (SEQ ID NO:67) |
| | 517 | | | | | | GAGGAGGGCAGCAAACGGGAAGAGTCTTCCTTTACGATATTccacctctccagacgtagaagacctccctccacagtgcatccacgCATATAGCCATTCTTTCTTGAGGAGGCAGCAAACGGGAAGAG (SEQ ID NO:68) |
| | 1297 | | | | | | GAGGAGGGCAGCAAACGGGAAGAGTCTTCCTTTACGATATTactcgctgtaagagcaggtgtagtgcctccgtcttcatcctctgtgggCATATAGCCATTCTTTCTTGAGGAGGCAGCAAACGGGAAGAG (SEQ ID NO:69) |
| | 281 | | | | | | GAGGAGGGCAGCAAACGGGAAGAGTCTTCCTTTACGATATTccgtggtcctccgtactgttccagcatctcagctcggcacttaccaGCATTCTTTCTTGAGGAGGCAGCAAACGGGAAGAG (SEQ ID NO:70) |
| | 942 | | | | | | GAGGAGGGCAGCAAACGGGAAGAGTCTTCCTTTACGATATTcctccttgaactccaccagttcttcaccgagccctgcttgaactccaccactATATAGCCATTCTTTCTTGAGGAGGCAGCAAACGGGAAGAG (SEQ ID NO:71) |

FIG. 13 (Cont. 7)

| | | | | | | |
|---|---|---|---|---|---|---|
| | | | | | | GAGGAGGCGCAGCAAACGGGAAGAGTCTTCCTTTAC GATATTcccgcttccgctgccgcagagcaactgtcgagtggttcaccct gcttcgATATAGCATTCTTTCTTGAGGAGGCAGCAA ACGGGAAGAG (SEQ ID NO:72) |
| | | | | | | GAGGAGGCGCAGCAAACGGGAAGAGTCTTCCTTTAC GATATTgctggtaagagcaggtgtgagtgcctccgtctcatcctct gtgggcagtggggtgccagATATAGCATTCTTTCTTGAGG AGGCGCAGCAAACGGGAAGAG (SEQ ID NO:73) |
| Npas4 | NM_15355 3 | 1154 | ~50mer DNA oligonuci eotide | HCR | B1 | 0.5nM | 9 | Activity-Induced in hippocampus superficial cortex | GAGGAGGCGCAGCAAACGGGAAGAGTCTTCCTTTAC GATATTgaatgagggtagcacacgctgggttcctaggacatagg ctgcctggATATAGCATTCTTTCTTGAGGAGGGCAGCA AAACGGGAAGAG (SEQ ID NO:74) |
| | | 1889 | | | | | GAGGAGGCGCAGCAAACGGGAAGAGTCTTCCTTTAC GATATTgctgactaggccagcagtgtacagtcccattacca gggctctaATATAGCATTCTTTCTTGAGGAGGGCAGC AAACGGGAAGAG (SEQ ID NO:75) |
| | | 1288 | | | | | GAGGAGGCGCAGCAAACGGGAAGAGTCTTCCTTTAC GATATTggagggtttgggaagcttctgtgttgaatcacacc tagttcaggagATATAGCATTCTTTCTTGAGGAGGCA GCAAACGGGAAGAG (SEQ ID NO:76) |
| | | 1569 | | | | | GAGGAGGCGCAGCAAACGGGAAGAGTCTTCCTTTAC GATATTcaactgtcctgtagtcaactgttagtggtctgggaa ggtagcactgctgggATATAGCATTCTTTCTTGAGGAGG GCAGCAAACGGGAAGAG (SEQ ID NO:77) |
| | | 1032 | | | | | GAGGAGGCGCAGCAAACGGGAAGAGTCTTCCTTTAC GATATTcagtaaaaggcctcctgaccttctgagtagtagc agtaaatccatgtccaATATAGCATTCTTTCTTGAGGAGG GCAGCAAACGGGAAGAG (SEQ ID NO:78) |

FIG. 13 (Cont. 8)

| | | | | | | |
|---|---|---|---|---|---|---|
| VIP | NM_01170 2.3 | 1798 | | | | GAGGAGGGCAGCAAACGGGAAGAGTCTTCCTTTAC GATATTctcctgggcgaagtaagtcttgctaggattgggctcag ttgctctgggaagcgATATAGCATTCTTTCTTTGAGGAGGG CAGCAAACGGAAGAG (SEQ ID NO:79) |
| | | 5 | ~50mer DNA oligonucl eotide | HCR | B1 | 1nM | 9 | Cortical and hippocampal interneurons, intestinal enteroendocrine cells | GAGGAGGGCAGCAAACGGGAAGAGTCTTCCTTTAC GATATTacactgaagatctcaggaatgccaggaactgaggctt gcttctgcttATATAGCATTCTTTCTTTGAGGAGGGCAG CAAACGGAAGAG (SEQ ID NO:80) |
| | | 158 | | | | | | | GAGGAGGGCAGCAAACGGGAAGAGTCTTCCTTTAC GATATTatttctgctaaggattctgcaagatgtcagagtctgct tttaaagagaATATAGCATTCTTTCTTTGAGGAGGGCAG CAAACGGAAGAG (SEQ ID NO:81) |
| | | 243 | | | | | | | GAGGAGGGCAGCAAACGGGAAGAGTCTTCCTTTAC GATATTagaaatctgacccagaagtctgctctaatgctgtgaa aactccatcagcatgcATATAGCATTCTTTCTTTGAGGAGG GCAGCAAACGGGAAGAG (SEQ ID NO:82) |
| | | 328 | | | | | | | GAGGAGGGCAGCAAACGGGAAGAGTCTTCCTTTAC GATATTctcactgctcctctttccattcaggatgggttcaggtatt tcttATATAGCATTCTTTCTTTGAGGAGGGCAGCAAAC GGGAAGAG (SEQ ID NO:83) |
| | | 433 | | | | | | | GAGGAGGGCAGCAAACGGGAAGAGTCTTCCTTTAC GATATTgtgtcttgattggcaacaggatctccgagatctgctgctg ctgatccgtttATATAGCATTCTTTCTTTGAGGAGGGCAG CAAACGGAAGAG (SEQ ID NO:84) |
| NPY | NM_0234 56.3 | 21 | ~50mer DNA oligonucl eotide | HCR | B1 | 1nM | 5 | Cortical and hippocampal interneurons | GAGGAGGGCAGCAAACGGGAAGAGTCTTCCTTTAC GATATTcgtcgctgagcggcgccaATATAGCATTCTTTCTTT GAGGAGGGCAGCAAACGGGAAGAG (SEQ ID NO:85) |
| | | 134 | | | | | | | GAGGAGGGCAGCAAACGGGAAGAGTCTTCCTTTAC GATATTtgagggtacccctcagccagaatgccaaacacacg agcaggatagcCATATAGCATTCTTTCTTTGAGGAGGGCAG CAAACGGAAGAG (SEQ ID NO:86) |
| | | 218 | | | | | | | GAGGAGGGCAGCAAACGGGAAGAGTCTTCCTTTAC GATATTatgagattgatgtcgcagcgggatagtactg gccatttcctCTATATAGCATTCTTTCTTTGAGGAGGGCA GCAAACGGGAAGAG (SEQ ID NO:87) |
| | | 398 | | | | | | | GAGGAGGGCAGCAAACGGGAAGAGTCTTCCTTTAC GATATTgggatgaatgaatgagatcgaggtcaggtgaaacttggaaaag tcgggacaagtATATAGCATTCTTTCTTTGAGGAGGG CAGCAACGGAAGAG (SEQ ID NO:88) |

FIG. 13 (Cont. 9)

| | | | | | | |
|---|---|---|---|---|---|---|
| Malat1 | | | | | | GAGGAGGGGCAGCAAACGGGAAGAGTCTTCCTTTAC GATATTgcggatccagtccagcctagtggtgcattggtgggac aggcagcactgttATATAGCATTCTTTCTTGAGGGAGGG CAGCAAACGGGAAGAG (SEQ ID NO:89) |
| | FJ209304.1 | 451 | ~50mer DNA oligonucleotide | HCR B1 | 2nM | 9 | Nuclear localization throughout the brain |
| | | 1461 | | | | | GAGGAGGGGCAGCAAACGGGAAGAGTCTTCCTTTAC GATATTaacgtacatgccagcgaagcgaagattttataaacggccg tcaacttaacttATATAGCATTCTTTCTTGAGGGAGG AGCAAACGGGAAGAG (SEQ ID NO:90) |
| | | 1898 | | | | | GAGGAGGGGCAGCAAACGGGAAGAGTCTTCCTTTAC GATATTggctcctccaccattcattccctctcgagcgttaaagacaa cttgccatctaccattATATAGCATTCTTTCTTGAGGAGG GCAGCAAACGGGAAGAG (SEQ ID NO:91) |
| | | 2407 | | | | | GAGGAGGGGCAGCAAACGGGAAGAGTCTTCCTTTAC GATATTacacactggtttagaagaggcgtactgtatgctgtgtt ggcaccacacctATATAGCATTCTTTCTTGAGGAGGG AGCAAACGGGAAGAG (SEQ ID NO:92) |
| | | 4598 | | | | | GAGGAGGGGCAGCAAACGGGAAGAGTCTTCCTTTAC GATATTaagtgtcttacctagatgtttaccatgtcaaattaga ccccctgacttATATAGCATTCTTTCTTGAGGAGGGG CAAACGGGAAGAG (SEQ ID NO:93) |
| | | 6231 | | | | | GAGGAGGGGCAGCAAACGGGAAGAGTCTTCCTTTAC GATATTaaccgatatgcaacgtgacctcaagatccagctactg gctgctcaaATATAGCATTCTTTCTTGAGGAGGGCAG CAAACGGGAAGAG (SEQ ID NO:94) |
| Sert | | 117 | 20mer smFISH DNA probe | HCR | 2nM per probe | 6 | dorsal raphae |
| | | | | | | | GAGGAGGGGCAGCAAACGGGAAGAGTCTTCCTTTAC GATATTcattgatatttgtcccagc (SEQ ID NO:95) |
| | | 141 | | | | | GAGGAGGGGCAGCAAACGGGAAGAGTCTTCCTTTAC GATATTtgtactgggaactgccgag (SEQ ID NO:96) |
| | | 169 | | | | | GAGGAGGGGCAGCAAACGGGAAGAGTCTTCCTTTAC GATATTgtagagtgtgcgcttcatc (SEQ ID NO:97) |
| | | 268 | | | | | GAGGAGGGGCAGCAAACGGGAAGAGTCTTCCTTTAC GATATTgcataccaatgacagacag (SEQ ID NO:98) |
| | | 299 | | | | | GAGGAGGGGCAGCAAACGGGAAGAGTCTTCCTTTAC GATATTcggaaaaccccagatgttgc (SEQ ID NO:99) |
| | | 321 | | | | | GAGGAGGGGCAGCAAACGGGAAGAGTCTTCCTTTAC GATATTcaccattctgctagcatatg (SEQ ID NO:100) |
| | | 362 | | | | | GAGGAGGGGCAGCAAACGGGAAGAGTCTTCCTTTAC GATATTaaagatgccatgatgctgt (SEQ ID NO:101) |
| | | 392 | | | | | GAGGAGGGGCAGCAAACGGGAAGAGTCTTCCTTTAC GATATTgagctccatgtagaagagtg (SEQ ID NO:102) |

FIG. 13 (Cont. 10)

| | | |
|---|---|---|
| 429 | | GAGGAGGGCAGCCAAACGGGAAGAGTCTTCCTTTAC |
| | | GATATTagaatgcacccattcgg (SEQ ID NO:103) |
| 453 | | GAGGAGGGCAGCCAAACGGGAAGAGTCTTCCTTTAC |
| | | GATATTaaatcggcagatcttctc (SEQ ID NO:104) |
| 514 | | GAGGAGGGCAGCCAAACGGGAAGAGTCTTCCTTTAC |
| | | GATATTctgttatagtagqaqcgat (SEQ ID NO:105) |
| 557 | | GAGGAGGGCAGCCAAACGGGAAGAGTCTTCCTTTAC |
| | | GATATTcgtgaagcaqaqatgaagt (SEQ ID NO:106) |
| 597 | | GAGGAGGGCAGCCAAACGGGAAGAGTCTTCCTTTAC |
| | | GATATTcgtcaagattcttccag (SEQ ID NO:107) |
| 621 | | GAGGAGGGCAGCCAAACGGGAAGAGTCTTCCTTTAC |
| | | GATATTgttcaagtagttcgtgcadttg (SEQ ID NO:108) |
| 662 | | GAGGAGGGCAGCCAAACGGGAAGAGTCTTCCTTTAC |
| | | GATATTcgaagtagtttgtgcaatgcaatg (SEQ ID NO:109) |
| 686 | | GAGGAGGGCAGCCAAACGGGAAGAGTCTTCCTTTAC |
| | | GATATTaggtgacctgcaatgcaatg (SEQ ID NO:110) |
| 710 | | GAGGAGGGCAGCCAAACGGGAAGAGTCTTCCTTTAC |
| | | GATATTatggccaagtaaaactcct (SEQ ID NO:111) |
| 766 | | GAGGAGGGCAGCCAAACGGGAAGAGTCTTCCTTTAC |
| | | GATATTctttgactcatgatcttgca (SEQ ID NO:112) |
| 796 | | GAGGAGGGCAGCCAAACGGGAAGAGTCTTCCTTTAC |
| | | GATATTatgaccatgatcagagagc (SEQ ID NO:113) |
| 818 | | GAGGAGGGCAGCCAAACGGGAAGAGTCTTCCTTTAC |
| | | GATATTtccagatgctgaagtaqt (SEQ ID NO:114) |
| 933 | | GAGGAGGGCAGCCAAACGGGAAGAGTCTTCCTTTAC |
| | | GATATTcttgccacacgttttgactc (SEQ ID NO:115) |
| 1027 | | GAGGAGGGCAGCCAAACGGGAAGAGTCTTCCTTTAC |
| | | GATATTgccagttggtttcaagtaa (SEQ ID NO:116) |
| 1063 | | GAGGAGGGCAGCCAAACGGGAAGAGTCTTCCTTTAC |
| | | GATATTctagcaaagccaggagaac (SEQ ID NO:117) |
| 1092 | | GAGGAGGGCAGCCAAACGGGAAGAGTCTTCCTTTAC |
| | | GATATTgcatctcttgtaacagtcgtt (SEQ ID NO:118) |
| 1114 | | GAGGAGGGCAGCCAAACGGGAAGAGTCTTCCTTTAC |
| | | GATATTcatgcagttcaccacactg (SEQ ID NO:119) |
| 1138 | | GAGGAGGGCAGCCAAACGGGAAGAGTCTTCCTTTAC |
| | | GATATTacaaagccagagacgaact (SEQ ID NO:120) |
| 1164 | | GAGGAGGGCAGCCAAACGGGAAGAGTCTTCCTTTAC |
| | | GATATTatgtagccaagcaccgttgaa (SEQ ID NO:121) |
| 1218 | | GAGGAGGGCAGCCAAACGGGAAGAGTCTTCCTTTAC |
| | | GATATTacacgtcttcgttcctcatc (SEQ ID NO:122) |
| | | GATATTctctccgcatatgtgatgaaa |

FIG. 13 (Cont. 11)

| | 20mer smFISH | HCR | 2nM per probe | 6 | striatum | |
|---|---|---|---|---|---|---|
| 1303 | | | | | | GAGGAGGGCAGCAAACGGGAAGAGTCTTCCTTTAC |
| 1334 | | | | | | GATATTtcgaacctgtactatccaacc (SEQ ID NO:123) |
| 1356 | | | | | | GAGGAGGGCAGCAAACGGGAAGAGTCTTCCTTTAC |
| 1386 | | | | | | GATATTcaacacacctgtgatcacac (SEQ ID NO:124) |
| 1408 | | | | | | GAGGAGGGCAGCAAACGGGAAGAGTCTTCCTTTAC |
| 1431 | | | | | | GATATTcccagatgtgaggaaactca (SEQ ID NO:125) |
| 1504 | | | | | | GAGGAGGGCAGCAAACGGGAAGAGTCTTCCTTTAC |
| 1526 | | | | | | GATATTcgatagcacaaaccattcc (SEQ ID NO:126) |
| 1548 | | | | | | GAGGAGGGCAGCAAACGGGAAGAGTCTTCCTTTAC |
| 1590 | | | | | | GATATTcccaagatgcaagtgatgac (SEQ ID NO:127) |
| 1631 | | | | | | GAGGAGGGCAGCAAACGGGAAGAGTCTTCCTTTAC |
| 1668 | | | | | | GATATTctgatgtcagtgtgaccagg (SEQ ID NO:128) |
| 1702 | | | | | | GAGGAGGGCAGCAAACGGGAAGAGTCTTCCTTTAC |
| 1724 | | | | | | GATATTcgatagacagccacgctgag (SEQ ID NO:129) |
| 1751 | | | | | | GAGGAGGGCAGCAAACGGGAAGAGTCTTCCTTTAC |
| 1780 | | | | | | GATATTgaaccaagacacgaccacgg (SEQ ID NO:130) |
| 1807 | | | | | | GAGGAGGGCAGCAAACGGGAAGAGTCTTCCTTTAC |
| 1831 | | | | | | GATATTgcagaactgatgattcca (SEQ ID NO:131) |
| 1855 | | | | | | GAGGAGGGCAGCAAACGGGAAGAGTCTTCCTTTAC |
| 19 | | | | | | GATATTaaaaccatcccgggctgaag (SEQ ID NO:132) |
| | | | | | | GAGGAGGGCAGCAAACGGGAAGAGTCTTCCTTTAC |
| | | | | | | GATATTcaggagaaacaagggctga (SEQ ID NO:133) |
| | | | | | | GAGGAGGGCAGCAAACGGGAAGAGTCTTCCTTTAC |
| | | | | | | GATATTgttggggtggactcatcaaa (SEQ ID NO:134) |
| | | | | | | GAGGAGGGCAGCAAACGGGAAGAGTCTTCCTTTAC |
| | | | | | | GATATTctccagtgggataatcgta (SEQ ID NO:135) |
| | | | | | | GAGGAGGGCAGCAAACGGGAAGAGTCTTCCTTTAC |
| | | | | | | GATATTtatgcagtagcccaagatga (SEQ ID NO:136) |
| | | | | | | GAGGAGGGCAGCAAACGGGAAGAGTCTTCCTTTAC |
| | | | | | | GATATTaggatgcagatgacacacg (SEQ ID NO:137) |
| | | | | | | GAGGAGGGCAGCAAACGGGAAGAGTCTTCCTTTAC |
| | | | | | | GATATTgtgctgatcagccgataaat (SEQ ID NO:138) |
| | | | | | | GAGGAGGGCAGCAAACGGGAAGAGTCTTCCTTTAC |
| | | | | | | GATATTataatgcctccttaadtgt (SEQ ID NO:139) |
| | | | | | | GAGGAGGGCAGCAAACGGGAAGAGTCTTCCTTTAC |
| | | | | | | GATATTgtgtttcaggagtgatact (SEQ ID NO:140) |
| | | | | | | GAGGAGGGCAGCAAACGGGAAGAGTCTTCCTTTAC |
| | | | | | | GATATTtatgtcccacacgaattc (SEQ ID NO:141) |
| | | | | | | GAGGAGGGCAGCAAACGGGAAGAGTCTTCCTTTAC |
| | | | | | | GATATTagatatcatcgtaccagga (SEQ ID NO:142) |
| Drd2 | | | | | | |

FIG. 13 (Cont. 12)

| | DNA probe | | | | | |
|---|---|---|---|---|---|---|
| 96 | | | | | | GAGGAGGGCAGCAAACGGGAAGAGTCTTCCTTTAC |
| 118 | | | | | | GATATTggcatagtagttgtactgg (SEQ ID NO:143) |
| 141 | | | | | | GAGGAGGGCAGCAAACGGGAAGAGTCTTCCTTTAC |
| 168 | | | | | | GATATTaagatagagacgtgaccag (SEQ ID NO:144) |
| 191 | | | | | | GAGGAGGGCAGCAAACGGGAAGAGTCTTCCTTTAC |
| 214 | | | | | | GATATTgcacattgccaaagaccatg (SEQ ID NO:145) |
| 238 | | | | | | GAGGAGGGCAGCAAACGGGAAGAGTCTTCCTTTAC |
| 260 | | | | | | GATATTctctctggatacagccatg (SEQ ID NO:146) |
| 292 | | | | | | GAGGAGGGCAGCAAACGGGAAGAGTCTTCCTTTAC |
| 316 | | | | | | GATATTgttggtgctggtctgcaaag (SEQ ID NO:147) |
| 338 | | | | | | GAGGAGGGCAGCAAACGGGAAGAGTCTTCCTTTAC |
| 404 | | | | | | GATATTacagcgcaggctgactatcag (SEQ ID NO:148) |
| 426 | | | | | | GAGGAGGGCAGCAAACGGGAAGAGTCTTCCTTTAC |
| 448 | | | | | | GATATTagtgtggccaccagaagatc (SEQ ID NO:149) |
| 472 | | | | | | GAGGAGGGCAGCAAACGGGAAGAGTCTTCCTTTAC |
| 496 | | | | | | GATATTatagaccgaccaggcataa (SEQ ID NO:150) |
| 520 | | | | | | GAGGAGGGCAGCAAACGGGAAGAGTCTTCCTTTAC |
| 542 | | | | | | GATATTctgctgaatttccactcacc (SEQ ID NO:151) |
| 564 | | | | | | GAGGAGGGCAGCAAACGGGAAGAGTCTTCCTTTAC |
| 587 | | | | | | GATATTgtgacaaagatgtcacagtg (SEQ ID NO:152) |
| | | | | | | GAGGAGGGCAGCAAACGGGAAGAGTCTTCCTTTAC |
| | | | | | | GATATTgtgcacatcatgacatcca (SEQ ID NO:153) |
| | | | | | | GAGGAGGGCAGCAAACGGGAAGAGTCTTCCTTTAC |
| | | | | | | GATATTcaacatagccatggccacag (SEQ ID NO:154) |
| | | | | | | GAGGAGGGCAGCAAACGGGAAGAGTCTTCCTTTAC |
| | | | | | | GATATTggagctgtagcgtgtgtta (SEQ ID NO:155) |
| | | | | | | GAGGAGGGCAGCAAACGGGAAGAGTCTTCCTTTAC |
| | | | | | | GATATTatcatgacagtaactcggcg (SEQ ID NO:156) |
| | | | | | | GAGGAGGGCAGCAAACGGGAAGAGTCTTCCTTTAC |
| | | | | | | GATATTaaggacaggaccccagacat (SEQ ID NO:157) |
| | | | | | | GAGGAGGGCAGCAAACGGGAAGAGTCTTCCTTTAC |
| | | | | | | GATATTaaggacagtgccaaagcat (SEQ ID NO:158) |
| | | | | | | GAGGAGGGCAGCAAACGGGAAGAGTCTTCCTTTAC |
| | | | | | | GATATTtctgtctgtgttgttcag (SEQ ID NO:159) |
| | | | | | | GAGGAGGGCAGCAAACGGGAAGAGTCTTCCTTTAC |
| | | | | | | GATATTagggttggcaatgatacact (SEQ ID NO:160) |
| | | | | | | GAGGAGGGCAGCAAACGGGAAGAGTCTTCCTTTAC |
| | | | | | | GATATTtggaggagtagaccaccaag (SEQ ID NO:161) |
| | | | | | | GAGGAGGGCAGCAAACGGGAAGAGTCTTCCTTTAC |
| | | | | | | GATATTgaaggcacgtagaaccgga (SEQ ID NO:162) |

FIG. 13 (Cont. 13)

| 614 | | | | | | GAGGAGGGGCAGCAAACGGGAAGAGTCTTCCTTTAC GATATTtttgatatagaccagcagg (SEQ ID NO:163) |
| --- | --- | --- | --- | --- | --- | --- |
| 636 | | | | | | GAGGAGGGGCAGCAAACGGGAAGAGTCTTCCTTTAC GATATTgcttgcgagaacgatgtag (SEQ ID NO:164) |
| 680 | | | | | | GAGGAGGGGCAGCAAACGGGAAGAGTCTTCCTTTAC GATATTctgaaagctcggctgctac (SEQ ID NO:165) |
| 702 | | | | | | GAGGAGGGGCAGCAAACGGGAAGAGTCTTCCTTTAC GATATTgagtggtgtcttcaggttg (SEQ ID NO:166) |
| 736 | | | | | | GAGGAGGGGCAGCAAACGGGAAGAGTCTTCCTTTAC GATATTagttccatgtcctcaggvtg (SEQ ID NO:167) |
| 758 | | | | | | GAGGAGGGGCAGCAAACGGGAAGAGTCTTCCTTTAC GATATTagacttcatgataacgttgc (SEQ ID NO:168) |
| 780 | | | | | | GAGGAGGGGCAGCAAACGGGAAGAGTCTTCCTTTAC GATATTgttcactgggaactccca (SEQ ID NO:169) |
| 882 | | | | | | GAGGAGGGGCAGCAAACGGGAAGAGTCTTCCTTTAC GATATTgggagggatgggctatac (SEQ ID NO:170) |
| 913 | | | | | | GAGGAGGGGCAGCAAACGGGAAGAGTCTTCCTTTAC GATATTgatgatcgggagagtgag (SEQ ID NO:171) |
| 985 | | | | | | GAGGAGGGGCAGCAAACGGGAAGAGTCTTCCTTTAC GATATTtttgacaatcttgcatgccc (SEQ ID NO:172) |
| 1007 | | | | | | GAGGAGGGGCAGCAAACGGGAAGAGTCTTCCTTTAC GATATTaaagaacttgcaatcctgg (SEQ ID NO:173) |
| 1029 | | | | | | GAGGAGGGGCAGCAAACGGGAAGAGTCTTCCTTTAC GATATTcattgggcatgtctggatc (SEQ ID NO:174) |
| 1059 | | | | | | GAGGAGGGGCAGCAAACGGGAAGAGTCTTCCTTTAC GATATTcatcgtcttaagggagtc (SEQ ID NO:175) |
| 1115 | | | | | | GAGGAGGGGCAGCAAACGGGAAGAGTCTTCCTTTAC GATATTaatgcaagcatctgactgg (SEQ ID NO:176) |
| 1144 | | | | | | GAGGAGGGGCAGCAAACGGGAAGAGTCTTCCTTTAC GATATTagccagcagatgtgaacac (SEQ ID NO:177) |
| 1169 | | | | | | GAGGAGGGGCAGCAAACGGGAAGAGTCTTCCTTTAC GATATTcaggatgtgcgtgatgaaga (SEQ ID NO:178) |
| drd2.a.11 92 | | | | | | GAGGAGGGGCAGCAAACGGGAAGAGTCTTCCTTTAC GATATTatgttcagtcacagtgtat (SEQ ID NO:179) |
| drd2.a.13 10 | | | | | | GAGGAGGGGCAGCAAACGGGAAGAGTCTTCCTTTAC GATATTgtgcaggatcttcatgaagg (SEQ ID NO:180) |

FIG. 13 (Cont. 14)

| | proprieta ry | 20mer smFISH DNA probe | HCR | B1 | 2nM per probe | 6 | midbrain | Proprietary, Biosearch (Petaluma, CA) |
|---|---|---|---|---|---|---|---|---|
| Th | | | | | | | | |
| cfos | proprieta ry | 20mer smFISH DNA probe | HCR | B1 | 2nM per probe | 9 | hippocampus | Proprietary, Biosearch (Petaluma, CA) |
| miR-10 | | LNA probe | anti-DIG + TSA | - | 12.5nM | 8 | | cacaaattcgttctacaggta (SEQ ID NO:181) |
| miR-21 | | LNA probe | anti-DIG + TSA | - | 12.5nM | 8 | | agtctgataagcta (SEQ ID NO:182) |
| miR-124 | | LNA probe | anti-DIG + TSA | - | 12.5nM | 8 | | ggcattcaccgcgtgcctta (SEQ ID NO:183) |
| miR-128 | | LNA probe | anti-DIG + TSA | - | 12.5nM | 8 | forebrain | aaagagaccgttcactgtga (SEQ ID NO:184) |

FIG. 13 (Cont. 15)

SEQUENCE LISTING

<160> NUMBER OF SEQ ID NOS: 184

<210> SEQ ID NO 1
<211> LENGTH: 50
<212> TYPE: DNA
<213> ORGANISM: Artificial Sequence
<220> FEATURE:
<223> OTHER INFORMATION: Synthetic probe

<400> SEQUENCE: 1
gaatgtcttc cagaagaagt tcttgcagcc agctttgcgt tcccggggtg         50

<210> SEQ ID NO 2
<211> LENGTH: 100
<212> TYPE: DNA
<213> ORGANISM: Artificial Sequence
<220> FEATURE:
<223> OTHER INFORMATION: Synthetic probe

<400> SEQUENCE: 2
gaatgtcttc cagaagaagt tcttgcagcc agctttgcgt tcccggggtg ccattgctgg  60

```
gttcgagttg gcagacctct gcagctccag cctcatctcg                          100
```

<210> SEQ ID NO 3
<211> LENGTH: 150
<212> TYPE: DNA
<213> ORGANISM: Artificial Sequence
<220> FEATURE:
<223> OTHER INFORMATION: Synthetic probe

<400> SEQUENCE: 3

```
gaatgtcttc cagaagaagt tcttgcagcc agctttgcgt tcccggggtg ccattgctgg    60
gttcgagttg gcagacctct gcagctccag cctcatctcg tcctgctcag ctgcctgggg   120
caaatcctcg ggctccaggg catcattctc                                    150
```

<210> SEQ ID NO 4
<211> LENGTH: 46
<212> TYPE: DNA
<213> ORGANISM: Artificial Sequence
<220> FEATURE:
<223> OTHER INFORMATION: Synthetic probe

<400> SEQUENCE: 4

```
gcaaatcctc gggctccagg gcatcattct ctgtctggtt gggctc                   46
```

<210> SEQ ID NO 5
<211> LENGTH: 48
<212> TYPE: DNA
<213> ORGANISM: Artificial Sequence
<220> FEATURE:
<223> OTHER INFORMATION: Synthetic probe

<400> SEQUENCE: 5

```
gttcgagttg gcagacctct gcagctccag cctcatctcg tcctgctc                 48
```

<210> SEQ ID NO 6
<211> LENGTH: 45
<212> TYPE: DNA
<213> ORGANISM: Artificial Sequence
<220> FEATURE:
<223> OTHER INFORMATION: Synthetic probe

<400> SEQUENCE: 6

```
cagccaagct ggagcgcggt gggtcagtct agtcgcaggt cctca                    45
```

<210> SEQ ID NO 7
<211> LENGTH: 128
<212> TYPE: DNA
<213> ORGANISM: Artificial Sequence
<220> FEATURE:
<223> OTHER INFORMATION: Synthetic probe

<400> SEQUENCE: 7

```
gaggagggca gcaaacggga agagtcttcc tttacgatat tgcaaatcct cgggctccag    60
ggcatcattc tctgtctggt tgggctcata tagcattctt tcttgaggag ggcagcaaac   120
gggaagag                                                            128
```

<210> SEQ ID NO 8
<211> LENGTH: 130
<212> TYPE: DNA
<213> ORGANISM: Artificial Sequence
<220> FEATURE:
<223> OTHER INFORMATION: Synthetic probe

<400> SEQUENCE: 8
gaggagggca gcaaacggga agagtcttcc tttacgatat tgttcgagtt ggcagacctc    60
tgcagctcca gcctcatctc gtcctgctca tatagcattc tttcttgagg agggcagcaa   120
acgggaagag                                                          130

<210> SEQ ID NO 9
<211> LENGTH: 127
<212> TYPE: DNA
<213> ORGANISM: Artificial Sequence
<220> FEATURE:
<223> OTHER INFORMATION: Synthetic probe

<400> SEQUENCE: 9
gaggagggca gcaaacggga agagtcttcc tttacgatat tcagccaagc tggagcgcgg    60
tgggtcagtc tagtcgcagg tcctcaatat agcattcttt cttgaggagg gcagcaaacg   120
ggaagag                                                             127

<210> SEQ ID NO 10
<211> LENGTH: 127
<212> TYPE: DNA
<213> ORGANISM: Artificial Sequence
<220> FEATURE:
<223> OTHER INFORMATION: Synthetic probe

<400> SEQUENCE: 10
gaggagggca gcaaacggga agagtcttcc tttacgatat ttccagaaga agttcttgca    60
gccagctttg cgttcccggg gtgccaatat agcattcttt cttgaggagg gcagcaaacg   120
ggaagag                                                             127

<210> SEQ ID NO 11
<211> LENGTH: 128
<212> TYPE: DNA
<213> ORGANISM: Artificial Sequence
<220> FEATURE:
<223> OTHER INFORMATION: Synthetic probe

<400> SEQUENCE: 11
cctcgtaaat cctcatcaat catccagtaa accgccaaaa agcaaatcct cgggctccag    60
ggcatcattc tctgtctggt tgggctcaaa aaagctcagt ccatcctcgt aaatcctcat   120
caatcatc                                                            128

<210> SEQ ID NO 12
<211> LENGTH: 130
<212> TYPE: DNA
<213> ORGANISM: Artificial Sequence
<220> FEATURE:
<223> OTHER INFORMATION: Synthetic probe

<400> SEQUENCE: 12
cctcgtaaat cctcatcaat catccagtaa accgccaaaa agttcgagtt ggcagacctc    60
tgcagctcca gcctcatctc gtcctgctca aaaaagctca gtccatcctc gtaaatcctc   120
atcaatcatc                                                          130

<210> SEQ ID NO 13
<211> LENGTH: 127
<212> TYPE: DNA
<213> ORGANISM: Artificial Sequence
<220> FEATURE:
<223> OTHER INFORMATION: Synthetic probe

```
<400> SEQUENCE: 13
cctcgtaaat cctcatcaat catccagtaa accgccaaaa acagccaagc tggagcgcgg      60
tgggtcagtc tagtcgcagg tcctcaaaaa aagctcagtc catcctcgta aatcctcatc     120
aatcatc                                                              127

<210> SEQ ID NO 14
<211> LENGTH: 127
<212> TYPE: DNA
<213> ORGANISM: Artificial Sequence
<220> FEATURE:
<223> OTHER INFORMATION: Synthetic probe

<400> SEQUENCE: 14
cctcgtaaat cctcatcaat catccagtaa accgccaaaa atccagaaga agttcttgca      60
gccagctttg cgttcccggg gtgccaaaaa aagctcagtc catcctcgta aatcctcatc     120
aatcatc                                                              127

<210> SEQ ID NO 15
<211> LENGTH: 128
<212> TYPE: DNA
<213> ORGANISM: Artificial Sequence
<220> FEATURE:
<223> OTHER INFORMATION: Synthetic probe

<400> SEQUENCE: 15
ctcactccca atctctatct accctacaaa tccaataaaa agcaaatcct cgggctccag      60
ggcatcattc tctgtctggt tgggctcatt ttcacttcat atcactcact cccaatctct     120
atctaccc                                                             128

<210> SEQ ID NO 16
<211> LENGTH: 130
<212> TYPE: DNA
<213> ORGANISM: Artificial Sequence
<220> FEATURE:
<223> OTHER INFORMATION: Synthetic probe

<400> SEQUENCE: 16
ctcactccca atctctatct accctacaaa tccaataaaa agttcgagtt ggcagacctc      60
tgcagctcca gcctcatctc gtcctgctca ttttcacttc atatcactca ctcccaatct    120
ctatctaccc                                                           130

<210> SEQ ID NO 17
<211> LENGTH: 127
<212> TYPE: DNA
<213> ORGANISM: Artificial Sequence
<220> FEATURE:
<223> OTHER INFORMATION: Synthetic probe

<400> SEQUENCE: 17
ctcactccca atctctatct accctacaaa tccaataaaa acagccaagc tggagcgcgg      60
tgggtcagtc tagtcgcagg tcctcaattt tcacttcata tcactcactc ccaatctcta    120
tctaccc                                                              127

<210> SEQ ID NO 18
<211> LENGTH: 127
<212> TYPE: DNA
<213> ORGANISM: Artificial Sequence
<220> FEATURE:
<223> OTHER INFORMATION: Synthetic probe
```

-continued

<400> SEQUENCE: 18
ctcactccca atctctatct accctacaaa tccaataaaa atccagaaga agttcttgca    60
gccagctttg cgttcccggg gtgccaattt tcacttcata tcactcactc ccaatctcta   120
tctaccc                                                             127

<210> SEQ ID NO 19
<211> LENGTH: 130
<212> TYPE: DNA
<213> ORGANISM: Artificial Sequence
<220> FEATURE:
<223> OTHER INFORMATION: Synthetic probe

<400> SEQUENCE: 19
ctcactccca atctctatct accctacaaa tccaataaaa acagtcttca atttctaatg    60
cagggtcaag ttgagcatcg ggggccagga ttttcacttc atatcactca ctcccaatct   120
ctatctaccc                                                          130

<210> SEQ ID NO 20
<211> LENGTH: 136
<212> TYPE: DNA
<213> ORGANISM: Artificial Sequence
<220> FEATURE:
<223> OTHER INFORMATION: Synthetic probe

<400> SEQUENCE: 20
ctcactccca atctctatct accctacaaa tccaataaaa attcaatttc taatgcaggg    60
tcaagttgag catcggggc caggagttaa ggaagatttt cacttcatat cactcactcc   120
caatctctat ctaccc                                                   136

<210> SEQ ID NO 21
<211> LENGTH: 132
<212> TYPE: DNA
<213> ORGANISM: Artificial Sequence
<220> FEATURE:
<223> OTHER INFORMATION: Synthetic probe

<400> SEQUENCE: 21
gaggagggca gcaaacggga agagtcttcc tttacgatat tttcttgatg tcctcagcgc    60
tgagcacgtc tgtcatcgac atcctgcaac tatatagcat tctttcttga ggagggcagc   120
aaacgggaag ag                                                       132

<210> SEQ ID NO 22
<211> LENGTH: 132
<212> TYPE: DNA
<213> ORGANISM: Artificial Sequence
<220> FEATURE:
<223> OTHER INFORMATION: Synthetic probe

<400> SEQUENCE: 22
gaggagggca gcaaacggga agagtcttcc tttacgatat ttgtctccag cggccagaag    60
cgtctttgtt tctttagcag acaagtctct gatatagcat tctttcttga ggagggcagc   120
aaacgggaag ag                                                       132

<210> SEQ ID NO 23
<211> LENGTH: 132
<212> TYPE: DNA
<213> ORGANISM: Artificial Sequence
<220> FEATURE:

<223> OTHER INFORMATION: Synthetic probe

<400> SEQUENCE: 23

```
gaggagggca gcaaacggga agagtcttcc tttacgatat ttgtctccag cggccagaag    60
cgtctttgtt tctttagcag acaagtctct gatatagcat tctttcttga ggagggcagc   120
aaacgggaag ag                                                        132
```

<210> SEQ ID NO 24
<211> LENGTH: 132
<212> TYPE: DNA
<213> ORGANISM: Artificial Sequence
<220> FEATURE:
<223> OTHER INFORMATION: Synthetic probe

<400> SEQUENCE: 24

```
gaggagggca gcaaacggga agagtcttcc tttacgatat ttggagaggt gggggaccca    60
agcagtcagc gccacttagc tttcagccac catatagcat tctttcttga ggagggcagc   120
aaacgggaag ag                                                        132
```

<210> SEQ ID NO 25
<211> LENGTH: 50
<212> TYPE: DNA
<213> ORGANISM: Artificial Sequence
<220> FEATURE:
<223> OTHER INFORMATION: Synthetic probe

<400> SEQUENCE: 25

```
tacaggtggt gtccgattgg tacagccttt attgtttctc cagcatttcc              50
```

<210> SEQ ID NO 26
<211> LENGTH: 50
<212> TYPE: DNA
<213> ORGANISM: Artificial Sequence
<220> FEATURE:
<223> OTHER INFORMATION: Synthetic probe

<400> SEQUENCE: 26

```
agtaccaagc aggcaggaga tatcggggcg ttgtcctttg acttatctca              50
```

<210> SEQ ID NO 27
<211> LENGTH: 50
<212> TYPE: DNA
<213> ORGANISM: Artificial Sequence
<220> FEATURE:
<223> OTHER INFORMATION: Synthetic probe

<400> SEQUENCE: 27

```
aagatggacg atccatcacc cccatctcct tgtgggaaag gtgcagagat              50
```

<210> SEQ ID NO 28
<211> LENGTH: 50
<212> TYPE: DNA
<213> ORGANISM: Artificial Sequence
<220> FEATURE:
<223> OTHER INFORMATION: Synthetic probe

<400> SEQUENCE: 28

```
ggagtccttt gatctagcta gtcctgaagg actcaacccc ttcccttccc              50
```

<210> SEQ ID NO 29
<211> LENGTH: 50
<212> TYPE: DNA
<213> ORGANISM: Artificial Sequence

```
<220> FEATURE:
<223> OTHER INFORMATION: Synthetic probe

<400> SEQUENCE: 29
aagaaagaaa aaaaacttgc caaaccaaca ccctgccagg cctgggtcct      50

<210> SEQ ID NO 30
<211> LENGTH: 132
<212> TYPE: DNA
<213> ORGANISM: Artificial Sequence
<220> FEATURE:
<223> OTHER INFORMATION: Synthetic probe

<400> SEQUENCE: 30
gaggagggca gcaaacggga agagtcttcc tttacgatat tactctgccg ccgtccaatg      60
aaccttgggg acgtgacagc ctcggcctgc tatatagcat tctttcttga ggagggcagc     120
aaacgggaag ag                                                         132

<210> SEQ ID NO 31
<211> LENGTH: 132
<212> TYPE: DNA
<213> ORGANISM: Artificial Sequence
<220> FEATURE:
<223> OTHER INFORMATION: Synthetic probe

<400> SEQUENCE: 31
gaggagggca gcaaacggga agagtcttcc tttacgatat tctggaagcc agtccgttcc      60
ttcaagaagt gagacacatc ctccagctgt gatatagcat tctttcttga ggagggcagc     120
aaacgggaag ag                                                         132

<210> SEQ ID NO 32
<211> LENGTH: 132
<212> TYPE: DNA
<213> ORGANISM: Artificial Sequence
<220> FEATURE:
<223> OTHER INFORMATION: Synthetic probe

<400> SEQUENCE: 32
gaggagggca gcaaacggga agagtcttcc tttacgatat tcatcactga agctctctga      60
cacgaagtac accggctggt aggtttgatc tatatagcat tctttcttga ggagggcagc     120
aaacgggaag ag                                                         132

<210> SEQ ID NO 33
<211> LENGTH: 132
<212> TYPE: DNA
<213> ORGANISM: Artificial Sequence
<220> FEATURE:
<223> OTHER INFORMATION: Synthetic probe

<400> SEQUENCE: 33
gaggagggca gcaaacggga agagtcttcc tttacgatat ttctaaggag cgccggatgg      60
tgtgaggact gtccagtaca tcaatggcca gatatagcat tctttcttga ggagggcagc     120
aaacgggaag ag                                                         132

<210> SEQ ID NO 34
<211> LENGTH: 132
<212> TYPE: DNA
<213> ORGANISM: Artificial Sequence
<220> FEATURE:
<223> OTHER INFORMATION: Synthetic probe
```

<400> SEQUENCE: 34
gaggagggca gcaaacggga agagtcttcc tttacgatat tccgggtctc taagtggtgg    60
attttggctt caaatgtctc aaacactttc aatatagcat tctttcttga ggagggcagc   120
aaacgggaag ag                                                       132

<210> SEQ ID NO 35
<211> LENGTH: 132
<212> TYPE: DNA
<213> ORGANISM: Artificial Sequence
<220> FEATURE:
<223> OTHER INFORMATION: Synthetic probe

<400> SEQUENCE: 35
gaggagggca gcaaacggga agagtcttcc tttacgatat tgcagctcgt ggcagcagtc    60
tggctcgggt gagtgcatag gtgaggaggc aatatagcat tctttcttga ggagggcagc   120
aaacgggaag ag                                                       132

<210> SEQ ID NO 36
<211> LENGTH: 132
<212> TYPE: DNA
<213> ORGANISM: Artificial Sequence
<220> FEATURE:
<223> OTHER INFORMATION: Synthetic probe

<400> SEQUENCE: 36
gaggagggca gcaaacggga agagtcttcc tttacgatat tttcacagag aatgggcgct    60
ggatacgaga ggcatagttc ctgagcttgt catatagcat tctttcttga ggagggcagc   120
aaacgggaag ag                                                       132

<210> SEQ ID NO 37
<211> LENGTH: 132
<212> TYPE: DNA
<213> ORGANISM: Artificial Sequence
<220> FEATURE:
<223> OTHER INFORMATION: Synthetic probe

<400> SEQUENCE: 37
gaggagggca gcaaacggga agagtcttcc tttacgatat tgcagccagg tcgccactgg    60
gcacctcgaa gcgcacaaag tactccaggt gatatagcat tctttcttga ggagggcagc   120
aaacgggaag ag                                                       132

<210> SEQ ID NO 38
<211> LENGTH: 132
<212> TYPE: DNA
<213> ORGANISM: Artificial Sequence
<220> FEATURE:
<223> OTHER INFORMATION: Synthetic probe

<400> SEQUENCE: 38
gaggagggca gcaaacggga agagtcttcc tttacgatat taggagctct ccataggaag    60
acagcagccc tgcaccgtaa gccttcagct catatagcat tctttcttga ggagggcagc   120
aaacgggaag ag                                                       132

<210> SEQ ID NO 39
<211> LENGTH: 132
<212> TYPE: DNA
<213> ORGANISM: Artificial Sequence
<220> FEATURE:
<223> OTHER INFORMATION: Synthetic probe

<400> SEQUENCE: 39
gaggagggca gcaaacggga agagtcttcc tttacgatat tagggtcaaa cttggtgacc    60
aggtggtgac acttatccaa ctctgacact tatatagcat tctttcttga ggagggcagc   120
aaacgggaag ag                                                      132

<210> SEQ ID NO 40
<211> LENGTH: 132
<212> TYPE: DNA
<213> ORGANISM: Artificial Sequence
<220> FEATURE:
<223> OTHER INFORMATION: Synthetic probe

<400> SEQUENCE: 40
gaggagggca gcaaacggga agagtcttcc tttacgatat tactctgccg ccgtccaatg    60
aaccttgggg acgtgacagc ctcggcctgc tatatagcat tctttcttga ggagggcagc   120
aaacgggaag ag                                                      132

<210> SEQ ID NO 41
<211> LENGTH: 132
<212> TYPE: DNA
<213> ORGANISM: Artificial Sequence
<220> FEATURE:
<223> OTHER INFORMATION: Synthetic probe

<400> SEQUENCE: 41
gaggagggca gcaaacggga agagtcttcc tttacgatat tctggaagcc agtccgttcc    60
ttcaagaagt gagacacatc ctccagctgt gatatagcat tctttcttga ggagggcagc   120
aaacgggaag ag                                                      132

<210> SEQ ID NO 42
<211> LENGTH: 132
<212> TYPE: DNA
<213> ORGANISM: Artificial Sequence
<220> FEATURE:
<223> OTHER INFORMATION: Synthetic probe

<400> SEQUENCE: 42
gaggagggca gcaaacggga agagtcttcc tttacgatat tcatcactga agctctctga    60
cacgaagtac accggctggt aggtttgatc tatatagcat tctttcttga ggagggcagc   120
aaacgggaag ag                                                      132

<210> SEQ ID NO 43
<211> LENGTH: 132
<212> TYPE: DNA
<213> ORGANISM: Artificial Sequence
<220> FEATURE:
<223> OTHER INFORMATION: Synthetic probe

<400> SEQUENCE: 43
gaggagggca gcaaacggga agagtcttcc tttacgatat ttctaaggag cgccggatgg    60
tgtgaggact gtccagtaca tcaatggcca gatatagcat tctttcttga ggagggcagc   120
aaacgggaag ag                                                      132

<210> SEQ ID NO 44
<211> LENGTH: 132
<212> TYPE: DNA
<213> ORGANISM: Artificial Sequence
<220> FEATURE:

<223> OTHER INFORMATION: Synthetic probe

<400> SEQUENCE: 44
gaggagggca gcaaacggga agagtcttcc tttacgatat tccgggtctc taagtggtgg        60
attttggctt caaatgtctc aaacactttc aatatagcat tctttcttga ggagggcagc       120
aaacgggaag ag       132

<210> SEQ ID NO 45
<211> LENGTH: 132
<212> TYPE: DNA
<213> ORGANISM: Artificial Sequence
<220> FEATURE:
<223> OTHER INFORMATION: Synthetic probe

<400> SEQUENCE: 45
gaggagggca gcaaacggga agagtcttcc tttacgatat tgcagctcgt ggcagcagtc        60
tggctcgggt gagtgcatag gtgaggaggc aatatagcat tctttcttga ggagggcagc       120
aaacgggaag ag       132

<210> SEQ ID NO 46
<211> LENGTH: 132
<212> TYPE: DNA
<213> ORGANISM: Artificial Sequence
<220> FEATURE:
<223> OTHER INFORMATION: Synthetic probe

<400> SEQUENCE: 46
gaggagggca gcaaacggga agagtcttcc tttacgatat tttcacagag aatgggcgct        60
ggatacgaga ggcatagttc ctgagcttgt catatagcat tctttcttga ggagggcagc       120
aaacgggaag ag       132

<210> SEQ ID NO 47
<211> LENGTH: 132
<212> TYPE: DNA
<213> ORGANISM: Artificial Sequence
<220> FEATURE:
<223> OTHER INFORMATION: Synthetic probe

<400> SEQUENCE: 47
gaggagggca gcaaacggga agagtcttcc tttacgatat tgcagccagg tcgccactgg        60
gcacctcgaa gcgcacaaag tactccaggt gatatagcat tctttcttga ggagggcagc       120
aaacgggaag ag       132

<210> SEQ ID NO 48
<211> LENGTH: 132
<212> TYPE: DNA
<213> ORGANISM: Artificial Sequence
<220> FEATURE:
<223> OTHER INFORMATION: Synthetic probe

<400> SEQUENCE: 48
gaggagggca gcaaacggga agagtcttcc tttacgatat taggagctct ccataggaag        60
acagcagccc tgcaccgtaa gccttcagct catatagcat tctttcttga ggagggcagc       120
aaacgggaag ag       132

<210> SEQ ID NO 49
<211> LENGTH: 132
<212> TYPE: DNA
<213> ORGANISM: Artificial Sequence

```
<220> FEATURE:
<223> OTHER INFORMATION: Synthetic probe

<400> SEQUENCE: 49
gaggagggca gcaaacggga agagtcttcc tttacgatat tagggtcaaa cttggtgacc    60
aggtggtgac acttatccaa ctctgacact tatatagcat tctttcttga ggagggcagc   120
aaacgggaag ag                                                       132

<210> SEQ ID NO 50
<211> LENGTH: 132
<212> TYPE: DNA
<213> ORGANISM: Artificial Sequence
<220> FEATURE:
<223> OTHER INFORMATION: Synthetic probe

<400> SEQUENCE: 50
gaggagggca gcaaacggga agagtcttcc tttacgatat tatccaaaga actgctgagg    60
cttgggtctt cgggcgattc tctgcagaag aatatagcat tctttcttga ggagggcagc   120
aaacgggaag ag                                                       132

<210> SEQ ID NO 51
<211> LENGTH: 132
<212> TYPE: DNA
<213> ORGANISM: Artificial Sequence
<220> FEATURE:
<223> OTHER INFORMATION: Synthetic probe

<400> SEQUENCE: 51
gaggagggca gcaaacggga agagtcttcc tttacgatat ttttacgtct tctttcgtag    60
ttctgcatcg cgcttctttc ataagccaca gatatagcat tctttcttga ggagggcagc   120
aaacgggaag ag                                                       132

<210> SEQ ID NO 52
<211> LENGTH: 132
<212> TYPE: DNA
<213> ORGANISM: Artificial Sequence
<220> FEATURE:
<223> OTHER INFORMATION: Synthetic probe

<400> SEQUENCE: 52
gaggagggca gcaaacggga agagtcttcc tttacgatat tatcattcct catagcgcac    60
attttatttt accgttcact gctcactgac aatatagcat tctttcttga ggagggcagc   120
aaacgggaag ag                                                       132

<210> SEQ ID NO 53
<211> LENGTH: 132
<212> TYPE: DNA
<213> ORGANISM: Artificial Sequence
<220> FEATURE:
<223> OTHER INFORMATION: Synthetic probe

<400> SEQUENCE: 53
gaggagggca gcaaacggga agagtcttcc tttacgatat tccagggta gcgtgagaga    60 gacgcacagg agtctctgct tccagcagca gatatagcat tctttcttga ggagggcagc   120
aaacgggaag ag                                                       132

<210> SEQ ID NO 54
<211> LENGTH: 132
<212> TYPE: DNA
```

```
<213> ORGANISM: Artificial Sequence
<220> FEATURE:
<223> OTHER INFORMATION: Synthetic probe

<400> SEQUENCE: 54
gaggagggca gcaaacggga agagtcttcc tttacgatat tacaggaaac atgctgctag      60
gatacaaata gagtcaaata ccgaagtctc aatatagcat tctttcttga ggagggcagc     120
aaacgggaag ag                                                          132

<210> SEQ ID NO 55
<211> LENGTH: 127
<212> TYPE: DNA
<213> ORGANISM: Artificial Sequence
<220> FEATURE:
<223> OTHER INFORMATION: Synthetic probe

<400> SEQUENCE: 55
gaggagggca gcaaacggga agagtcttcc tttacgatat ttgctcagca ctttcagcaa      60
tccttccaga gagacagggc ggctgtatat agcattcttt cttgaggagg gcagcaaacg     120
ggaagag                                                                127

<210> SEQ ID NO 56
<211> LENGTH: 131
<212> TYPE: DNA
<213> ORGANISM: Artificial Sequence
<220> FEATURE:
<223> OTHER INFORMATION: Synthetic probe

<400> SEQUENCE: 56
gaggagggca gcaaacggga agagtcttcc tttacgatat tccataagtc ccacaaagaa      60
gtcgtgcatg tcacgtttct gtggaagtga atatagcatt ctttcttgag gagggcagca     120
aacgggaaga g                                                           131

<210> SEQ ID NO 57
<211> LENGTH: 130
<212> TYPE: DNA
<213> ORGANISM: Artificial Sequence
<220> FEATURE:
<223> OTHER INFORMATION: Synthetic probe

<400> SEQUENCE: 57
gaggagggca gcaaacggga agagtcttcc tttacgatat tgggtgttct cttcaaccac      60
gtcggtggga gtgtctggtt ggctgttcca tatagcattc tttcttgagg agggcagcaa     120
acgggaagag                                                             130

<210> SEQ ID NO 58
<211> LENGTH: 128
<212> TYPE: DNA
<213> ORGANISM: Artificial Sequence
<220> FEATURE:
<223> OTHER INFORMATION: Synthetic probe

<400> SEQUENCE: 58
gaggagggca gcaaacggga agagtcttcc tttacgatat tgggaggaga agaggaagca      60
ggagcaggca ctgctttatg atgcaatata tagcattctt tcttgaggag gcagcaaac      120 gggaagag                                                               128

<210> SEQ ID NO 59
<211> LENGTH: 127
```

```
<212> TYPE: DNA
<213> ORGANISM: Artificial Sequence
<220> FEATURE:
<223> OTHER INFORMATION: Synthetic probe

<400> SEQUENCE: 59
gaggagggca gcaaacggga agagtcttcc tttacgatat tgaggcagct gatagagatc    60
agagtcctta ctgagcctcc ctccctatat agcattcttt cttgaggagg gcagcaaacg   120
ggaagag                                                             127

<210> SEQ ID NO 60
<211> LENGTH: 130
<212> TYPE: DNA
<213> ORGANISM: Artificial Sequence
<220> FEATURE:
<223> OTHER INFORMATION: Synthetic probe

<400> SEQUENCE: 60
gaggagggca gcaaacggga agagtcttcc tttacgatat ttgttcatat gcagcttcta    60
tgcagagtag ggaagggagc aacaggaga tatagcattc tttcttgagg agggcagcaa   120
acgggaagag                                                          130

<210> SEQ ID NO 61
<211> LENGTH: 49
<212> TYPE: DNA
<213> ORGANISM: Artificial Sequence
<220> FEATURE:
<223> OTHER INFORMATION: Synthetic probe

<400> SEQUENCE: 61
gccggtgggt cctccgtacg tgttccagca tctcagctcg gcacttacc                49

<210> SEQ ID NO 62
<211> LENGTH: 55
<212> TYPE: DNA
<213> ORGANISM: Artificial Sequence
<220> FEATURE:
<223> OTHER INFORMATION: Synthetic probe

<400> SEQUENCE: 62
tccttcttga actccaccca gttcttcacc gagccctgct tgaactccca ccact         55

<210> SEQ ID NO 63
<211> LENGTH: 46
<212> TYPE: DNA
<213> ORGANISM: Artificial Sequence
<220> FEATURE:
<223> OTHER INFORMATION: Synthetic probe

<400> SEQUENCE: 63
cccgcttgcg ccagaggaac tggtcgagtg gttcaccctg cttctg                   46

<210> SEQ ID NO 64
<211> LENGTH: 59
<212> TYPE: DNA
<213> ORGANISM: Artificial Sequence
<220> FEATURE:
<223> OTHER INFORMATION: Synthetic probe

<400> SEQUENCE: 64
gctggtaaga gcaggtgtga gtgcctccgt ctcatcctct gtgggcagtg gggtgccag     59

<210> SEQ ID NO 65
```

```
<211> LENGTH: 132
<212> TYPE: DNA
<213> ORGANISM: Artificial Sequence
<220> FEATURE:
<223> OTHER INFORMATION: Synthetic probe

<400> SEQUENCE: 65
gaggagggca gcaaacggga agagtcttcc tttacgatat taggagctta gcgagtgtgg      60
caggctcgtc gccgctgaag ctagagaggc catatagcat tctttcttga ggagggcagc    120
aaacgggaag ag                                                         132

<210> SEQ ID NO 66
<211> LENGTH: 132
<212> TYPE: DNA
<213> ORGANISM: Artificial Sequence
<220> FEATURE:
<223> OTHER INFORMATION: Synthetic probe

<400> SEQUENCE: 66
gaggagggca gcaaacggga agagtcttcc tttacgatat ttacaggtcc cgcttgcgcc      60
agaggaactg gtcgagtggt tcaccctgct tatatagcat tctttcttga ggagggcagc    120
aaacgggaag ag                                                         132

<210> SEQ ID NO 67
<211> LENGTH: 132
<212> TYPE: DNA
<213> ORGANISM: Artificial Sequence
<220> FEATURE:
<223> OTHER INFORMATION: Synthetic probe

<400> SEQUENCE: 67
gaggagggca gcaaacggga agagtcttcc tttacgatat tcgctgtgag tcgccggtgg      60
gcacgtagcc gtccaagttg ttctccagct tatatagcat tctttcttga ggagggcagc    120
aaacgggaag ag                                                         132

<210> SEQ ID NO 68
<211> LENGTH: 132
<212> TYPE: DNA
<213> ORGANISM: Artificial Sequence
<220> FEATURE:
<223> OTHER INFORMATION: Synthetic probe

<400> SEQUENCE: 68
gaggagggca gcaaacggga agagtcttcc tttacgatat tcccacctct ccagacggta      60
gaagacctcc ctccacacgt gcatctcacg catatagcat tctttcttga ggagggcagc    120
aaacgggaag ag                                                         132

<210> SEQ ID NO 69
<211> LENGTH: 132
<212> TYPE: DNA
<213> ORGANISM: Artificial Sequence
<220> FEATURE:
<223> OTHER INFORMATION: Synthetic probe

<400> SEQUENCE: 69
gaggagggca gcaaacggga agagtcttcc tttacgatat tactcgctgg taagagcagg      60
tgtgagtgcc tccgtctcat cctctgtggg catatagcat tctttcttga ggagggcagc    120
aaacgggaag ag                                                         132
```

```
<210> SEQ ID NO 70
<211> LENGTH: 126
<212> TYPE: DNA
<213> ORGANISM: Artificial Sequence
<220> FEATURE:
<223> OTHER INFORMATION: Synthetic probe

<400> SEQUENCE: 70
gaggagggca gcaaacggga agagtcttcc tttacgatat tccggtgggt cctccgtacg      60
tgttccagca tctcagctcg gcacttacca gcattctttc ttgaggaggg cagcaaacgg     120
gaagag                                                                126

<210> SEQ ID NO 71
<211> LENGTH: 137
<212> TYPE: DNA
<213> ORGANISM: Artificial Sequence
<220> FEATURE:
<223> OTHER INFORMATION: Synthetic probe

<400> SEQUENCE: 71
gaggagggca gcaaacggga agagtcttcc tttacgatat ttccttcttg aactccaccc      60
agttcttcac cgagccctgc ttgaactccc accactatat agcattcttt cttgaggagg     120
gcagcaaacg ggaagag                                                    137

<210> SEQ ID NO 72
<211> LENGTH: 128
<212> TYPE: DNA
<213> ORGANISM: Artificial Sequence
<220> FEATURE:
<223> OTHER INFORMATION: Synthetic probe

<400> SEQUENCE: 72
gaggagggca gcaaacggga agagtcttcc tttacgatat tcccgcttgc gccagaggaa      60
ctggtcgagt ggttcaccct gcttctgata tagcattctt tcttgaggag gcagcaaac     120 gggaagag                                                              128

<210> SEQ ID NO 73
<211> LENGTH: 141
<212> TYPE: DNA
<213> ORGANISM: Artificial Sequence
<220> FEATURE:
<223> OTHER INFORMATION: Synthetic probe

<400> SEQUENCE: 73
gaggagggca gcaaacggga agagtcttcc tttacgatat tgctggtaag agcaggtgtg      60
agtgcctccg tctcatcctc tgtgggcagt ggggtgccag atatagcatt ctttcttgag     120
gagggcagca aacgggaaga g                                               141

<210> SEQ ID NO 74
<211> LENGTH: 128
<212> TYPE: DNA
<213> ORGANISM: Artificial Sequence
<220> FEATURE:
<223> OTHER INFORMATION: Synthetic probe

<400> SEQUENCE: 74
gaggagggca gcaaacggga agagtcttcc tttacgatat tgaatgaggg tagcacagct      60
ggggttccta ggacataggc tgcctggata tagcattctt tcttgaggag gcagcaaac     120 gggaagag                                                              128
```

<210> SEQ ID NO 75
<211> LENGTH: 129
<212> TYPE: DNA
<213> ORGANISM: Artificial Sequence
<220> FEATURE:
<223> OTHER INFORMATION: Synthetic probe

<400> SEQUENCE: 75
gaggagggca gcaaacggga agagtcttcc tttacgatat tgctgagcta gggccaggag      60
tgtacagtcc ccattaccag ggctgctaat atagcattct ttcttgagga gggcagcaaa     120
cgggaagag                                                             129

<210> SEQ ID NO 76
<211> LENGTH: 132
<212> TYPE: DNA
<213> ORGANISM: Artificial Sequence
<220> FEATURE:
<223> OTHER INFORMATION: Synthetic probe

<400> SEQUENCE: 76
gaggagggca gcaaacggga agagtcttcc tttacgatat tggagggttg gggaagctct      60
tctggtgttg agatcacacc tagttcagga gatatagcat tctttcttga ggagggcagc     120
aaacgggaag ag                                                         132

<210> SEQ ID NO 77
<211> LENGTH: 136
<212> TYPE: DNA
<213> ORGANISM: Artificial Sequence
<220> FEATURE:
<223> OTHER INFORMATION: Synthetic probe

<400> SEQUENCE: 77
gaggagggca gcaaacggga agagtcttcc tttacgatat tcaactgtcc ttgtagtgaa      60
ctggttagtg ggtctgggaa ggtagcactg ctgggatata gcattctttc ttgaggaggg     120
cagcaaacgg gaagag                                                     136

<210> SEQ ID NO 78
<211> LENGTH: 137
<212> TYPE: DNA
<213> ORGANISM: Artificial Sequence
<220> FEATURE:
<223> OTHER INFORMATION: Synthetic probe

<400> SEQUENCE: 78
gaggagggca gcaaacggga agagtcttcc tttacgatat tcagtaaaag ggccttctgg      60
accttctgag tatagcatgc agtaaatcca tgtccaatat agcattcttt cttgaggagg     120
gcagcaaacg ggaagag                                                    137

<210> SEQ ID NO 79
<211> LENGTH: 135
<212> TYPE: DNA
<213> ORGANISM: Artificial Sequence
<220> FEATURE:
<223> OTHER INFORMATION: Synthetic probe

<400> SEQUENCE: 79
gaggagggca gcaaacggga agagtcttcc tttacgatat tctcctgggc gaagtaagtc      60
ttggtaggat tggggctcag ttgctctggg aaggatatag cattctttct tgaggagggc     120
agcaaacggg aagag                                                      135

<210> SEQ ID NO 80
<211> LENGTH: 131
<212> TYPE: DNA
<213> ORGANISM: Artificial Sequence
<220> FEATURE:
<223> OTHER INFORMATION: Synthetic probe

<400> SEQUENCE: 80
gaggagggca gcaaacggga agagtcttcc tttacgatat tacactgaag agtatcagga      60
atgccaggaa ctgaggcttg cttctggctt atatagcatt cttcttgag gagggcagca     120 aacgggaaga g                                                          131

<210> SEQ ID NO 81
<211> LENGTH: 132
<212> TYPE: DNA
<213> ORGANISM: Artificial Sequence
<220> FEATURE:
<223> OTHER INFORMATION: Synthetic probe

<400> SEQUENCE: 81
gaggagggca gcaaacggga agagtcttcc tttacgatat tattttctgc taagggattc      60
tgcaagatgt cagagtctgc ttttaaagag aatatagcat tctttcttga ggagggcagc     120
aaacgggaag ag                                                         132

<210> SEQ ID NO 82
<211> LENGTH: 137
<212> TYPE: DNA
<213> ORGANISM: Artificial Sequence
<220> FEATURE:
<223> OTHER INFORMATION: Synthetic probe

<400> SEQUENCE: 82
gaggagggca gcaaacggga agagtcttcc tttacgatat tagaaatctg acccagaagt      60
ctgctgtaat cgctggtgaa aactccatca gcatgcatat agcattcttt cttgaggagg     120
gcagcaaacg ggaagag                                                    137

<210> SEQ ID NO 83
<211> LENGTH: 127
<212> TYPE: DNA
<213> ORGANISM: Artificial Sequence
<220> FEATURE:
<223> OTHER INFORMATION: Synthetic probe

<400> SEQUENCE: 83
gaggagggca gcaaacggga agagtcttcc tttacgatat tctcactgct cctctttcca      60
ttcaggatgg agttcaggta tttcttatat agcattcttt cttgaggagg gcagcaaacg     120
ggaagag                                                               127

<210> SEQ ID NO 84
<211> LENGTH: 133
<212> TYPE: DNA
<213> ORGANISM: Artificial Sequence
<220> FEATURE:
<223> OTHER INFORMATION: Synthetic probe

<400> SEQUENCE: 84
gaggagggca gcaaacggga agagtcttcc tttacgatat tgtgtcgttt gattggcaca      60
ggatcttccg agatgctgct gctgattcgt ttatatagca ttctttcttg aggagggcag     120

```
caaacgggaa gag                                                          133

<210> SEQ ID NO 85
<211> LENGTH: 137
<212> TYPE: DNA
<213> ORGANISM: Artificial Sequence
<220> FEATURE:
<223> OTHER INFORMATION: Synthetic probe

<400> SEQUENCE: 85
gaggagggca gcaaacggga agagtcttcc tttacgatat tcgtcgctga gcggcgggtg      60
ctctgctctg ggtgcctctg tgagagaaga gatccaatat agcattcttt cttgaggagg     120
gcagcaaacg ggaagag                                                    137

<210> SEQ ID NO 86
<211> LENGTH: 135
<212> TYPE: DNA
<213> ORGANISM: Artificial Sequence
<220> FEATURE:
<223> OTHER INFORMATION: Synthetic probe

<400> SEQUENCE: 86
gaggagggca gcaaacggga agagtcttcc tttacgatat ttggaggggt accccctcagc     60 cagaatgccc aaacacacga gcagagatag agcgatatag cattctttct tgaggagggc    120
agcaaacggg aagag                                                      135

<210> SEQ ID NO 87
<211> LENGTH: 133
<212> TYPE: DNA
<213> ORGANISM: Artificial Sequence
<220> FEATURE:
<223> OTHER INFORMATION: Synthetic probe

<400> SEQUENCE: 87
gaggagggca gcaaacggga agagtcttcc tttacgatat tatgagattg atgtagtgtc      60
gcagagcgga gtagtatctg gccatgtcct ctatatagca ttctttcttg aggagggcag    120
caaacgggaa gag                                                        133

<210> SEQ ID NO 88
<211> LENGTH: 133
<212> TYPE: DNA
<213> ORGANISM: Artificial Sequence
<220> FEATURE:
<223> OTHER INFORMATION: Synthetic probe

<400> SEQUENCE: 88
gaggagggca gcaaacggga agagtcttcc tttacgatat tggggatgag atgagatgag      60
ggtggaaact tggaaaagtc gggagaacaa gtatatagca ttctttcttg aggagggcag    120
caaacgggaa gag                                                        133

<210> SEQ ID NO 89
<211> LENGTH: 134
<212> TYPE: DNA
<213> ORGANISM: Artificial Sequence
<220> FEATURE:
<223> OTHER INFORMATION: Synthetic probe

<400> SEQUENCE: 89
gaggagggca gcaaacggga agagtcttcc tttacgatat tgcggagtcc agcctagtgg      60
tggcatgcat tggtgggaca ggcagactgg tttatatagc attctttctt gaggagggca    120
```

```
gcaaacggga agag                                                       134

<210> SEQ ID NO 90
<211> LENGTH: 134
<212> TYPE: DNA
<213> ORGANISM: Artificial Sequence
<220> FEATURE:
<223> OTHER INFORMATION: Synthetic probe

<400> SEQUENCE: 90
gaggagggca gcaaacggga agagtcttcc tttacgatat taacgtacat gcgccagtcg    60
aaggattttt ataacggccg tcaacttaac ctaatatagc attctttctt gaggagggca   120
gcaaacggga agag                                                      134

<210> SEQ ID NO 91
<211> LENGTH: 137
<212> TYPE: DNA
<213> ORGANISM: Artificial Sequence
<220> FEATURE:
<223> OTHER INFORMATION: Synthetic probe

<400> SEQUENCE: 91
gaggagggca gcaaacggga agagtcttcc tttacgatat tggctctacc attcattccc    60
ctctgagcgg ttaaagacaa cttgccatct accattatat agcattcttt cttgaggagg   120
gcagcaaacg ggaagag                                                   137

<210> SEQ ID NO 92
<211> LENGTH: 134
<212> TYPE: DNA
<213> ORGANISM: Artificial Sequence
<220> FEATURE:
<223> OTHER INFORMATION: Synthetic probe

<400> SEQUENCE: 92
gaggagggca gcaaacggga agagtcttcc tttacgatat tacacactgg gttagagaag    60
gcgtgtactg ctatgctgtt ggcacgacac cttatatagc attctttctt gaggagggca   120
gcaaacggga agag                                                      134

<210> SEQ ID NO 93
<211> LENGTH: 132
<212> TYPE: DNA
<213> ORGANISM: Artificial Sequence
<220> FEATURE:
<223> OTHER INFORMATION: Synthetic probe

<400> SEQUENCE: 93
gaggagggca gcaaacggga agagtcttcc tttacgatat taagtgtctt accctagatg    60
tttagccatg gtcaaattag acccctgact tatatagcat tctttcttga ggagggcagc   120
aaacgggaag ag                                                        132

<210> SEQ ID NO 94
<211> LENGTH: 130
<212> TYPE: DNA
<213> ORGANISM: Artificial Sequence
<220> FEATURE:
<223> OTHER INFORMATION: Synthetic probe

<400> SEQUENCE: 94
gaggagggca gcaaacggga agagtcttcc tttacgatat taaccgatat gcaacgtgac    60
```

```
ctcaaggatc cagctactgg ctgcatcaaa tatagcattc tttcttgagg agggcagcaa      120
acgggaagag                                                            130
```

<210> SEQ ID NO 95
<211> LENGTH: 61
<212> TYPE: DNA
<213> ORGANISM: Artificial Sequence
<220> FEATURE:
<223> OTHER INFORMATION: Synthetic probe

<400> SEQUENCE: 95

```
gaggagggca gcaaacggga agagtcttcc tttacgatat tcattggata tttgtccagg      60
c                                                                     61
```

<210> SEQ ID NO 96
<211> LENGTH: 61
<212> TYPE: DNA
<213> ORGANISM: Artificial Sequence
<220> FEATURE:
<223> OTHER INFORMATION: Synthetic probe

<400> SEQUENCE: 96

```
gaggagggca gcaaacggga agagtcttcc tttacgatat tttgtactgg gaactgcgga      60
g                                                                     61
```

<210> SEQ ID NO 97
<211> LENGTH: 61
<212> TYPE: DNA
<213> ORGANISM: Artificial Sequence
<220> FEATURE:
<223> OTHER INFORMATION: Synthetic probe

<400> SEQUENCE: 97

```
gaggagggca gcaaacggga agagtcttcc tttacgatat tgtagagtgt ggcgcttcat      60
c                                                                     61
```

<210> SEQ ID NO 98
<211> LENGTH: 61
<212> TYPE: DNA
<213> ORGANISM: Artificial Sequence
<220> FEATURE:
<223> OTHER INFORMATION: Synthetic probe

<400> SEQUENCE: 98

```
gaggagggca gcaaacggga agagtcttcc tttacgatat tgcatagcca atgacagaca      60
g                                                                     61
```

<210> SEQ ID NO 99
<211> LENGTH: 61
<212> TYPE: DNA
<213> ORGANISM: Artificial Sequence
<220> FEATURE:
<223> OTHER INFORMATION: Synthetic probe

<400> SEQUENCE: 99

```
gaggagggca gcaaacggga agagtcttcc tttacgatat tgggaaaacg ccagatgttg      60
c                                                                     61
```

<210> SEQ ID NO 100
<211> LENGTH: 61
<212> TYPE: DNA
<213> ORGANISM: Artificial Sequence

```
<220> FEATURE:
<223> OTHER INFORMATION: Synthetic probe

<400> SEQUENCE: 100
gaggagggca gcaaacggga agagtcttcc tttacgatat tcaccattct ggtagcatat    60
g                                                                    61

<210> SEQ ID NO 101
<211> LENGTH: 61
<212> TYPE: DNA
<213> ORGANISM: Artificial Sequence
<220> FEATURE:
<223> OTHER INFORMATION: Synthetic probe

<400> SEQUENCE: 101
gaggagggca gcaaacggga agagtcttcc tttacgatat taaagatggc catgatggtg    60
t                                                                    61

<210> SEQ ID NO 102
<211> LENGTH: 61
<212> TYPE: DNA
<213> ORGANISM: Artificial Sequence
<220> FEATURE:
<223> OTHER INFORMATION: Synthetic probe

<400> SEQUENCE: 102
gaggagggca gcaaacggga agagtcttcc tttacgatat tgagctccat gtagaagagt    60
g                                                                    61

<210> SEQ ID NO 103
<211> LENGTH: 61
<212> TYPE: DNA
<213> ORGANISM: Artificial Sequence
<220> FEATURE:
<223> OTHER INFORMATION: Synthetic probe

<400> SEQUENCE: 103
gaggagggca gcaaacggga agagtcttcc tttacgatat ttagaaatgc acccatttcg    60
g                                                                    61

<210> SEQ ID NO 104
<211> LENGTH: 61
<212> TYPE: DNA
<213> ORGANISM: Artificial Sequence
<220> FEATURE:
<223> OTHER INFORMATION: Synthetic probe

<400> SEQUENCE: 104
gaggagggca gcaaacggga agagtcttcc tttacgatat taaatcgggc agatcttctt    60
c                                                                    61

<210> SEQ ID NO 105
<211> LENGTH: 61
<212> TYPE: DNA
<213> ORGANISM: Artificial Sequence
<220> FEATURE:
<223> OTHER INFORMATION: Synthetic probe

<400> SEQUENCE: 105
gaggagggca gcaaacggga agagtcttcc tttacgatat tgtgttatag taggaggcga    60
t                                                                    61
```

<210> SEQ ID NO 106
<211> LENGTH: 61
<212> TYPE: DNA
<213> ORGANISM: Artificial Sequence
<220> FEATURE:
<223> OTHER INFORMATION: Synthetic probe

<400> SEQUENCE: 106
gaggagggca gcaaacggga agagtcttcc tttacgatat tcgtgaagga ggagatgagg    60
t                                                                   61

<210> SEQ ID NO 107
<211> LENGTH: 61
<212> TYPE: DNA
<213> ORGANISM: Artificial Sequence
<220> FEATURE:
<223> OTHER INFORMATION: Synthetic probe

<400> SEQUENCE: 107
gaggagggca gcaaacggga agagtcttcc tttacgatat ttgttccaag agttcttgca    60
g                                                                   61

<210> SEQ ID NO 108
<211> LENGTH: 61
<212> TYPE: DNA
<213> ORGANISM: Artificial Sequence
<220> FEATURE:
<223> OTHER INFORMATION: Synthetic probe

<400> SEQUENCE: 108
gaggagggca gcaaacggga agagtcttcc tttacgatat tcgaagtagt tggtgcagtt    60
g                                                                   61

<210> SEQ ID NO 109
<211> LENGTH: 61
<212> TYPE: DNA
<213> ORGANISM: Artificial Sequence
<220> FEATURE:
<223> OTHER INFORMATION: Synthetic probe

<400> SEQUENCE: 109
gaggagggca gcaaacggga agagtcttcc tttacgatat taggtgacgt ggaatggagt    60
g                                                                   61

<210> SEQ ID NO 110
<211> LENGTH: 61
<212> TYPE: DNA
<213> ORGANISM: Artificial Sequence
<220> FEATURE:
<223> OTHER INFORMATION: Synthetic probe

<400> SEQUENCE: 110
gaggagggca gcaaacggga agagtcttcc tttacgatat tatggcgcaa gtaaaactcc    60
t                                                                   61

<210> SEQ ID NO 111
<211> LENGTH: 61
<212> TYPE: DNA
<213> ORGANISM: Artificial Sequence
<220> FEATURE:
<223> OTHER INFORMATION: Synthetic probe

<400> SEQUENCE: 111
gaggagggca gcaaacggga agagtcttcc tttacgatat tctttgactg atggatctgc    60
a    61

<210> SEQ ID NO 112
<211> LENGTH: 61
<212> TYPE: DNA
<213> ORGANISM: Artificial Sequence
<220> FEATURE:
<223> OTHER INFORMATION: Synthetic probe

<400> SEQUENCE: 112
gaggagggca gcaaacggga agagtcttcc tttacgatat tatgagcatg atgcagagag    60
c    61

<210> SEQ ID NO 113
<211> LENGTH: 61
<212> TYPE: DNA
<213> ORGANISM: Artificial Sequence
<220> FEATURE:
<223> OTHER INFORMATION: Synthetic probe

<400> SEQUENCE: 113
gaggagggca gcaaacggga agagtcttcc tttacgatat tttccagatg ctgaagtaga    60
t    61

<210> SEQ ID NO 114
<211> LENGTH: 61
<212> TYPE: DNA
<213> ORGANISM: Artificial Sequence
<220> FEATURE:
<223> OTHER INFORMATION: Synthetic probe

<400> SEQUENCE: 114
gaggagggca gcaaacggga agagtcttcc tttacgatat tcttgccaga cgttttgact    60
c    61

<210> SEQ ID NO 115
<211> LENGTH: 61
<212> TYPE: DNA
<213> ORGANISM: Artificial Sequence
<220> FEATURE:
<223> OTHER INFORMATION: Synthetic probe

<400> SEQUENCE: 115
gaggagggca gcaaacggga agagtcttcc tttacgatat tgccagttgg gtttcaagta    60
a    61

<210> SEQ ID NO 116
<211> LENGTH: 61
<212> TYPE: DNA
<213> ORGANISM: Artificial Sequence
<220> FEATURE:
<223> OTHER INFORMATION: Synthetic probe

<400> SEQUENCE: 116
gaggagggca gcaaacggga agagtcttcc tttacgatat tctagcaaac gccaggagaa    60
c    61

<210> SEQ ID NO 117
<211> LENGTH: 61
<212> TYPE: DNA

```
<213> ORGANISM: Artificial Sequence
<220> FEATURE:
<223> OTHER INFORMATION: Synthetic probe

<400> SEQUENCE: 117
gaggagggca gcaaacggga agagtcttcc tttacgatat tgcatcttgg taacagttgt    60
t                                                                    61

<210> SEQ ID NO 118
<211> LENGTH: 61
<212> TYPE: DNA
<213> ORGANISM: Artificial Sequence
<220> FEATURE:
<223> OTHER INFORMATION: Synthetic probe

<400> SEQUENCE: 118
gaggagggca gcaaacggga agagtcttcc tttacgatat ttcatgcagt tcaccacact    60
g                                                                    61

<210> SEQ ID NO 119
<211> LENGTH: 61
<212> TYPE: DNA
<213> ORGANISM: Artificial Sequence
<220> FEATURE:
<223> OTHER INFORMATION: Synthetic probe

<400> SEQUENCE: 119
gaggagggca gcaaacggga agagtcttcc tttacgatat tacaaagcca gagacgaagc    60
t                                                                    61

<210> SEQ ID NO 120
<211> LENGTH: 61
<212> TYPE: DNA
<213> ORGANISM: Artificial Sequence
<220> FEATURE:
<223> OTHER INFORMATION: Synthetic probe

<400> SEQUENCE: 120
gaggagggca gcaaacggga agagtcttcc tttacgatat tatgtagcca agcaccgtga    60
a                                                                    61

<210> SEQ ID NO 121
<211> LENGTH: 61
<212> TYPE: DNA
<213> ORGANISM: Artificial Sequence
<220> FEATURE:
<223> OTHER INFORMATION: Synthetic probe

<400> SEQUENCE: 121
gaggagggca gcaaacggga agagtcttcc tttacgatat tacacgtctt cgttcctcat    60
c                                                                    61

<210> SEQ ID NO 122
<211> LENGTH: 61
<212> TYPE: DNA
<213> ORGANISM: Artificial Sequence
<220> FEATURE:
<223> OTHER INFORMATION: Synthetic probe

<400> SEQUENCE: 122
gaggagggca gcaaacggga agagtcttcc tttacgatat tcctccgcat atgtgatgaa    60
a                                                                    61
```

<210> SEQ ID NO 123
<211> LENGTH: 61
<212> TYPE: DNA
<213> ORGANISM: Artificial Sequence
<220> FEATURE:
<223> OTHER INFORMATION: Synthetic probe

<400> SEQUENCE: 123
gaggagggca gcaaacggga agagtcttcc tttacgatat tgcgaacgta ctatccaaac    60
c                                                                   61

<210> SEQ ID NO 124
<211> LENGTH: 61
<212> TYPE: DNA
<213> ORGANISM: Artificial Sequence
<220> FEATURE:
<223> OTHER INFORMATION: Synthetic probe

<400> SEQUENCE: 124
gaggagggca gcaaacggga agagtcttcc tttacgatat tcaacacagc tgtgatcaca    60
c                                                                   61

<210> SEQ ID NO 125
<211> LENGTH: 61
<212> TYPE: DNA
<213> ORGANISM: Artificial Sequence
<220> FEATURE:
<223> OTHER INFORMATION: Synthetic probe

<400> SEQUENCE: 125
gaggagggca gcaaacggga agagtcttcc tttacgatat tcccagatgt gaggaaactc    60
a                                                                   61

<210> SEQ ID NO 126
<211> LENGTH: 61
<212> TYPE: DNA
<213> ORGANISM: Artificial Sequence
<220> FEATURE:
<223> OTHER INFORMATION: Synthetic probe

<400> SEQUENCE: 126
gaggagggca gcaaacggga agagtcttcc tttacgatat tcgatgagca caaccattc    60 c                                                                   61

<210> SEQ ID NO 127
<211> LENGTH: 61
<212> TYPE: DNA
<213> ORGANISM: Artificial Sequence
<220> FEATURE:
<223> OTHER INFORMATION: Synthetic probe

<400> SEQUENCE: 127
gaggagggca gcaaacggga agagtcttcc tttacgatat tcccaagatg caagtgatga    60
c                                                                   61

<210> SEQ ID NO 128
<211> LENGTH: 61
<212> TYPE: DNA
<213> ORGANISM: Artificial Sequence
<220> FEATURE:
<223> OTHER INFORMATION: Synthetic probe

```
<400> SEQUENCE: 128
gaggagggca gcaaacggga agagtcttcc tttacgatat tctgatgtca gtgtgagcag    60
g                                                                    61

<210> SEQ ID NO 129
<211> LENGTH: 61
<212> TYPE: DNA
<213> ORGANISM: Artificial Sequence
<220> FEATURE:
<223> OTHER INFORMATION: Synthetic probe

<400> SEQUENCE: 129
gaggagggca gcaaacggga agagtcttcc tttacgatat ttcgatgaga gccacggtga    60
g                                                                    61

<210> SEQ ID NO 130
<211> LENGTH: 61
<212> TYPE: DNA
<213> ORGANISM: Artificial Sequence
<220> FEATURE:
<223> OTHER INFORMATION: Synthetic probe

<400> SEQUENCE: 130
gaggagggca gcaaacggga agagtcttcc tttacgatat tgaaccaaga cacgacgacg    60
g                                                                    61

<210> SEQ ID NO 131
<211> LENGTH: 61
<212> TYPE: DNA
<213> ORGANISM: Artificial Sequence
<220> FEATURE:
<223> OTHER INFORMATION: Synthetic probe

<400> SEQUENCE: 131
gaggagggca gcaaacggga agagtcttcc tttacgatat ttgcagaact gagtgattcc    60
a                                                                    61

<210> SEQ ID NO 132
<211> LENGTH: 61
<212> TYPE: DNA
<213> ORGANISM: Artificial Sequence
<220> FEATURE:
<223> OTHER INFORMATION: Synthetic probe

<400> SEQUENCE: 132
gaggagggca gcaaacggga agagtcttcc tttacgatat taaaaccatc cggggctgaa    60
g                                                                    61

<210> SEQ ID NO 133
<211> LENGTH: 61
<212> TYPE: DNA
<213> ORGANISM: Artificial Sequence
<220> FEATURE:
<223> OTHER INFORMATION: Synthetic probe

<400> SEQUENCE: 133
gaggagggca gcaaacggga agagtcttcc tttacgatat tcaggagaaa cagagggctg    60
a                                                                    61

<210> SEQ ID NO 134
<211> LENGTH: 61
```

```
<212> TYPE: DNA
<213> ORGANISM: Artificial Sequence
<220> FEATURE:
<223> OTHER INFORMATION: Synthetic probe

<400> SEQUENCE: 134
gaggagggca gcaaacggga agagtcttcc tttacgatat tgttggggtg gactcatcaa    60
a                                                                    61

<210> SEQ ID NO 135
<211> LENGTH: 61
<212> TYPE: DNA
<213> ORGANISM: Artificial Sequence
<220> FEATURE:
<223> OTHER INFORMATION: Synthetic probe

<400> SEQUENCE: 135
gaggagggca gcaaacggga agagtcttcc tttacgatat tctccagtgg ggataattgt    60
a                                                                    61

<210> SEQ ID NO 136
<211> LENGTH: 61
<212> TYPE: DNA
<213> ORGANISM: Artificial Sequence
<220> FEATURE:
<223> OTHER INFORMATION: Synthetic probe

<400> SEQUENCE: 136
gaggagggca gcaaacggga agagtcttcc tttacgatat ttatgcagta gcccaagatg    60
a                                                                    61

<210> SEQ ID NO 137
<211> LENGTH: 61
<212> TYPE: DNA
<213> ORGANISM: Artificial Sequence
<220> FEATURE:
<223> OTHER INFORMATION: Synthetic probe

<400> SEQUENCE: 137
gaggagggca gcaaacggga agagtcttcc tttacgatat tagggatgca gatgacagac    60
g                                                                    61

<210> SEQ ID NO 138
<211> LENGTH: 61
<212> TYPE: DNA
<213> ORGANISM: Artificial Sequence
<220> FEATURE:
<223> OTHER INFORMATION: Synthetic probe

<400> SEQUENCE: 138
gaggagggca gcaaacggga agagtcttcc tttacgatat tgtgctgatc agccgataaa    60
t                                                                    61

<210> SEQ ID NO 139
<211> LENGTH: 61
<212> TYPE: DNA
<213> ORGANISM: Artificial Sequence
<220> FEATURE:
<223> OTHER INFORMATION: Synthetic probe

<400> SEQUENCE: 139
gaggagggca gcaaacggga agagtcttcc tttacgatat tataatgcgc tccttaagtg    60
```

<210> SEQ ID NO 140
<211> LENGTH: 61
<212> TYPE: DNA
<213> ORGANISM: Artificial Sequence
<220> FEATURE:
<223> OTHER INFORMATION: Synthetic probe

<400> SEQUENCE: 140
gaggagggca gcaaacggga agagtcttcc tttacgatat tggtgtttca ggagtgatac    60
t                                                                   61

<210> SEQ ID NO 141
<211> LENGTH: 61
<212> TYPE: DNA
<213> ORGANISM: Artificial Sequence
<220> FEATURE:
<223> OTHER INFORMATION: Synthetic probe

<400> SEQUENCE: 141
gaggagggca gcaaacggga agagtcttcc tttacgatat tatgtcccca cacggaattt    60
c                                                                   61

<210> SEQ ID NO 142
<211> LENGTH: 61
<212> TYPE: DNA
<213> ORGANISM: Artificial Sequence
<220> FEATURE:
<223> OTHER INFORMATION: Synthetic probe

<400> SEQUENCE: 142
gaggagggca gcaaacggga agagtcttcc tttacgatat tagatcatca tcgtaccagg    60
a                                                                   61

<210> SEQ ID NO 143
<211> LENGTH: 61
<212> TYPE: DNA
<213> ORGANISM: Artificial Sequence
<220> FEATURE:
<223> OTHER INFORMATION: Synthetic probe

<400> SEQUENCE: 143
gaggagggca gcaaacggga agagtcttcc tttacgatat ttggcatagt agttgtagtg    60
g                                                                   61

<210> SEQ ID NO 144
<211> LENGTH: 61
<212> TYPE: DNA
<213> ORGANISM: Artificial Sequence
<220> FEATURE:
<223> OTHER INFORMATION: Synthetic probe

<400> SEQUENCE: 144
gaggagggca gcaaacggga agagtcttcc tttacgatat taagatgagg agggtgagca    60
g                                                                   61

<210> SEQ ID NO 145
<211> LENGTH: 61
<212> TYPE: DNA
<213> ORGANISM: Artificial Sequence
<220> FEATURE:
<223> OTHER INFORMATION: Synthetic probe -continued

<400> SEQUENCE: 145
gaggagggca gcaaacggga agagtcttcc tttacgatat tgcacattgc caaagacgat    60
g                                                                   61

<210> SEQ ID NO 146
<211> LENGTH: 61
<212> TYPE: DNA
<213> ORGANISM: Artificial Sequence
<220> FEATURE:
<223> OTHER INFORMATION: Synthetic probe

<400> SEQUENCE: 146
gaggagggca gcaaacggga agagtcttcc tttacgatat ttctctctgg atacagccat    60
g                                                                   61

<210> SEQ ID NO 147
<211> LENGTH: 61
<212> TYPE: DNA
<213> ORGANISM: Artificial Sequence
<220> FEATURE:
<223> OTHER INFORMATION: Synthetic probe

<400> SEQUENCE: 147
gaggagggca gcaaacggga agagtcttcc tttacgatat tgttggtggt ggtctgcaaa    60
g                                                                   61

<210> SEQ ID NO 148
<211> LENGTH: 61
<212> TYPE: DNA
<213> ORGANISM: Artificial Sequence
<220> FEATURE:
<223> OTHER INFORMATION: Synthetic probe

<400> SEQUENCE: 148
gaggagggca gcaaacggga agagtcttcc tttacgatat tacagcgagg ctgactatca    60
g                                                                   61

<210> SEQ ID NO 149
<211> LENGTH: 61
<212> TYPE: DNA
<213> ORGANISM: Artificial Sequence
<220> FEATURE:
<223> OTHER INFORMATION: Synthetic probe

<400> SEQUENCE: 149
gaggagggca gcaaacggga agagtcttcc tttacgatat tagtgtggcc accagaagat    60
c                                                                   61

<210> SEQ ID NO 150
<211> LENGTH: 61
<212> TYPE: DNA
<213> ORGANISM: Artificial Sequence
<220> FEATURE:
<223> OTHER INFORMATION: Synthetic probe

<400> SEQUENCE: 150
gaggagggca gcaaacggga agagtcttcc tttacgatat tatagacgac ccagggcata    60
a                                                                   61

<210> SEQ ID NO 151

```
<211> LENGTH: 61
<212> TYPE: DNA
<213> ORGANISM: Artificial Sequence
<220> FEATURE:
<223> OTHER INFORMATION: Synthetic probe

<400> SEQUENCE: 151
gaggagggca gcaaacggga agagtcttcc tttacgatat tctgctgaat ttccactcac      60
c                                                                     61

<210> SEQ ID NO 152
<211> LENGTH: 61
<212> TYPE: DNA
<213> ORGANISM: Artificial Sequence
<220> FEATURE:
<223> OTHER INFORMATION: Synthetic probe

<400> SEQUENCE: 152
gaggagggca gcaaacggga agagtcttcc tttacgatat tgtgacaaag atgtcacagt      60
g                                                                     61

<210> SEQ ID NO 153
<211> LENGTH: 61
<212> TYPE: DNA
<213> ORGANISM: Artificial Sequence
<220> FEATURE:
<223> OTHER INFORMATION: Synthetic probe

<400> SEQUENCE: 153
gaggagggca gcaaacggga agagtcttcc tttacgatat ttgtgcacat catgacatcc      60
a                                                                     61

<210> SEQ ID NO 154
<211> LENGTH: 61
<212> TYPE: DNA
<213> ORGANISM: Artificial Sequence
<220> FEATURE:
<223> OTHER INFORMATION: Synthetic probe

<400> SEQUENCE: 154
gaggagggca gcaaacggga agagtcttcc tttacgatat tcaacatagg catggccaca      60
g                                                                     61

<210> SEQ ID NO 155
<211> LENGTH: 61
<212> TYPE: DNA
<213> ORGANISM: Artificial Sequence
<220> FEATURE:
<223> OTHER INFORMATION: Synthetic probe

<400> SEQUENCE: 155
gaggagggca gcaaacggga agagtcttcc tttacgatat ttggagctgt agcgtgtgtt      60
a                                                                     61

<210> SEQ ID NO 156
<211> LENGTH: 61
<212> TYPE: DNA
<213> ORGANISM: Artificial Sequence
<220> FEATURE:
<223> OTHER INFORMATION: Synthetic probe

<400> SEQUENCE: 156
gaggagggca gcaaacggga agagtcttcc tttacgatat tatcatgaca gtaactcggc      60
``` g                                                              61

<210> SEQ ID NO 157
<211> LENGTH: 61
<212> TYPE: DNA
<213> ORGANISM: Artificial Sequence
<220> FEATURE:
<223> OTHER INFORMATION: Synthetic probe

<400> SEQUENCE: 157
gaggagggca gcaaacggga agagtcttcc tttacgatat taaggacagg acccagacaa    60
t                                                              61

<210> SEQ ID NO 158
<211> LENGTH: 61
<212> TYPE: DNA
<213> ORGANISM: Artificial Sequence
<220> FEATURE:
<223> OTHER INFORMATION: Synthetic probe

<400> SEQUENCE: 158
gaggagggca gcaaacggga agagtcttcc tttacgatat taagagcagt gggcaagaga    60
t                                                              61

<210> SEQ ID NO 159
<211> LENGTH: 61
<212> TYPE: DNA
<213> ORGANISM: Artificial Sequence
<220> FEATURE:
<223> OTHER INFORMATION: Synthetic probe

<400> SEQUENCE: 159
gaggagggca gcaaacggga agagtcttcc tttacgatat tttctggtct gtgttgttga    60
g                                                              61

<210> SEQ ID NO 160
<211> LENGTH: 61
<212> TYPE: DNA
<213> ORGANISM: Artificial Sequence
<220> FEATURE:
<223> OTHER INFORMATION: Synthetic probe

<400> SEQUENCE: 160
gaggagggca gcaaacggga agagtcttcc tttacgatat tagggttggc aatgatacac    60
t                                                              61

<210> SEQ ID NO 161
<211> LENGTH: 61
<212> TYPE: DNA
<213> ORGANISM: Artificial Sequence
<220> FEATURE:
<223> OTHER INFORMATION: Synthetic probe

<400> SEQUENCE: 161
gaggagggca gcaaacggga agagtcttcc tttacgatat ttggaggagt agaccacgaa    60
g                                                              61

<210> SEQ ID NO 162
<211> LENGTH: 61
<212> TYPE: DNA
<213> ORGANISM: Artificial Sequence
<220> FEATURE:

<223> OTHER INFORMATION: Synthetic probe

<400> SEQUENCE: 162
gaggagggca gcaaacggga agagtcttcc tttacgatat tgaagggcac gtagaacgag    60
a    61

<210> SEQ ID NO 163
<211> LENGTH: 61
<212> TYPE: DNA
<213> ORGANISM: Artificial Sequence
<220> FEATURE:
<223> OTHER INFORMATION: Synthetic probe

<400> SEQUENCE: 163
gaggagggca gcaaacggga agagtcttcc tttacgatat ttttgatata gaccagcagg    60
g    61

<210> SEQ ID NO 164
<211> LENGTH: 61
<212> TYPE: DNA
<213> ORGANISM: Artificial Sequence
<220> FEATURE:
<223> OTHER INFORMATION: Synthetic probe

<400> SEQUENCE: 164
gaggagggca gcaaacggga agagtcttcc tttacgatat tgcttgcgga gaacgatgta    60
g    61

<210> SEQ ID NO 165
<211> LENGTH: 61
<212> TYPE: DNA
<213> ORGANISM: Artificial Sequence
<220> FEATURE:
<223> OTHER INFORMATION: Synthetic probe

<400> SEQUENCE: 165
gaggagggca gcaaacggga agagtcttcc tttacgatat ttctgaaagc tcggctgcta    60
c    61

<210> SEQ ID NO 166
<211> LENGTH: 61
<212> TYPE: DNA
<213> ORGANISM: Artificial Sequence
<220> FEATURE:
<223> OTHER INFORMATION: Synthetic probe

<400> SEQUENCE: 166
gaggagggca gcaaacggga agagtcttcc tttacgatat ttgagtggtg tcttcaggtt    60
g    61

<210> SEQ ID NO 167
<211> LENGTH: 61
<212> TYPE: DNA
<213> ORGANISM: Artificial Sequence
<220> FEATURE:
<223> OTHER INFORMATION: Synthetic probe

<400> SEQUENCE: 167
gaggagggca gcaaacggga agagtcttcc tttacgatat tagtttcatg tcctcagggt    60
g    61

<210> SEQ ID NO 168
<211> LENGTH: 61
<212> TYPE: DNA
<213> ORGANISM: Artificial Sequence
<220> FEATURE:
<223> OTHER INFORMATION: Synthetic probe

<400> SEQUENCE: 168
gaggagggca gcaaacggga agagtcttcc tttacgatat tagacttcat gataacggtg    60
c                                                                    61

<210> SEQ ID NO 169
<211> LENGTH: 61
<212> TYPE: DNA
<213> ORGANISM: Artificial Sequence
<220> FEATURE:
<223> OTHER INFORMATION: Synthetic probe

<400> SEQUENCE: 169
gaggagggca gcaaacggga agagtcttcc tttacgatat ttgttcactg ggaaactccc    60
a                                                                    61

<210> SEQ ID NO 170
<211> LENGTH: 61
<212> TYPE: DNA
<213> ORGANISM: Artificial Sequence
<220> FEATURE:
<223> OTHER INFORMATION: Synthetic probe

<400> SEQUENCE: 170
gaggagggca gcaaacggga agagtcttcc tttacgatat ttgggaggga tggggctata    60
c                                                                    61

<210> SEQ ID NO 171
<211> LENGTH: 61
<212> TYPE: DNA
<213> ORGANISM: Artificial Sequence
<220> FEATURE:
<223> OTHER INFORMATION: Synthetic probe

<400> SEQUENCE: 171
gaggagggca gcaaacggga agagtcttcc tttacgatat tgatggatcg gggagagtga    60
g                                                                    61

<210> SEQ ID NO 172
<211> LENGTH: 61
<212> TYPE: DNA
<213> ORGANISM: Artificial Sequence
<220> FEATURE:
<223> OTHER INFORMATION: Synthetic probe

<400> SEQUENCE: 172
gaggagggca gcaaacggga agagtcttcc tttacgatat tttgacaatc ttggcatgcc    60
c                                                                    61

<210> SEQ ID NO 173
<211> LENGTH: 61
<212> TYPE: DNA
<213> ORGANISM: Artificial Sequence
<220> FEATURE:
<223> OTHER INFORMATION: Synthetic probe

<400> SEQUENCE: 173

```
gaggagggca gcaaacggga agagtcttcc tttacgatat taaagaactt ggcaatcctg    60
g                                                                    61

<210> SEQ ID NO 174
<211> LENGTH: 61
<212> TYPE: DNA
<213> ORGANISM: Artificial Sequence
<220> FEATURE:
<223> OTHER INFORMATION: Synthetic probe

<400> SEQUENCE: 174
gaggagggca gcaaacggga agagtcttcc tttacgatat tcattgggca tggtctggat    60
c                                                                    61

<210> SEQ ID NO 175
<211> LENGTH: 61
<212> TYPE: DNA
<213> ORGANISM: Artificial Sequence
<220> FEATURE:
<223> OTHER INFORMATION: Synthetic probe

<400> SEQUENCE: 175
gaggagggca gcaaacggga agagtcttcc tttacgatat ttcatcgtct taagggaggt    60
c                                                                    61

<210> SEQ ID NO 176
<211> LENGTH: 61
<212> TYPE: DNA
<213> ORGANISM: Artificial Sequence
<220> FEATURE:
<223> OTHER INFORMATION: Synthetic probe

<400> SEQUENCE: 176
gaggagggca gcaaacggga agagtcttcc tttacgatat taatggcaag catctgagtg    60
g                                                                    61

<210> SEQ ID NO 177
<211> LENGTH: 61
<212> TYPE: DNA
<213> ORGANISM: Artificial Sequence
<220> FEATURE:
<223> OTHER INFORMATION: Synthetic probe

<400> SEQUENCE: 177
gaggagggca gcaaacggga agagtcttcc tttacgatat tagccagcag atgatgaaca    60
c                                                                    61

<210> SEQ ID NO 178
<211> LENGTH: 61
<212> TYPE: DNA
<213> ORGANISM: Artificial Sequence
<220> FEATURE:
<223> OTHER INFORMATION: Synthetic probe

<400> SEQUENCE: 178
gaggagggca gcaaacggga agagtcttcc tttacgatat tcaggatgtg cgtgatgaag    60
a                                                                    61

<210> SEQ ID NO 179
<211> LENGTH: 61
<212> TYPE: DNA
<213> ORGANISM: Artificial Sequence
```

```
<220> FEATURE:
<223> OTHER INFORMATION: Synthetic probe

<400> SEQUENCE: 179
gaggagggca gcaaacggga agagtcttcc tttacgatat tatgttgcag tcacagtgta    60
t                                                                    61

<210> SEQ ID NO 180
<211> LENGTH: 61
<212> TYPE: DNA
<213> ORGANISM: Artificial Sequence
<220> FEATURE:
<223> OTHER INFORMATION: Synthetic probe

<400> SEQUENCE: 180
gaggagggca gcaaacggga agagtcttcc tttacgatat tgtgcaggat cttcatgaag    60
g                                                                    61

<210> SEQ ID NO 181
<211> LENGTH: 23
<212> TYPE: DNA
<213> ORGANISM: Artificial Sequence
<220> FEATURE:
<223> OTHER INFORMATION: Synthetic probe

<400> SEQUENCE: 181
cacaaattcg gttctacagg gta                                            23

<210> SEQ ID NO 182
<211> LENGTH: 22
<212> TYPE: DNA
<213> ORGANISM: Artificial Sequence
<220> FEATURE:
<223> OTHER INFORMATION: Synthetic probe

<400> SEQUENCE: 182
tcaacatcag tctgataagc ta                                             22

<210> SEQ ID NO 183
<211> LENGTH: 20
<212> TYPE: DNA
<213> ORGANISM: Artificial Sequence
<220> FEATURE:
<223> OTHER INFORMATION: Synthetic probe

<400> SEQUENCE: 183
ggcattcacc gcgtgcctta                                                20

<210> SEQ ID NO 184
<211> LENGTH: 21
<212> TYPE: DNA
<213> ORGANISM: Artificial Sequence
<220> FEATURE:
<223> OTHER INFORMATION: Synthetic probe

<400> SEQUENCE: 184
aaagagaccg gttcactgtg a                                              21
```

RNA FIXATION AND DETECTION IN CLARITY-BASED HYDROGEL TISSUE

CROSS-REFERENCE

This application claims the benefit of U.S. Provisional Patent Application No. 62/293,490, filed Feb. 10, 2016, which application is incorporated herein by reference in its entirety.

INTRODUCTION

An exciting theme in modern biology is moving toward joint maximization of the content and context of molecular-level observations—that is, obtaining high-resolution and content-rich information about the biological system, while also maintaining this system largely or fully intact to preserve crucial contextual information. Historically these two goals of content and context have been in opposition, since higher-resolution analyses have tended to require disassembling the system or accepting a limited field of view. But the value of obtaining and integrating information about the identity, function and connectivity of cells in intact 3D volumes has been increasingly appreciated.

For example, one of the current challenges in neuroscience is to query molecular identity, activity level, and circuit wiring of individual cells within intact brain networks, which would require linkage of information spanning several orders of magnitude in spatial scale. Until recently, investigating the structure of neural networks in this way required sectioning for optical access and molecular labeling, followed by computer-assisted alignment and 3D reconstruction (Denk and Horstmann, 2004; Micheva and Smith, 2007; Oh et al., 2014). Such reconstructions have been valuable, but are often laborious, limited to small volumes, and susceptible to loss of information at section boundaries, making tract-tracing and circuit-mapping particularly difficult (Wanner et al., 2015). However, tissue-clearing techniques have emerged that, to various degrees, enable the visualization of cell morphology (and in some cases molecular phenotype, as well as local and long-range wiring) embedded within intact neural circuits (Chung et al., 2013; Tomer et al., 2014; Yang et al., 2014; Dodt et al., 2007; Ertürk et al., 2012; Hama et al., 2011; Kuwajima et al., 2013; Renier et al., 2014; Richardson and Lichtman, 2015; Staudt et al., 2007; Susaki et al., 2014; Tainaka et al., 2014).

To date these technologies have chiefly focused on interrogating proteins, whether transgenically-expressed or immunohistochemically-detected (with the exception of single probes tested in CLARITY-based hydrogel experiments in sectioned tissue; Chung et al., 2013; Yang et al., 2014), and many such approaches may not be compatible with accessing the wealth of biological information contained in the RNA of large intact volumes. This untapped opportunity spans untranslated species, including microRNAs (which, among other reasons for investigation, are particularly relevant to human genetically-determined diseases; Esteller, 2011), the majority of splice variants, many immediate early gene (IEG) RNAs used to infer activity of particular regions or cells during behavior (Guzowski et al., 1999; Loebrich and Nedivi, 2009), and even the vast majority of translated gene products, due to limited antibody specificity and availability.

Thus, there remains a need for the development of methods for visualizing RNA in intact tissue. The present disclosure fulfills this need and provides methodology, tools, and resources for cellular-resolution transcriptional profiling of large and intact transparent mammalian tissue volumes, with reliable detection of diverse markers for non-coding transcripts, cell identity, and activity history.

SUMMARY

Methods, kits, and systems for fixation of RNA permitting its detection in intact tissue, such as, large volume of mammalian tissue are disclosed. The methods, kits, and systems utilize carbodiimide-based chemistry to stably retain RNAs in tissue clarified using CLARITY. Also provided herein are methods, kits, and systems for detection of RNAs in clarified tissue.

An aspect of the present disclosure includes a method of preparing a biological specimen for microscopic analysis of a target RNA analyte, the method including fixing the specimen with a plurality of hydrogel subunits; polymerizing the hydrogel subunits to form a hydrogel-embedded specimen; fixing RNA in the specimen using carbodiimide mediated crosslinking; clearing the hydrogel-embedded specimen wherein the RNA is substantially retained in the specimen; and contacting the specimen with a nucleic acid probe for a target RNA analyte.

In some embodiments, the carbodiimide comprises 1-Ethyl-3-3-dimethyl-aminopropyl carbodiimide (EDC). In some embodiments, the nucleic acid probe undergoes a Hybridization Chain Reaction (HCR). In certain embodiments, the nucleic acid probe is a DNA probe. In some embodiments, the nucleic acid probe is a RNA probe. In some embodiments, the specimen is stored for at least one week prior to the contacting. In some embodiments, the specimen is stored at 4° C. for a period of one week to a year prior to the contacting. In some embodiments, the specimen is stored at 4° C. for a period of one week to six months prior to the contacting. In some embodiments, the contacting comprises contacting the specimen with a plurality of nucleic acid probes for a plurality of target RNA analytes. In some embodiments, the clearing comprises substantially removing a plurality of cellular components from the specimen. In some embodiments, the clearing comprises substantially removing lipids from the specimen. In some embodiments, the clearing comprises electrophoresing the specimen. In some embodiments, the electrophoresing comprises using a buffer solution comprising an ionic surfactant. In some embodiments, the specimen is a biopsy specimen or autopsy specimen. In some embodiments, the specimen is from a human. In some embodiments, the method further comprises imaging the specimen using confocal microscopy, two-photon microscopy, light-field microscopy, tissue expansion microscopy, and/or CLARITY™-optimized light sheet microscopy (COLM).

BRIEF DESCRIPTION OF THE FIGURES

FIG. 3A-3G illustrate that DNA diffuses into CLARITY tissue more quickly than antibodies.

FIG. 4A-4F show comparison of antibody-based and DNA-based amplification.

FIG. 5A-5C show validation of amplification specificity.

FIG. 8A-8H show characterization of HCR probe design and amplification sensitivity.

FIG. 9A-9B illustrate detecting activity-induced transcripts and non-coding RNAs in CLARITY volumes.

FIG. 11A-11B illustrate multiplexed detection of mRNAs in CLARITY.

FIG. 13 depicts Table 1 that lists probes for detection of target RNA.

DETAILED DESCRIPTION

Figure 1A:
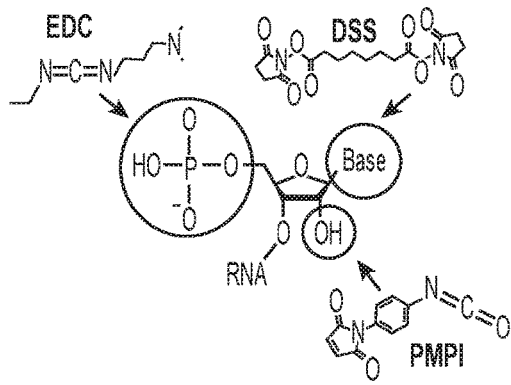
FIG. 1A-1K depict fixation in EDC significantly improves RNA retention in CLARITY volumes.

The present disclosure provides methods, systems, and kits for preparing a tissue specimen for microscope analysis of a target RNA analyte present or suspected of being present in the tissue. These methods, systems, and kits utilize hydrogel subunits to form hydrogel-embedded specimen and carbodiimide for fixing RNA present in tissue prior to clearing the hydrogel-embedded specimen. The tissue specimen prepared using the methods, systems, and kits disclosed herein provides superior retention and increased stability of RNA analyte in the tissue compared to the other methods that have been used for preparing tissue specimen for microscopic analysis of RNA.

All publications, patents and patent applications cited herein, whether supra or infra, are hereby incorporated by reference in their entireties.

It must be noted that, as used in this specification and the appended claims, the singular forms "a", "an" and "the" include plural referents unless the content clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

Methods

The present disclosure provides methods for preparing a biological specimen for microscopic analysis of a target RNA analyte. In certain embodiments, the method comprising fixing the specimen with a plurality of hydrogel subunits; polymerizing the hydrogel subunits to form a hydrogel-embedded specimen; fixing RNA in the specimen using carbodiimide crosslinking; clearing the hydrogel-embedded specimen wherein the RNA is substantially retained in the specimen; and contacting the specimen with a nucleic acid probe for a target RNA analyte.

Aspects of the present methods include fixing the specimen in the presence of hydrogel subunits. By "fixing" the specimen it is meant exposing the specimen, i.e., the components present throughout the specimen, such as within cells of the specimen, to a fixation agent such that the cellular components become cross-linked to one another. By "hydrogel" or "hydrogel network" is meant a network of polymer chains that are water-insoluble, sometimes found as a colloidal gel in which water is the dispersion medium. A detailed description of suitable hydrogels may be found in published U.S. patent application 20100055733, herein incorporated by reference. By "hydrogel subunits" or "hydrogel precursors" is meant hydrophilic monomers, prepolymers, or polymers that can be cross-linked, or "polymerized", to form a three-dimensional (3D) hydrogel network.

The specimen may be fixed in the presence of hydrogel subunits and a fixation agent or a fixative to fix the specimen in the presence of the hydrogel subunits. Suitable fixatives, without limitation, include an aldehyde containing fixative, such as, formaldehyde, paraformaldehyde, glutaraldehyde. Other fixatives such as, acetone, ethanol, methanol, and the like may also be used. The fixative used in the presence of the hydrogel subunits may be at a concentration of about 1-10%, e.g. 1%, 2%, 3%, 4%, 5%, 6%, 7%, 8%, or 10%. In certain embodiments, the fixative may be formaldehyde or paraformaldehyde.

The hydrogel subunits may comprise any convenient hydrogel subunits, such as, but not limited to, acrylamide, bis-acrylamide, poly(ethylene glycol) and derivatives thereof (e.g. PEG-acrylate (PEG-DA), PEG-RGD), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof.

The type and concentration of fixative(s) and hydrogel subunits used in the presently disclosed methods can be selected based on a number of factors, such as, the type of tissue, volume of tissue, thickness of the tissue, duration of fixing and polymerization, and the like. Thus, for example, a fixative/hydrogel composition used for fixing and polymerization steps may comprise an acrylamide monomer at a concentration of from about 1% w/v to about 20% w/v, e.g., about 2% to about 15%, about 3% to about 10%, about 4% to about 8%, and a concentration of bis-acrylamide cross linker in the range of about 0.01% to about 0.075%, e.g., 0.01%, 0.02%, 0.025%, 0.03%, 0.04%, 0.05%, 0.06%, or 0.075%; or, for example, the fixative/hydrogel composition may comprise PEG prepolymers having a molecular weight ranging from at least about 2.5K to about 50K, e.g., 2.5K or more, 3.5K or more, 5K or more, 7.5K or more, 10K or more, 15K or more, 20K or more, but typically not more than about 50K, at a concentration in a range from about 1% w/w to about 50% w/w, e.g., 1% or more, 5% or more, 7.5% or more, 10% or more, 15% or more, 20% or more, 30% or more, 40% or more, and usually not more than about 50%. Concentrations of hydrogel subunits and modifiers that provide desired hydrogel characteristics may be readily determined by methods in the art or by the methods described in the working examples below. In certain embodiments, the hydrogel subunits used in the present methods may be acrylamide, bis-acrylamide or a combination thereof. In certain embodiments, the tissue specimen may be fixed by contacting it with a solution that includes acrylamide, bis-acrylamide, and formaldehyde or paraformaldehyde. In certain embodiments, the tissue specimen may be fixed by contacting it with a solution that includes 1%-4% acrylamide, 0.00125%-0.05% bis-acrylamide, and 1%-10% formaldehyde or paraformaldehyde.

The fixative/hydrogel solution may be delivered to the specimen by any convenient method, e.g., perfusion, injection, instillation, absorption, application, immersion/submersion, etc. The specimen will typically be fixed in the presence of the hydrogel for 15 minutes or more, for example, for 30 minutes or more, 1 hour or more, 2 hours or more, 4 hours or more, 6 hours or more, 12 hours or more, in some instances, for 16 hours or more, 20 hours or more, or 24 hours or more.

Following fixation of the specimen, the hydrogel subunits are polymerized, i.e., covalently or physically cross-linked, to form a hydrogel network. Polymerization may be by any method including, but not limited to, thermal crosslinking, chemical crosslinking, physical crosslinking, ionic crosslinking, photo-crosslinking, irradiative crosslinking (e.g., x-ray, electron beam), and the like, and combinations thereof and may be selected based on the type of hydrogel used and knowledge in the art. The length of time for polymerization will depend on the type of hydrogel subunits used and the chosen polymerization method, but will typically be about 15 minutes to about 48 hours, 30 min to about 10 hours, 1 hour to about 8 hours, 2 hours to about 6 hours, for example, 15 minutes or more, 1 hour or more, 2 hours or more, 3 hours or more, 4 hours or more, 5 hours or more, 6 hours or more, 12 hours or more, 16 hours or more, 24 hours or more, or in some instances, 48 hours. In certain cases, a thermal initiator may be included in the fixative/hydrogel composition used for fixing and polymerization of the tissue specimen. The optimal time and combination of reagents will be known to the ordinarily skilled artisan or may be determined empirically or from any number of publicly available resources (e.g., on the world wide web at piercenet.com; see also, Macroporous Polymers: Production Properties and Biotechnological/Biomedical Applications. Edited by Bo Mattiasson, Ashok Kumar, and Igor Yu. Galeaev. CRC Press 2010; and Crosslinking Reagents Technical Handbook, Pierce Biotechnology, Inc., 2006). In certain cases, the polymerization of the hydrogel may be initiated by incubating the fixed tissue specimen at a high temperature of at least 35° C. to about a 100° C. such as, 37° C. or more, 40° C. or more, or 50° C. or more, 60° C. or more, 70° C. or more, 80° C. or more, 90° C. or more, or 10° C.

In certain embodiments, the fixing the specimen with a plurality of hydrogel subunits and polymerizing the hydrogel subunits to form a hydrogel-embedded specimen may be carried out using the methods disclosed in U.S. patent application publication 20150144490, which is herein incorporated by reference in its entirety.

Once polymerized, the hydrogel-embedded (i.e., hydrogel-hybridized) specimen is exposed to a reagent for fixing the RNA present in the specimen using carbodiimide for crosslinking the RNA to the components of the hydrogel-embedded specimen. In certain aspects, the carbodiimide may crosslink the RNA present in the specimen to amine containing cellular components, such as, proteins and peptides.

Any suitable carbodiimide may be utilized. In certain embodiments, the carbodiimide may be selected from the group consisting of 1-ethyl-3-(3-dimethylaminopropyl) carbodiimide (EDC), 1-ethyl-3-(3-dimethylaminopropyl) carbodiimide hydrochloride (EDC-HCl), 1-cyclohexyl-3-(2-morpholinyl-(4)-ethyl) carbodiimide metho-p-toluenesulfonate (CMC), N,N'-dicyclohexylcarbodiimide (DCC), N,N'-diisopropylcarbodiimide (DIC), and 1-ethyl-3-(3-dimethylaminopropyl)-carbodiimide methiodide (EDC-Mel). In another aspect, the carbodiimide may be 1-ethyl-3-(3-dimethylaminopropyl) carbodiimide (EDC), 1-ethyl-3-(3-dimethylaminopropyl) carbodiimide hydrochloride (EDC-HCl) or 11-ethyl-3-(3-dimethylaminopropyl)-carbodiimide methiodide (EDC-Mel). The concentration of the carbodiimide may range from 1 mM to 500 mM, or 10 mM to 300 mM, or 30 mM to 200 mM, or 50 mM to 100 mM, e.g., 50 mM, 100 mM, 200 mM, or 300 mM.

In one aspect of the disclosed methods, the hydrogel-embedded specimen is contacted with a solution comprising a carbodiimide at a temperature ranging from about 20° C. to about 70° C. For example, the hydrogel-embedded specimen may be contacted with a solution comprising a carbodiimide at a temperature ranging from 30° C. to 50° C., or 35° C. to 45° C., or 35° C. to 40° C., such as, 30° C., 35° C., 37° C., or 40° C.

In one aspect of the disclosed methods, the hydrogel-embedded specimen is contacted with a solution comprising a carbodiimide for a duration of at least 15 min to 10 days, or 1 hour to 5 days, or 3 hours to 3 days, or 5 hours to 1 day, or 5 hours to 16 hours, or 10 hours to 18 hours, for example, 5 hours, or 6 hours, or 7 hours, or 8 hours, or 10 hours, or 12 hours, or 14 hours, or 16 hours, or 18 hrs.

In another aspect of the disclosed methods, the solution comprising a carbodiimide has a pH of about 6.0 to about 10.0. In an embodiment, the solution comprising a carbodiimide has a pH of about 7.0 to about 9.0, such as, 7.5-9.0, 7.5-8.75, 7.75-8.5, 8.0-8.75, 8.0-8.5, e.g., 7.5, 7.75, 8.0, 8.5, or 8.75. The carbodiimide may be present in any suitable buffer, such as, 1-methylimidazole buffer or MES (4-morpholinoethanesulfonic acid) buffer.

In certain embodiments, the fixing the RNA in the specimen may include contacting the hydrogel-embedded specimen with a solution comprising a carbodiimide and a heterocyclic derivative selected from the group consisting of an imidazole, pyrazole, triazole or tetrazole or a combination thereof. In another aspect, the heterocyclic derivative is selected from the group consisting of 1-methylimidazole, imidazole, 1-hydroxyl-benzotriazole, 5-ethylthiotetrazole, and 2-chloromidazole. In an embodiment, the heterocyclic derivative is 5-ethylthiotetrazole. In another embodiment, the heterocyclic derivative comprises 1-methylimidazole and 5-ethylthiotetrazole. In a particular embodiment, the solution for fixing the RNA may include EDC. EDC-HCl, or EDC-Mel and 1-methylimidazole and 5-ethylthiotetrazole.

In certain embodiments, the fixing the RNA in the specimen may be carried out using the methods and reagents disclosed in U.S. application publication no. 20140220574, which is herein incorporated by reference in its entirety.

The presently disclosed methods may be used for fixing any type of RNA in the tissue specimen. For example, the RNA may be messenger RNA (mRNA), ribosomal RNA (rRNA), transfer RNA (tRNA), microRNA (miRNA), long non-coding RNA (lncRNA), mitochondrial RNA (mtRNA), small nucleolar RNA (snoRNA) or other RNA that may be present in the tissue.

Once the RNA is fixed, the hydro-gel embedded specimen may be cleared. By "clearing" a specimen it is meant that the specimen is made substantially transparent, i.e., permeable to light. In other words, about 70% or more of the visual (i.e., white) light, ultraviolet light or infrared light that is used to illuminate the specimen will pass through the specimen and illuminate cellular components therein. e.g., 75% or more of the light, 80% or more of the light, 85% or more of the light, in some instances, 90% or more of the light, 95% or more of the light, 98% or more of the light, e.g. 100% of the light will pass through the specimen. This change in the optical properties of the specimen provides for the visualization of cellular and subcellular components internal to the tissue.

Any treatment that forces cellular components, e.g., lipids, from the specimen, that draws cellular components, e.g., lipids, from a specimen, or that causes cellular components, e.g., lipids, to break down, i.e., dissolve, within a specimen may be used to clear the specimen, including, without limitation, exposure to organic solvents such as xylenes, ethanol or methanol, exposure to detergents such as saponin, Triton X-100 and Tween-20, exposure to ionic surfactants, e.g., sodium dodecyl sulfate (SDS), electrophoresis, hydrodynamic pressure, ultrasonic vibration, solute contrasts, microwave radiation, vascular circulation, and the like.

In some embodiments, clearing may be conducted using an ionic surfactant, e.g., SDS, in order to expedite the clearing process by actively transporting charged ionic micelles out of the specimen that is being cleared. Clearing may be performed in any convenient buffer that is compatible with the selected clearance method, e.g., saline, phosphate buffer, phosphate buffered saline (PBS), sodium borate buffer, sodium tetraborate buffer, boric acid buffer, citric acid buffer, etc., as known in the art, and will typically take about 1-10 days per centimeter thickness of specimen, i.e., usually about 1 day, in some instances 2 days, sometimes 5 days, and typically no more than 10 days per cubic centimeter. Optimal time may be readily determined by visual inspection of the specimen for clarity. The clearing may be conducted at a temperature ranging from 20° C.-100° C. or 20° C.-50° C., or 25° C.-45° C., or 30° C.-45° C. or 35° C.-40° C., such as 35° C., 37° C., or 40° C. In certain embodiments, the clearing time is shorter than the clearing time required when an agent other than a carbodiimide is used for the RNA fixation step. For example, the clearing time is half of that required when using p-maleimidophenyl isocyanate (PMPI) for fixing the RNA in the hydro-gel embedded tissue specimen to obtain the same degree of clearing.

In some embodiments, clearing the hydrogel-embedded specimen comprises electrophoresing the specimen. In some embodiments, the specimen is electrophoresed using a buffer solution that comprises an ionic surfactant. In some embodiments, the ionic surfactant is sodium dodecyl sulfate (SDS). In some embodiments, the specimen is electrophoresed using a voltage ranging from about 10 to about 60 volts. In some embodiments, the specimen is electrophoresed for a period of time ranging from about 15 minutes up to about 10 days.

After clearing, a sample will generally be substantially free of lipids. By "substantially free of lipids" is meant that the original amount of lipids present in the sample before clearing has been reduced by approximately 70% or more, such as by 75% or more, such as by 80% or more, such as by 85% or more, such as by 90% or more, such as by 95% or more, such as by 99% or more, such as by 100%.

In certain embodiments, the fixing the specimen with a plurality of hydrogel subunits, polymerizing the hydrogel subunits to form a hydrogel-embedded specimen and clearing the hydrogel-embedded specimen may be carried out using the methods disclosed in U.S. patent application publication 20150144490, which is herein incorporated by reference in its entirety. This method is also referred to as the CLARITY method or process and the specimen prepared is referred to as CLARITY-based hydrogel tissue.

After clearing the hydro-gel embedded tissue specimen may be contacted with a nucleic acid probe, such as, a DNA probe, RNA probe, Peptide nucleic acid (PNA) probe, locked nucleic acid (LNA™) probe, 2'-O-methyl (2'-OMe) oligoribonucleotide probe, 2'-O-ethyl (2'-OEt) oligoribonucleotide probe, 2'-O-methoxyethyl (MOE) oligoribonucleotide probe or 2',4'-contrained MOE bicyclic nucleic acid (cMOE BNA) probe or 2',4'-contrained 2'-O-ethyl bicyclic (cEt BNA) probe or S-DNA probe, and the like. The sequence of the nucleic acid probe may be determined based on the sequence of the target RNA analyte. The target RNA analyte may be any RNA present in the tissue. In certain embodiments, a plurality of different nucleic acid probes specific for a plurality of target RNA analytes may be used in the disclosed methods. As used herein, the term "specific" in the context of a probe and the target RNA analyte refers to a probe that binds to a target RNA analyte that has a nucleotide sequence that is substantially complementary to the nucleotide sequence of the probe and does not bind to a RNA that has a nucleotide sequence that is not substantially complementary to the nucleotide sequence of the probe. As used herein, substantially complementary refers to a complementarity of at least about 70% or more, such as, 80%, 85%, 90%, 95%, 99% or more. It is understood that the contacting of the specimen with the probe will be conducted under hybridization conditions that increase specific binding between a probe and its target RNA while decreasing non-specific binding. The specificity of binding between a probe and its target RNA analyte can be affected by the length of the probe and presence of repetitive sequences. Appropriate probes may be designed using available algorithms. The probe may be single stranded or double stranded. Probes may be 10 to 20, 11 to 30, 31 to 40, 41 to 50, 51-60, 61 to 70, 71 to 80, 80 to 100, 100 to 150, 150 to 200 or 200-250 nucleotides in length, for example 25, 50, 100 or 150 nucleotides. In certain embodiments, the target RNA analyte may be one or more of the RNA listed in Table 1 in FIG. 13. In certain embodiments, a probe(s) for a target RNA analyte may be one or more probes listed in Table 1 in FIG. 13.

In certain embodiments, the probe may be a labeled probe. The phrase "labeled probe" refers to a probe that contains a detectable moiety. The detectable moiety may produce a signal directly or indirectly. Examples of a detectable moiety that produces a signal directly include fluorescent molecules, radioactive isotopes, electron dense moieties, etc. Detectable moieties that produce a signal indirectly include moieties that produce a signal upon exposure to detection reagents such as substrates or antibodies, etc. A detectable moiety that produces a signal directly can optionally be detected by indirect means such as by using a labeled antibody that binds to the moiety. In certain cases, a signal may be of a particular wavelength which is detectable by a photodetector, e.g., a light microscope, a spectrophotometer, a fluorescent microscope, a fluorescent sample reader, or a florescence activated cell sorter, etc. A probe may be labeled with more than one detectable moiety. In certain embodiments, a plurality (e.g., 2-20) of probes may be used for detecting a plurality of RNA analytes in the tissue specimen. In certain embodiments, a plurality of probes may be used for detecting a single RNA analyte. As used herein, RNA analyte refers to a molecule containing a continuous stretch of ribonucleotides.

In certain embodiments, the nucleic acid probe may be fluorescent. In other embodiments, the nucleic acid probe hybridized to a RNA target analyte in the tissue may be detected by contacting the tissue with a first antibody that binds to a detectable moiety in the probe. The first antibody may be conjugated to a fluorescent moiety or to an enzyme that produces a detectable reaction product. In other cases, a second antibody that binds to the first antibody may be used. The second antibody may be conjugated to a fluorescent moiety or to an enzyme that produces a detectable reaction product. In certain cases, the probe may labeled with biotin, digoxygenin, avidin, and the like.

In certain embodiments, the RNA target analyte may be amplified prior to contacting the tissue specimen with a probe. In other embodiments, the specimen may be contacted with a probe in absence of amplification of the target RNA analyte.

In certain cases, a target RNA analyte fixed in the hydrogel embedded tissue specimen may be detected using hybridization chain reaction (HCR). HCR is a method for the triggered chain of hybridization of nucleic acid molecules starting from stable, monomer hairpins or other more complicated nucleic acid structures. HCR is described in U.S. Pat. Nos. 8,124,751 and 8,105,778. In the simplest version of this process, stable monomer hairpins undergo a chain reaction of hybridization events to form a nicked helix when triggered by a nucleic acid initiator strand. The fundamental principle behind HCR is that short loops are resistant to invasion by complementary single-stranded nucleic acids. This stability allows for the storage of potential energy in the form of loops; potential energy is released when a triggered conformational change allows the single-stranded bases in the loops to hybridize with a complementary strand. In certain embodiments, the probe for contacting the hydrogel-embedded specimen may include a target region and an initiation region. The target region is able to specifically bind to the target RNA analyte, while the initiation region is able to initiate the polymerization of labeled nucleic acid monomers. Thus, the specimen is contacted with a first metastable monomer comprising an initiator region that is complementary to the initiation region of the probe and a second metastable monomer comprising a region complementary to a portion of the first monomer. One or both of the monomers may be labeled with a fluorescent dye. They may also be labeled with a fluorescence quencher such that prior to polymerization the fluorescence is quenched. A fluorescent signal is thus generated upon formation of a polymer and background is reduced.

In other embodiments utilizing HCR, a triggered probe may be used, such that the initiation region is only made available to interact with the monomers when the probe is bound to the target RNA analyte. For example, in some embodiments the probe undergoes a conformational change upon binding to the analyte such that the initiation region is available to stimulate polymerization. In this way, non-specific polymerization resulting from non-specific probe binding is reduced. In certain embodiments, the in situ HCR reactions can be multiplexed to identify the presence of multiple RNA analytes of interest simultaneously.

In another aspect, methods of in situ imaging are provided in which a biological sample is contacted with a probe comprising a target region capable of specifically binding to an analyte of interest and an initiator region, such that the probe binds to the analyte of interest. The sample is then contacted with at least two fluorescently labeled monomers, whereby the initiator region of the bound probe hybridizes to at least one of the monomers. As a result, the monomers form a fluorescently labeled polymer tethered to the analyte via the probe. The fluorescently labeled polymer can then be visualized.

Tissue specimens suitable for use with the methods and systems described herein generally include any type of tissue specimen collected from living or dead subjects, such as, e.g., biopsy specimens and autopsy specimens. Tissue specimens may be collected and processed using the methods, kits and systems described herein and subjected to microscopic analysis immediately following processing, or may be preserved and subjected to microscopic analysis at a future time, e.g., after storage for an extended period of time (at least for 1 day or more, such as up to 5 years, for example, 1 day-3 years, 3 days-1 year, 10 days-9 months, or 2 weeks-6 months, such as, up to 5 years, 3 years, 1 years, or 6 months). In some embodiments, the methods described herein may be used to preserve tissue specimens in a stable, accessible and fully intact form for future analysis. For example, tissue specimens, such as, e.g., human brain tissue specimens, may be processed as described above and cleared to remove a plurality of cellular components, such as, e.g., lipids, and then stored for future analysis. In some embodiments, the methods and systems described herein may be used to analyze a previously-preserved or stored tissue specimen.

By "microscopic analysis" is meant the analysis of a specimen using techniques that provide for the visualization of aspects of a specimen that cannot be seen with the unaided eye, i.e., that are not within the resolution range of the normal human eye. Such techniques may include, without limitation, optical microscopy, e.g., bright field, oblique illumination, dark field, phase contrast, differential interference contrast, interference reflection, epifluorescence, confocal microscopy, CLARITY™-optimized light sheet microscopy (COLM), light field microscopy, tissue expansion microscopy, etc., laser microscopy, such as, two photon microscopy, electron microscopy, and scanning probe microscopy. By "preparing a biological specimen for microscopic analysis" is generally meant rendering the specimen suitable for microscopic analysis at an unlimited depth within the specimen.

Tissue specimens suitable for use with the methods and systems described herein generally include any type of tissue specimens collected from living or dead subjects, such as, e.g., biopsy specimens and autopsy specimens. Tissue specimens may be collected and processed using the methods and systems described herein and subjected to microscopic analysis immediately following processing, or may be preserved and subjected to microscopic analysis at a future time, e.g., after storage for an extended period of time. In some embodiments, the methods described herein may be used to preserve tissue specimens in a stable, accessible and fully intact form for future analysis. For example, tissue specimens, such as, e.g., human brain tissue specimens, may be processed as described above and cleared to remove a plurality of cellular components, such as, e.g., lipids, and then stored for future analysis. In some embodiments, the methods and systems described herein may be used to analyze a previously-preserved or stored tissue specimen. For example, in some embodiments a previously-preserved tissue specimen that has not been subjected to the CLARITY process may be processed and analyzed as described herein.

In some instances, the target RNA analyte may be endogenous to the cells in the tissue specimen. In other instances, the target RNA analyte may be ectopically provided. For example, stereotactic surgery is often used in the field of neuroscience to provide biomolecules such as proteins, viruses, chemicals to neural tissue that label, or "trace", the projections and/or the connectivity of subsets of neurons in vivo or ex vivo. In this technique, a needle comprising a labeling macromolecule is lowered into CNS tissue at a precise location and the labeling molecule is released into the tissue. The molecule will fill the neurons in the vicinity of the injection site and, depending on the type of macromolecule delivered, may be transported across synapses to label their efferent targets ("anterograde tracing") and/or across dendrites to label the afferent neurons from which they are receiving signals ("retrograde tracing"). Examples of agents that may be used to label neurons stereotactically are well known in the art, including, for example, viral tracers, e.g. Herpes simplex virus type1 (HSV) and the Rhabdoviruses. In some instances, the nucleic acid probe may be passively transported into the specimen. In other words, the nucleic acid probe diffuses into the specimen. In other instances, the nucleic acid probe is actively transported into the specimen, e.g. by electroporation, hydrodynamic pressure, ultrasonic vibration, solute contrasts, microwave radiation, vascular circulation, or the like.

To microscopically visualize specimens prepared by the subject methods, in some embodiments the specimen is embedded in a mounting medium. Mounting medium is typically selected based on its suitability for the reagents used to visualize the cellular biomolecules, the refractive index of the specimen, and the microscopic analysis to be performed. For example, for phase-contrast work, the refractive index of the mounting medium should be different from the refractive index of the specimen, whereas for bright-field work the refractive indexes should be similar. As another example, for epifluorescence work, a mounting medium should be selected that reduces fading, photobleaching or quenching during microscopy or storage. In certain embodiments, a mounting medium or mounting solution may be selected to enhance or increase the optical clarity of the cleared tissue specimen. Nonlimiting examples of suitable mounting media that may be used include glycerol, CC/Mount™, Fluoromount™ Fluoroshield™, ImmunHistoMount™, Vectashield™, Permount™, Acrytol™, CureMount™, FocusClear™, or equivalents thereof.

In some instances, the hydrogel-embedded specimen is permanently mounted. In other words, once mounted in mounting medium, the hydrogel-embedded specimen cannot be removed for further manipulation. In other instances, the specimen is temporarily, or reversibly, mounted. In other words, the hydrogel-embedded specimen may be removed from the mounting medium and re-stained after microscopy to visualize alternative/additional biomolecules or subcellular structures. In such instances, macromolecules that were previously added to the specimen, e.g. to visualize certain biomolecules, may be removed after microscopic analysis by, e.g., exposure to organic solvents such as xylenes, ethanol or methanol, exposure to detergents such as sodium dodecyl sulfate (SDS), saponin, Triton X-100 and Tween-20, electrophoresis, hydrodynamic pressure, ultrasonic vibration, solute contrasts, microwave radiation, vascular circulation, and the like. The hydrogel-embedded specimen is then contacted with different macromolecules specific for other biomolecules or subcellular structures. As such, iterative staining may be performed on the same specimen.

Specimens prepared using the subject methods may be analyzed by any of a number of different types of microscopy, for example, optical microscopy (e.g. bright field, oblique illumination, dark field, phase contrast, differential interference contrast, interference reflection, epifluorescence, confocal, etc., microscopy), laser microscopy, electron microscopy, and scanning probe microscopy.

Kits

The present disclosure provides kits for carrying out the methods of the present disclosure. The kits may include one or more of the following: fixative; hydrogel subunits; clearing reagents; nucleic acid probes, in situ hybridization buffer, labeled and or un-labeled antibodies, buffers, e.g. buffer for fixing, washing, clearing, and/or staining specimens; mounting medium; embedding molds; dissection tools; etc. The subject reagents and kits thereof may vary greatly and may include a sub-set of the foregoing reagents.

Also provided are specimens that have been prepared by the subject methods for use in, for example, studying tissue at the cellular and subcellular level. For example, fixed, polymerized specimens, with carbodiimide cross-linked RNA, or specimens that have been fixed, polymerized, cross-linked using a carbodiimide and cleared, are provided for use in studying the expression of genes of interest, for screens to identify candidate agents that target cells and/or subcellular structures of interest, etc. Such prepared specimens may also be provided as a positive control in one of the kits or systems as described herein.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, digital storage medium, etc., on which the information has been recorded. Yet another means that may be present is a website address which may be used via the Internet to access the information at a removed site. Any convenient means may be present in the kits.

Systems

Also disclosed herein are systems that include devices for conducting the methods disclosed herein. The subject system may include devices, such as, electrophoresis apparatus, ultrasounds, microwaves, needles, tubing, perfusion pumps, etc., for fixing, clearing, fixing RNA, contacting with nucleic acid probes, and labeling probes if needed.

Electrophoresis devices suitable for use in the subject methods will generally comprise an electrophoresis chamber into which a buffer solution and the hydrogel-embedded specimen may be placed. The electrophoresis chamber may generally be any suitable size to accommodate a hydrogel-embedded sample of interest, and may be constructed of any material that will retain solution within the chamber, for example glasses and plastics, such as, for example, acrylics, polycarbonates, polystyrenes, polymethyl methacrylates, polyethylene, polyfluoroethylene, polypropylene, polyurethane, polyethylene terephthalate, polytetrafluoroethylene and the like.

In certain cases, the tissue specimen may be at least about 0.1 mm thick, such as, about 10 mm-0.1 mm, 8 mm-1 mm, 6 mm-1 mm, 4 mm-1 mm, 3 mm-1 mm, 3 mm-0.5 mm, 3 mm-0.3 mm, 3 mm-0.1 mm, 5 mm-0.5 mm, 5 mm-0.3 mm, 5 mm-0.1 mm, 10 mm-0.3 mm, or 10 mm-0.1 mm thick. As used herein, the thickness of the tissue specimen is measured along the same plane as that traversed by the illumination beam used for detecting a signal from the tissue. In certain embodiments, the electrophoresis chamber may be sized to hold the tissue sample and to contain space for solutions needed to preparing the specimen for microscopic analysis.

The system for conducting all or some steps of the methods disclosed herein may be automated completely or partially.

Applications

Using the subject methods, reagents, kits, systems and devices, the ordinarily skilled artisan will be able to prepare any biological tissue for microscopic analysis. Methods, reagents, kits, systems and devices may be used to prepare a specimen from any plant or animal, including but not limited to transgenic animals, e.g., vertebrate or invertebrate, e.g. insect, worm, xenopus, zebrafish, mammal, e.g. equine, bovine, ovine, canine, feline, murine, rodent, non-human primate or human. Tissue specimens may be collected from living subjects (e.g., biopsy samples) or may be collected from dead subjects (e.g., autopsy or necropsy samples). The specimens may be of any tissue type, e.g. hematopoietic, neural (central or peripheral), glial, mesenchymal, cutaneous, mucosal, stromal, muscle (skeletal, cardiac, or smooth), spleen, reticulo-endothelial, epithelial, endothelial, hepatic, kidney, pancreatic, gastrointestinal, pulmonary, fibroblast, and other cell types. In some instances, the specimen is the entire organism, e.g. a worm, an insect, a zebrafish. In other instances, the specimen is a whole organ, e.g., the whole brain of a rodent. In other instances, the specimen is a portion of an organ, i.e. a biopsy, e.g. a biopsy of a transplanted tissue. The specimen may be freshly isolated or preserved, e.g. snap frozen. In some embodiments, the specimen may be a previously preserved specimen, such as, e.g., a preserved specimen from a tissue bank, e.g., a preserved specimen of a human brain obtained from a tissue collection program. In some instances, a specimen may be from a subject known to suffer from a specified disease or condition, such as, e.g., a sample of brain tissue from an autistic human. In other instances, a sample may be from a "normal" subject that does not suffer from a specific disease or condition. In some instances, a sample may be from a transgenic subject, such as, e.g., a transgenic mouse.

The carbodiimide mediated crosslinking of the RNA in conjunction with the CLARITY based tissue preparation provides a robust method for detecting a target RNA analyte in an intact tissue volume. The carbodiimide mediated crosslinking of the RNA provides increased retention of RNA in the tissue as compared to other RNA fixation methods, such as, those utilizing disuccinimidyl suberate (DSS). In addition, the use of carbodiimide mediated crosslinking of the RNA does not substantially increase the time required to achieve clearing of the hydro-gel embedded specimen while other RNA fixation methods, such as the use of PPMI almost doubles the clearing time.

The subject methods find many uses. For example, the subject methods may be used for in situ hybridization for detection of target RNA analytes present in low levels in the tissue (for example, 50 copies/cell or less, such as 50-5 copies/cell, 45-5 copies/cell, 40-5 copies/cell, 35-5 copies/cell, 20-5 copies/cell, or 15-5 copies/cell), for quantitation of amount of the target RNA analyte, for visualization of subcellular localization of the target RNA analyte, detection of transiently expressed RNA, and the like.

As another example, the subject methods may be employed to evaluate, diagnose or monitor a disease. "Diagnosis" as used herein generally includes a prediction of a subject's susceptibility to a disease or disorder, determination as to whether a subject is presently affected by a disease or disorder, prognosis of a subject affected by a disease or disorder (e.g., identification of cancerous states, stages of cancer, likelihood that a patient will die from the cancer), prediction of a subject's responsiveness to treatment for a disease or disorder (e.g., a positive response, a negative response, no response at all to, e.g., allogeneic hematopoietic stem cell transplantation, chemotherapy, radiation therapy, antibody therapy, small molecule compound therapy) and use of therametrics (e.g., monitoring a subject's condition to provide information as to the effect or efficacy of therapy). For example, a biopsy may be prepared from a cancerous tissue and microscopically analyzed to determine the type of cancer, the extent to which the cancer has developed, whether the cancer will be responsive to therapeutic intervention, etc.

As another example, a biopsy may be prepared from a diseased tissue, e.g. kidney, pancreas, stomach, etc., to determine the condition of the tissue, the extent to which the disease has developed, the likelihood that a treatment will be successful, etc. The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease. The terms "individual," "subject," "host," and "patient," are used interchangeably herein and refer to any mammalian subject for whom diagnosis, treatment, or therapy is desired, particularly humans. Examples of diseases that are suitable to evaluation, analysis, diagnosis, prognosis, and/or treatment using the subject methods and systems include, but are not limited to, cancer, immune system disorders, neuropsychiatric disease, endocrine/reproductive disease, cardiovascular/pulmonary disease, musculoskeletal disease, gastrointestinal disease, and the like.

Similarly, the subject methods may be used to monitor tissue grafts to determine how well the subject has accepted a transplanted organ/tissue, e.g. heart, kidney, liver, or other organ. In such instances, a biopsy of the transplanted organ may be prepared by the subject methods, and the specimen microscopically analyzed for, e.g., tissue integrity, tissue vascularization, the infiltration of immune cells, etc.

The subject methods may also be used to evaluate normal tissues, organs and cells, for example to evaluate the relationships between cells and tissues of a normal tissue specimen, e.g., a tissue specimen taken from a subject not known to suffer from a specific disease or condition. The subject methods may be used to investigate, e.g., relationships between cells and tissues during fetal development, such as, e.g., during development and maturation of the nervous system, as well as to investigate the relationships between cells and tissues after development has been completed, e.g., the relationships between cells and tissues of the nervous systems of a fully developed adult specimen. In some embodiments, the subject methods may be used on samples collected from transgenic animals to investigate the effects of genetic changes on the development and/or function of specific cells, tissues, and/or organs.

The subject methods also provide a useful system for screening candidate therapeutic agents for their effect on a tissue or a disease. For example, a subject, e.g. a mouse, rat, dog, primate, human, etc. may be contacted with a candidate agent, an organ or a biopsy thereof may be prepared by the subject methods, and the prepared specimen microscopically analyzed for one or more target RNA analytes.

EXAMPLES

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

CLARITY Tissue Preparation.

CLARITY tissue was prepared as described in Tomer et al. (2014). In brief, C57/Bl6 8-12 weeks of age were anaesthetized with beuthanasia (100 mg/kg) and transcardially perfused with cold PBS, followed by cold hydrogel solution (1% or 4% acrylamide, 0.0125% bisacrylamide (for 1% acrylamide) or 0.05% bisacrylamide (for 4% acrylamide), 0.25% VA-044 initiator, 1×PBS, 4% PFA in dH2O). Tissues were removed and post-fixed overnight at 4° C. For induction of immediate early genes, animals were injected with either saline or kainic acid (12 mg/kg, i.p.) 2 hours prior to perfusion and monitored for seizure activity.

For A4P0 samples, tissues were prepared as described (Yang et al., 2014). For A4P0 samples, tissues were first perfused in 4% PFA, post-fixed in 4% PFA for 24 h (4° C.), then transferred to a PFA-free embedding solution (4% acrylamide, 0.25% VA-044 initiator, 1×PBS in dH2O) for 48 h. Conical tubes containing samples were degassed under vacuum for 10 minutes, chamber was flooded with nitrogen, oil was quickly added to the surface of the hydrogel solution and tubes were immediately capped. Gel was polymerized at 37° C. for 5 hours, removed from hydrogel solution and sectioned where indicated using a vibratome (500 µm sections) or sectioning block (1, 2, or 3 mm sections). Tissue was incubated with RNA fixatives after acrylamide polymerization (EDC, 0.1M; PMPI, 0.1M; or DSS, 0.1M, overnight at 37° C.). Tissue was cleared passively in a 4% SDS/0.2M Boric acid (pH=8.5) clearing solution at 37° C. with gentle shaking (0.5 mm, ~1 week; 1 mm, 1-2 weeks; 2-3 mm, ~3 weeks) until transparent. Clearing solution was changed every 1-2 days. Cleared tissue was washed three times (1 hour each), plus overnight, and stored in 1×PBS with 0.3% TX-100.

Total RNA Isolation and Acridine Orange Staining.

Cleared tissue was homogenized in 20 µg/ml proteinase K, extracted with Trizol and then acidic phenol:chloroform: isoamyl alcohol before precipitation with ethanol. For acridine orange staining, sections were rinsed in sodium citrate (SC) buffer for 10 minutes, incubated in acridine orange solution (100 µg/mL) for 3 h, then rinsed in SC buffer, then PBS, and transferred to refractive index matching in Focus-Clear.

Probe Design.

Riboprobes were generated from cDNA templates, reverse transcribed with DIG-labeled dNTPs (Roche), and purified. smFISH probes were designed and synthesized by BioSearch (Petaluma, Calif.). DNA 50mer oligonucleotide probes were purchased from Molecular Instruments (Caltech) or designed using OligoWiz software (Wernersson et al., 2007) and synthesized by Integrated DNA Technologies. LNA probes were synthesized by Exiqon.

For riboprobes, (FIG. 3B,C), cDNA templates for somatostatin (Probe #1, Accession #BC010770, 280-429) or parvalbumin (Probe #2, Accession #BC027424, 203-352) were generated by Genscript. Vectors were linearized and reverse transcribed using T7 RNA polymerase and DIG-labeled dNTPs (Roche), and purified by phenol chloroform extraction. smFISH probes (FIGS. 6J-6L) were designed and synthesized by Biosearch Technologies (Petaluma, Calif.). DNA 50mer initiator-labeled oligonucleotide probes (FIGS. 4A-F, 6A-6O, 9A-9B) were either purchased from Molecular Instruments (Pasadena, Calif.; Parvalbumin, Tac1, Th, 10 probes each), or designed using OligoWiz software (Wernersson et al., 2007) and synthesized by Integrated DNA Technologies (FIGS. 6A-6O and 9A-9B, somatostatin, NPY, VIP, Tac2, Malat1, Npas4, Arc, 4-6 probes each). LNA probes were synthesized by Exiqon (FIG. 9A-9B).

Sequences and concentration of probes used are indicated in Table 1 shown in FIG. 13.

Probe and Antibody Diffusion.

For RNA and DNA probe diffusion, cleared tissue (2 mm) was incubated in hybridization solution for the time indicated, then cooled to 4° C., fixed with PFA, and re-sectioned (200 µm). Cross-sections of the center of tissue were selected for staining with anti-DIG antibody conjugated to HRP and detected with TSA.

For antibody diffusion, tissue was incubated in 50mer DIG-labeled oligonucleotides overnight in 40% formamide and 2×SSC, cooled to 4° C., fixed in 4% PFA for one hour at RT. The tissue was then incubated with anti-DIG Fab fragment antibody coupled to HRP (1:1000) in PBST for the corresponding time and further processed as above for re-sectioning and TSA amplification.

In Situ Hybridization.

For all in situ hybridizations, cleared tissue was equilibrated in hybridization solution for 1 h, hybridized in the same solution overnight at 37° C. unless otherwise noted, then stringency washes were performed at the hybridization temperature to remove excess or non-specifically bound probe. Solutions and temperatures varied for each probe type and are as follows. Oligo(dT): hybridization with 15% formamide, 2×SSC, 10% dextran sulfate, 50 nM probe; stringency 3×1 hour in 15% formamide, 2×SSC then 2×1 hour in 2×SSC. DIG-labeled 50mers: hybridization with 50% formamide, 5×SSC, 0.5 mg/ml yeast tRNA; stringency 3×1 hour in 50% formamide, 5×SSC plus 2×1 hour in 2×SSC and then transferred to PBST. Initiator-labeled 50mers: hybridization with 40% formamide, 2×SSC, 10% dextran sulfate, 0.5 mg/ml yeast tRNA; stringency 3×1 hour in 40% formamide, 2×SSC plus 2×1 hour in 2×SSC. DNA 20mers (smFISH sets): hybridization with 10% formamide, 2×SSC, 10% dextran sulfate; stringency 3×1 hour in 10% formamide, 2×SSC plus 2×1 hour in 2×SSC. LNA probes: hybridization with 50% formamide, 5×SSC, 0.5 mg/ml yeast tRNA, 12.5 nM DIG labeled probe at 20° C. below Tm; stringency 2×1 hour in 5×SSC plus 1 hour in 2×SSC at the same temperature.

For DIG labeled probes, tissue was washed in PBST after stringency. Tissue was incubated overnight in anti-DIG antibody conjugated to HRP (1:500) for 2 days per mm tissue thickness, washed overnight in PBST, developed with tyramide signal amplification (1:50 dilution, 30 minutes), washed 3× in PBST, and transferred to FocusClear for imaging. For initiator probes, tissue was equilibrated in amplification buffer (5×SSC, 0.1% Tween20, 10% dextran sulfate). DNA hairpins were separately heated to 90° C., cooled to RT, and added to amplification buffer. Tissue was incubated in hairpins overnight at RT, then washed 5×1 hour with 5×SSC plus 0.1% Tween20, and transferred to Focus-Clear for imaging.

Propidium iodine staining, where applicable, was performed using a PropI/RNase solution after stringency washes. Sections were transferred to FocusClear for 4 hours prior to imaging. Tissue shrinks once equilibrated to FocusClear for imaging; all scale bars represent the imaged volume, which is approximately 50% of original tissue volume.

Human Tissue.

Human tissue is putative healthy tissue obtained from temporal lobe resections from two patients (46 y.o. female, 18 y.o. male). Tissue was equilibrated in 1% hydrogel solution for 2 days at 4° C., polymerized for 5 hours at 37° C., and cleared for 5 weeks in 4% SDS at 37° C.

Confocal Microscopy.

All images were taken on a Leica SP5 confocal microscope with a 10×/0.4 objective (WD: 2.2 mm) or 20×/0.75 objective (WD: 0.66 mm) at 488 nm (FITC), 514 nm, 543 nm, or 647 nm excitation.

Experimental Subjects.

Animal husbandry and all aspects of animal care and euthanasia as described were in accordance with guidelines from the National Institutes of Health and have been approved by members of the Stanford Institutional Animal Care and Use Committee. Use of surgical and post-mortem human tissue was in accordance with guidelines from the National Institutes of Health and approved by the Stanford Institutional Review Board.

CLARITY Tissue Preparation for In Situ Hybridization

Passive tissue clearing is performed as described in Tomer et al. Nature, 2014. In brief:

1. Perfuse animal with cold PBS, then cold CLARITY hydrogel solution:

| Hydrogel Solution | | |
|---|---|---|
| Chemical | Volume in 400 ml | Final Concentration |
| Acrylamide (40%) | 10 mL | 1% final conc |
| Bis-acrylamide (2%) | 2.5 mL | 0.00125% final conc |
| VA-044 Initiator | 1 g | 0.25% final conc |
| 10X PBS | 40 mL | 1X |
| 16% PFA | 100 mL | 4% |
| d H$_2$O | 247.5 mL | — |

2. Postfix brain in 20 ml of hydrogel solution at 4° C. overnight.

3. Degas solution under vacuum to remove dissolved oxygen, which inhibits polymerization. This can be done by degassing, flooding the chamber with nitrogen, then quickly capping the tube.

4. Incubate 5 hours at 37° C.

5. Section tissue, if applicable.

6. Transfer tissue to methylimidizole buffer (80 µl methylimidizole in 10 ml water) for 15 minutes.

7. Incubate tissue in EDC solution at 37° C. o/n. This compound acts as a fixative for 5' terminal phosphates (Pena et al., 2009; Tymianski et al., 1997). This fixative is particularly helpful in preserving and detecting small RNAs, but also increases retention of mRNAs. To note: EDC fixation will increase clearing time by few days.

| EDC Fixative Solution | | |
|---|---|---|
| Chemical | Mass in 10 ml | Final Concentration |
| EDC | 0.19 g | 0.1M |
| ETT | 0.13 g | 0.1M |

| EDC Fixative Solution | | |
|---|---|---|
| Chemical | Mass in 10 ml | Final Concentration |
| Methylimidizole Buffer (80 µl Methylimidizole in 10 ml in H$_2$O) | 80 µl | | pH to 8.5 with NaOH.

8. Move post-fixed sections to clearing solution. Passive clearing in 4% SDS/0.2M Boric acid (pH=8.5) clearing solution at 37° C. until clear. Switch out solutions every day for at least first few days, then every other day should suffice.

| Clearing Solution | | |
|---|---|---|
| Chemical | Mass in 1 L | Final Concentration |
| Sodium tetraborate | 40.24 | 0.2M |
| SDS | 40 g | 4% |
| H$_2$O | 1 L | — | pH to 8.5 with NaOH.

9. After clearing, wash 3× in PBST (PBS+0.3% Triton), 1 hour each, at RT and once overnight.

Example 1

Advancing Clarified Tissue Chemistry with Carbodiimide-Based RNA Retention

Many existing clearing methods rely on incubation of tissue for prolonged periods of time at temperatures of 37° C. or greater (Chung et al., 2013; Tomer et al., 2014; Yang et al., 2014; Renier et al., 2014; Susaki et al., 2014; Tainaka et al., 2014); however, formalin is known to revert its crosslinks at elevated temperatures, and the bonds made to nucleic acids are particularly vulnerable (Masuda et al., 1999; Srinivasan et al., 2002). Therefore, to improve retention of RNA during high-temperature tissue clearing, we sought to introduce temperature-resistant covalent linkages to RNA molecules prior to clearing, by targeting functional groups on the RNA molecule for fixation to surrounding proteins or the hydrogel matrix.

Figure 1B:
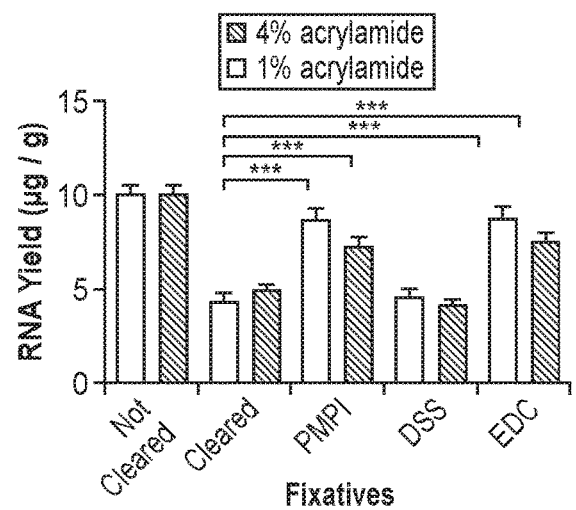

We explored three tissue-chemistry strategies: EDC (1-Ethyl-3-3-dimethyl-aminopropyl carbodiimide) for linkage of the 5'-phosphate group to surrounding amine-containing proteins (Pena et al., 2009; Tymianski et al., 1997); PMPI (p-maleimidophenyl isocyanate) for linkage of the 2' hydroxyl group to surrounding sulfydryl-containing proteins (Shen et al., 2004); and DSS (disuccinimidyl suberate) for linkage of amine-containing side chains in RNA to surrounding amine-containing proteins (Mattson et al., 1993) (FIG. 1A). These crosslinks were introduced after hydrogel embedding (Chung et al., 2013). After fixation, samples were fully cleared and RNA was extracted from each preparation. We observed that although DSS provided no significant increase in RNA yield (potentially due to overfixation of RNA through multiple amine groups on each RNA molecule), there was markedly improved retention of RNA in EDC and PMPI-fixed samples compared with control for both 1% and 4% acrylamide hydrogel compositions (FIG. 1B). However, since PMPI doubled tissue-clearing time, while EDC only marginally increased clearing time (1-2 extra days in 1 mm tissue blocks), we proceeded with EDC as an RNA-fixation agent for CLARITY.

Figure 1C:
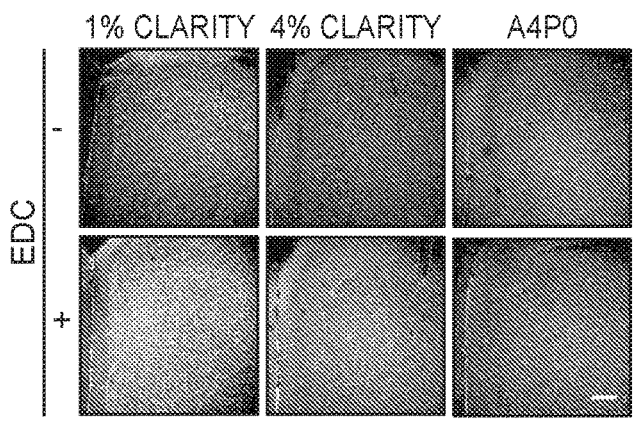
Figure 1D:
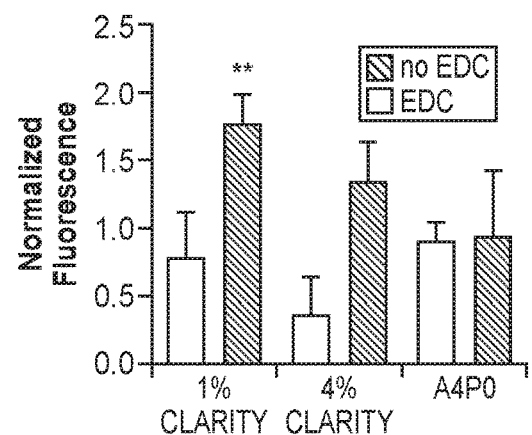
Figure 1E:
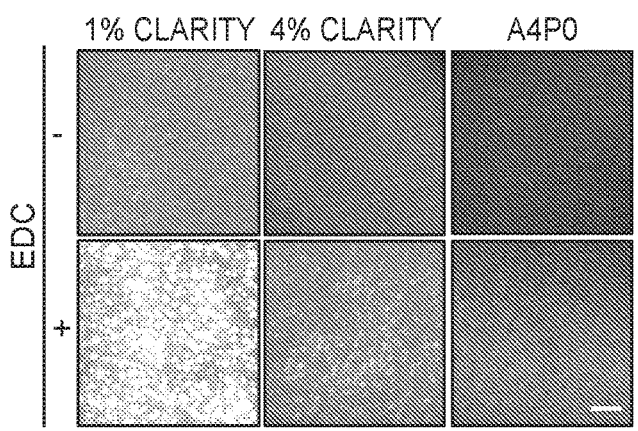
Figure 1F:
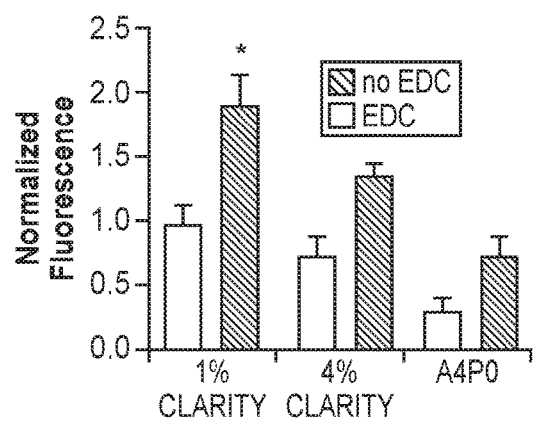
Figure 1G:
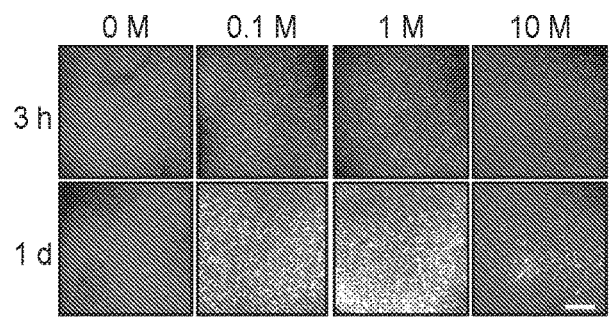

To complement these quantitative total-RNA biochemical measures with direct visualization of retained RNA within tissue, we stained tissue samples of different hydrogel compositions with acridine orange, an intercalating RNA dye. We found significantly increased RNA staining in EDC fixed samples, with EDC-treated 1% CLARITY tissue showing the best RNA labeling (FIG. 1C, 1D). While promising, these total RNA measures did not specifically address mRNA, the population most relevant to molecular phenotyping and activity-dependent gene expression (in contrast to the more abundant rRNA, which by virtue of tight association with proteins could contribute disproportionately to the improvement seen with EDC). To determine if EDC improved mRNA preservation, we performed in situ hybridization with a 50 base deoxy-thymine oligonucleotide (oligo(dT)) to target the polyA tail of mature mRNA. Again, we found that 1% CLARITY with EDC samples exhibited the highest RNA signal (FIGS. 1E, 1F). Surprisingly, the 4% acrylamide hydrogel composition with EDC exhibited significantly reduced RNA detection with both acridine orange staining and oligo(dT) in situ hybridization (as well as weaker staining in target-specific in situ hybridization; FIG. 2A). This consistent picture may reveal that the dense hydrogel network in 4% CLARITY makes mRNA targets less accessible for probe hybridization. In support of this notion, we find high concentrations (10M) of EDC also reduced mRNA staining, whereas more modest fixation (0.1M-1.0M EDC) provided the most effective labeling of RNAs (FIG. 1G, 1H).

A major motivation for RNA detection includes broad application to clinical tissue, but human samples are particularly prone to RNA degradation, since pre-fixation post-mortem intervals vary, immersion-fixation crosslinks tissue more slowly than transcardial perfusion, and clinical samples are often banked for extended periods of time. We have also found that human tissue clears more slowly and, in some cases, demands higher clearing temperatures. To test if EDC could improve RNA retention in human tissue, we compared two human samples collected during temporal lobe resection, one treated with EDC and one an untreated control (1% CLARITY hydrogel). Although both samples showed comparably strong mRNA signal prior to clearing, we found that only the EDC-treated sample exhibited detectable mRNA after clearing (FIG. 1I, 1J). We reasoned that EDC might not only be critical for the immediate processing of CLARITY samples, but might enable long-term storage with little RNA loss. To test this idea, we extracted and measured total RNA from rodent tissue during each stage of the clearing process. After a small loss of RNA during clearing, there was no significant loss during subsequent storage at 4° C. for up to 6 months (FIG. 1K), demonstrating a surprising level of stability (also reflected in target-specific in situ hybridization; FIG. 2B). Together, these data identify and validate a nucleic acid-tuned CLARITY chemistry with EDC.

Figure 1H:
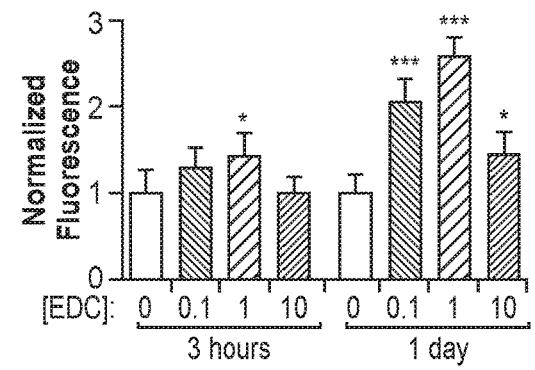
Figure 1I:
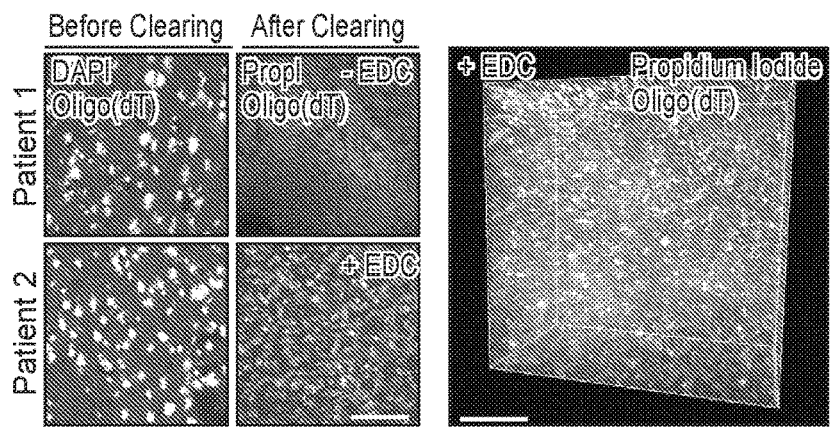
Figure 1J:
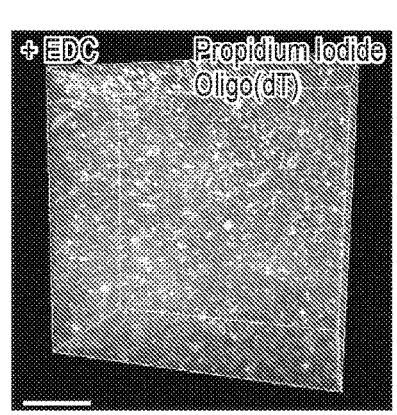
Figure 1K:
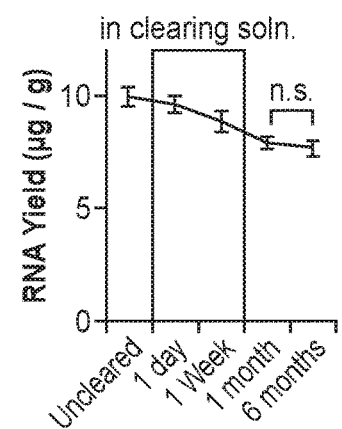
Figure 2A:
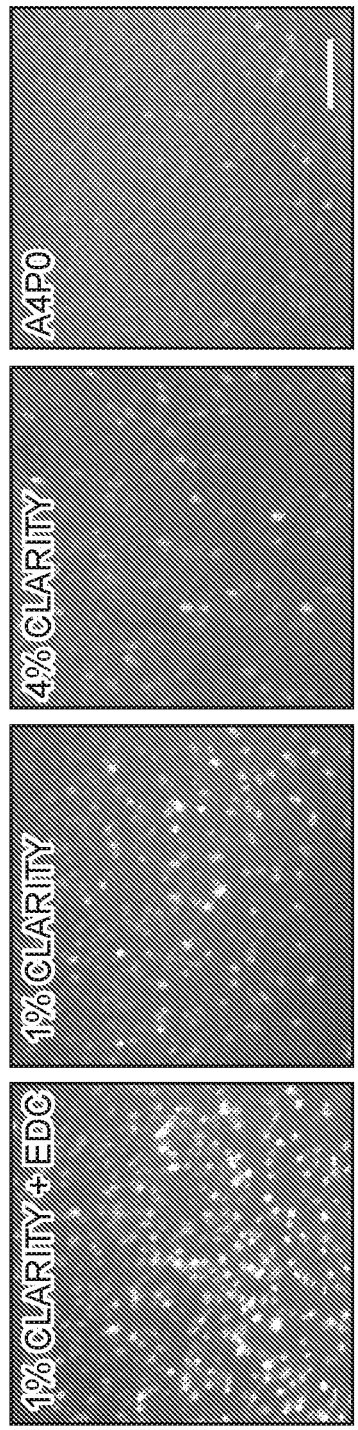
FIG. 2A-2B show characterization of tissue formulation and storage time for in situ hybridization.
Figure 2B:
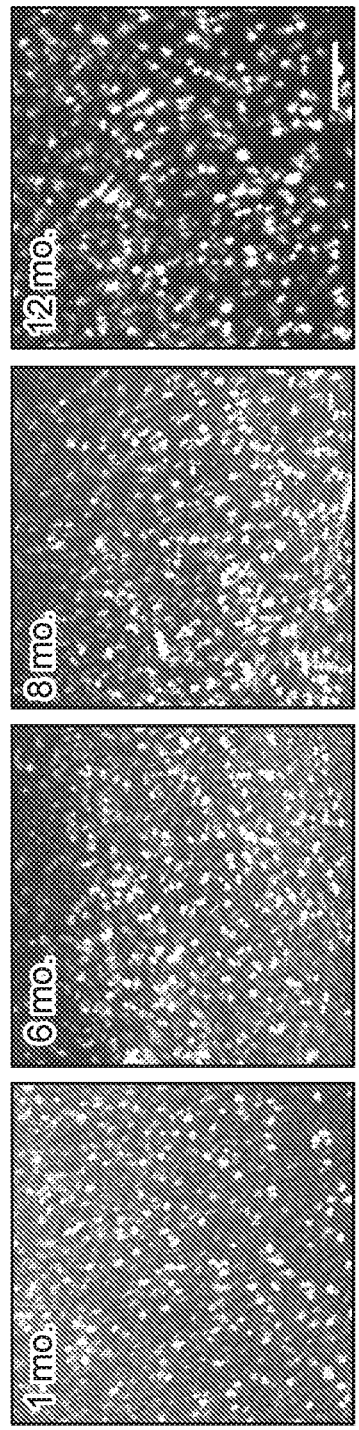

FIG. 1A-1K. Fixation in EDC significantly improves RNA retention in CLARITY volumes. (FIG. 1A) Chemical compounds targeting functional groups on RNA (red circles) were characterized and assessed for RNA fixation and retention. (FIG. 1B) 1 mm mouse brain blocks were embedded in CLARITY hydrogel containing either 1% or 4% acrylamide, then either immediately processed for RNA extraction (uncleared), or post-fixed overnight in PMPI, DSS, EDC, or no-fix, then cleared until visually transparent, and processed for RNA extraction. There was a significant increase in RNA yield in PMPI and EDC treated groups relative to cleared no-fix controls (* P<0.001, one-way ANOVA, with Sidak's post-hoc multiple comparisons test n=6 slices per group). (FIG. 1C) 1 mm blocks embedded in hydrogel (containing 1% or 4% acrylamide, or 4% acrylamide with no PFA) were post-fixed with EDC (+) or no fix (−), then cleared and stained with acridine orange to visualize total RNA levels (false colored; RNA signal in pink). Scale bar, 200 µm. Relative intensities are quantified in FIG. 1D. (FIG. 1D) 1% hydrogel embedded slices post-fixed in EDC showed significantly more RNA than all other conditions tested. Fluorescence intensities are normalized to mean intensity for all conditions (P<0.01, one-way ANOVA, with Sidak's post-hoc multiple comparisons test. n=5 slices per group). (FIG. 1E) 1 mm blocks prepared as in (FIG. 1C), hybridized with an oligo(dT) probe to detect mRNA (false colored). Scale bar, 50 µm. Relative intensities are quantified in (FIG. 1F). (FIG. 1F) 1% hydrogel embedded slices post-fixed in EDC showed more mRNA than all other conditions tested. Fluorescence intensities are normalized to mean intensity for all conditions for each experiment (P<0.01 One way ANOVA, Tukey's post-hoc test for multiple comparisons. n=4 slices per condition). (FIG. 1G) 1 mm blocks of tissues were embedded in a 1% CLARITY hydrogel and post fixed with 0, 0.1, 1, or 10M EDC, either for 3 hours or 1 day at 37° C. Oligo(dT) was performed as in (FIG. 1E). Relative intensities are quantified in (FIG. 1H). (FIG. 1H) Fixation with 0.1M or 1M EDC for 1 day produced optimal RNA hybridization in 1% CLARITY tissue. Fluorescence intensities from oligo(dT) are normalized to mean intensity of the no EDC condition. Asterisks indicate statistical significance compared to 0M EDC, 3 hour condition (*P<0.001, *P<0.05, One way ANOVA, Tukey's post-hoc test for multiple comparisons). n=4 slices per condition. (FIG. 1I) In situ hybridization in human tissue from temporal lobe resection. Left, small samples of resection from each patient were PFA fixed and oligo(dT) hybridization was performed to confirm that mRNA was intact before clearing. The remaining tissue was immersion fixed in 1% CLARITY hydrogel (2 days), embedded, then cleared immediately (−EDC), or fixed in EDC overnight at 37° C. prior to clearing (+EDC). Right, mRNA was detected by oligo(dT) and DNA was stained with propidium iodide (PropI). Scale bar, 100 µm. (FIG. 1J) 3D rendering of EDC fixed human temporal lobe volume (same patient as in (FIG. 1G)). Scale bar, 100 µm. (FIG. 1K) 1 mm tissue blocks (1% hydrogel, EDC postfix) were processed for RNA extraction at various time points: uncleared (immediately after post-fixation); 1 day and 1 week (while in clearing solution); 1 month and 6 months (after clearing and stored in PBST). There is no significant loss of RNA during storage even up to 6 months at 4° C. (n=6 slices per group, n.s. paired t-test). All data are means±S.D. See also FIG. 2A, 2B.

FIG. 2A-2B. Characterization of tissue formulation and storage time for in situ hybridization, related to FIG. 1A-1K. (FIG. 2A) CLARITY sections (1 mm) of mouse tissue from cortex embedded in 1% CLARITY hydrogel, 4% CLARITY hydrogel, 1% CLARITY hydrogel with EDC postfixation, or A4P0 (4% acrylamide, no bis-acrylamide, no PFA during acrylamide polymerization), were cleared in 4% SDS until transparent, and in situ hybridization for somatostatin was performed on the cleared tissue. Images are maximum z-projections from 5 planes, z-interval=20 µm. Scale bar, 100 µm. (FIG. 2B) EDC-CLARITY sections (1 mm, 1% hydrogel) were cleared until transparent and stored in PBST for the times indicated. In situ hybridization for somatostatin was performed and confocal images were acquired. Images are maximum z-projections from 5 planes, z-interval=20 µm. Scale bar, 100 µm.

Example 2

Quantifying Diffusion of In Situ Hybridization Components into Clarified Tissue

After ensuring stable retention of RNAs, we next focused on access to target RNAs for specific labeling in transparent tissue volumes. Traditional in situ hybridization (ISH) uses labeled DNA or RNA probes, which are detected by enzyme-conjugated antibodies that catalyze the deposition of chromophores or fluorophores at the target location. Interrogation of RNA by these methods requires the penetration of each component to the target location. Since prior work had only shown detection of RNA in small volumes (100-500 µm thick; Chung et al., 2013; Yang et al., 2014), we sought to test the ability of ISH components to diffuse into intact EDC-CLARITY tissue.

Figures 3A, 3B, 3C:
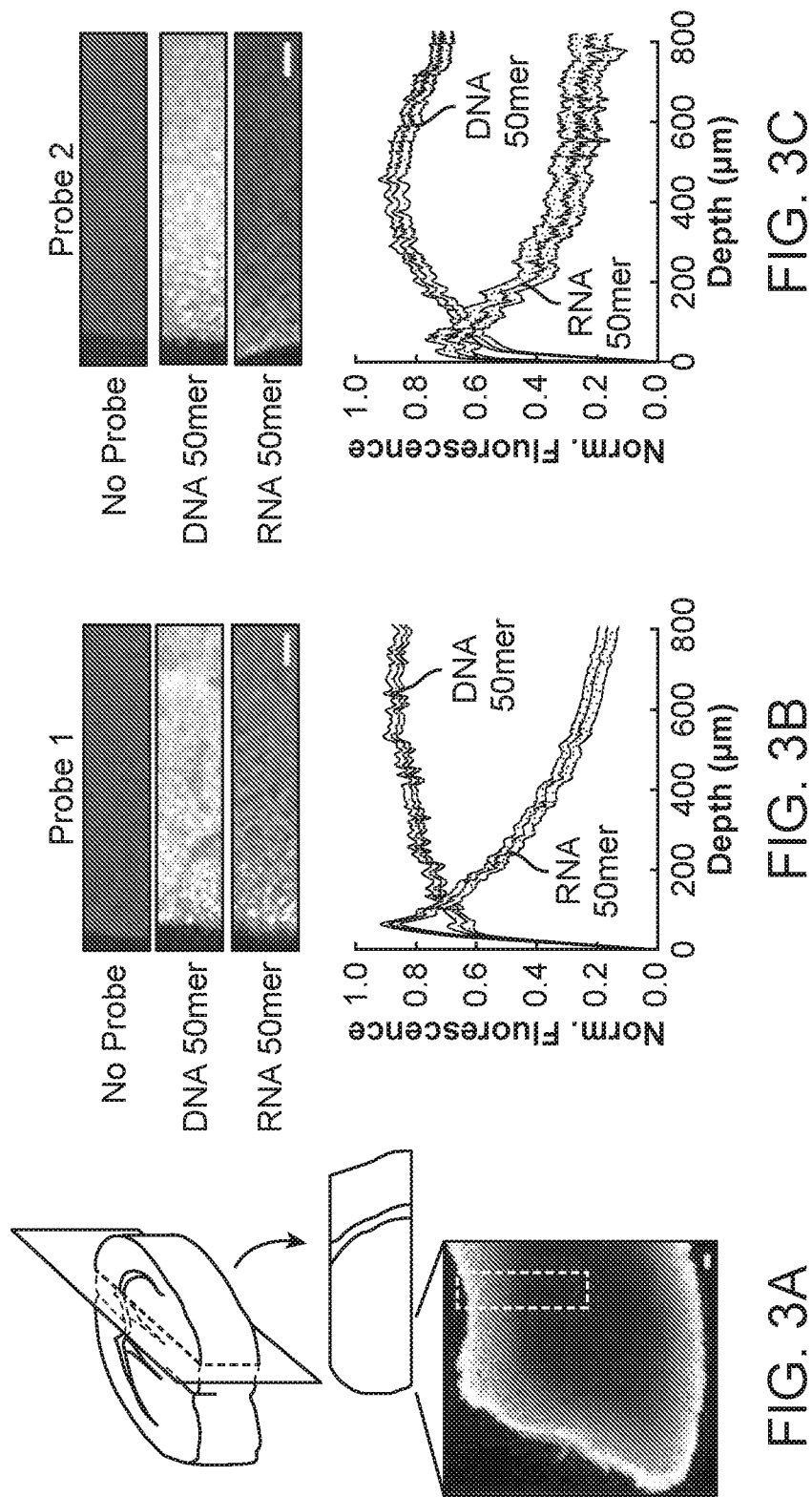

We began by characterizing the diffusion of nucleic acid probes into EDC-CLARITY tissue. We incubated tissue blocks with 50-base DIG-labeled DNA or RNA probes, and visualized the diffusion profile of these probes by cutting cross-sections through the center of the tissue blocks and quantifying probe density on the newly exposed surface via antibody-based enzymatic amplification (tyramide signal amplification; TSA) (FIG. 3A). We found that DNA probes diffused significantly faster into EDC-CLARITY tissue than corresponding RNA probes (FIG. 3B-3D); this important effect may be due to greater nonspecific tissue binding of RNA at this temperature, hindering penetration. Strikingly (and with substantial implications for nucleic acid labeling as the potential approach of choice for transparent tissue molecular phenotyping), we consistently observed DNA probes reaching the center of 2 mm tissue blocks within 3 hours. It should be noted that this detection method (TSA) may saturate at higher concentrations and obscure more subtle underlying concentration gradients expected to be present at 1-3 hour time points, but these diffusion rates are still considerably faster than observed for antibodies (Chung et al., 2013; Tomer et al., 2014).

At 37° C. (optimized for DNA-RNA hybridization), DNA probes reached the center of a 2 mm-thick block in <1 hour (FIG. 3E). In contrast, enzyme-linked Fab antibody fragments penetrated only ~500 µm into tissue even after 2 days (FIG. 3F). Importantly, the rate of diffusion for the Fab fragment was almost two orders of magnitude slower than that of the DNA oligonucleotide (FIG. 3G) under the EDC-CLARITY-ISH condition. Taken together, these experiments reveal that short DNA probes rapidly diffuse throughout large volumes of EDC-CLARITY tissue and suggest that an optimal approach to labeling native RNA species in large intact volumes could leverage the speed and specificity of short DNA probes in addition to EDC tissue chemistry.

FIG. 3A-3G. DNA diffuses into CLARITY tissue more quickly than antibodies. (FIG. 3A) Tissue configuration for B,C,E, and F. 2 mm EDC-CLARITY blocks are incubated in nucleic acid probes or antibody for time indicated and fixed in 4% PFA. 200 µm cross-sections are cut, probe diffusion is detected by TSA on the newly exposed tissue surface, and ROIs are selected as indicated by the dotted box and quantified in B,C,E, and F. (FIG. 3B, 3C) 3 h incubation with DIG-labeled riboprobes or DNA oligonucleotides (50 bases) targeting two different mRNAs in 50% formamide, 5×SSC at 55° C. Top, example ROIs of tissue as shown in (FIG. 3A), pseudocolored. Cross-section is incubated in anti-DIG Fab fragment antibody conjugated to HRP and detected with TSA using FITC. Bottom, quantification of signal intensity as a function of depth for 10-15 ROIs from 3 experiments. For each ROI, no probe control is subtracted, and signal is normalized to peak intensity. (FIG. 3D) Quantification of ratio of signal intensity at tissue edge to center, calculated as maximum intensity over first 100 µm to average intensity of last 100 µm. (****P<0.0001, One way ANOVA, Tukey's post hoc test for multiple comparisons). (FIG. 3E) Diffusion of 50 base DNA oligonucleotide at shorter incubation times with hybridization conditions optimized for in situ hybridization with DNA probes (30, 60 and 180 minutes; 2×SSC, 40% formamide, 37° C.). n=6-12 ROIs. (FIG. 3F) Antibody diffusion. CLARITY tissue is incubated in 50 base oligonucleotide probes overnight, washed, and transferred to anti-DIG antibody conjugated to HRP for time indicated. Tissue is sectioned as in (A), and antibody diffusion is detected by TSA. For 4 hours, n=25 ROIs; 12 hours, n=8; 24 hours, n=17; 48 hours, n=24. (FIG. 3G) Diffusion constants and R2 values for nucleic acid and antibody diffusion in CLARITY tissue. Constants calculated by fitting average curves to Fick's Law: $y=n0*erfc(x/(2*\sqrt{(D*t)}))$ for one dimensional diffusion in a uniform medium with constant boundary condition. Diffusion rate is slower than reported previously in CLARITY tissue (Li et al., 2015), which may arise from additional crosslinking during EDC fixation, or changes in tissue properties during in situ hybridization. Curves used for fitting: RNA, 3 hours incubation; DNA, 30 min incubation; Antibody, 4 hours incubation. All error bars indicate SEM. All scale bars=100 µm.

Example 3

In Situ Hybridization in EDC-CLARITY

Based on these findings that demonstrate stable retention of RNA with EDC-CLARITY and rapid penetration with short DNA probes, we next sought to develop a panel of oligonucleotide-based ISH techniques for application to large transparent tissue volumes. We began with digoxigenin (DIG)-labeled DNA oligonucleotide probes targeting somatostatin mRNA (3 probes) and amplified with anti-DIG HRP-conjugated antibody and TSA (FIG. 4A). In initial tests, we were readily able to resolve individual cells expressing somatostatin mRNA, demonstrating that specific mRNA species within the EDC-CLARITY hydrogel can be retained and are accessible to ISH probes (FIG. 4C).

However, using this technique in larger volumes revealed two major limitations: (1) the surface of the tissue sections showed non-specific staining that could result in false positives during cell detection, and (2) the signal was visible only to a depth of <300 µm (FIG. 4C). A similar pattern was seen in parallel experiments with a probe set targeting YFP mRNA in a Thy1-YFP transgenic mouse, confirming that under these conditions TSA signal at the tissue surface lacks specificity (FIG. 5C). We hypothesized that the main sources of surface staining and signal heterogeneity resulted from a concentration gradient of antibody penetrating the EDC-CLARITY hydrogel and, consequently greater surface deposition of fluorophore during enzymatic amplification. We and others have found that probes can be labeled directly with fluorophore when RNA copy-number is high and little amplification needed (Yang et al., 2014), though with limitations on sensitivity and volume size (up to 1 mm blocks, still far greater than the 20-40 µm queried with traditional techniques). Nevertheless, this restriction in volume, the need for exclusion of superficial tissue, and the severe limitation to highly-expressed transcripts together pointed to the need for further innovation to exploit the speed of DNA penetration into EDC-CLARITY tissue (FIG. 3B, 3E).

Figure 4F:
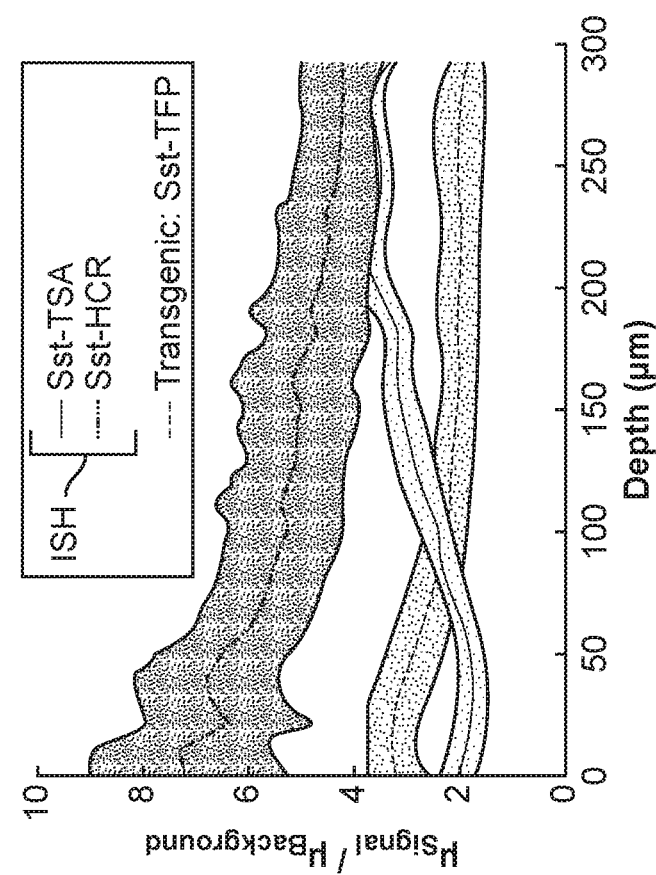
Figure 4E:
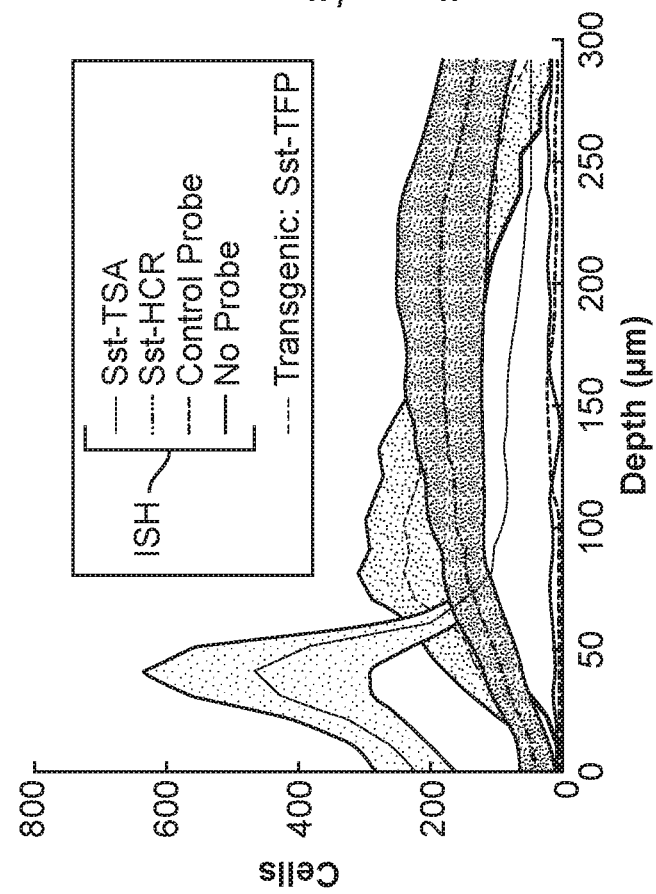

FIG. 4A-4F. Comparison of antibody-based and DNA-based amplification. (FIG. 4A) Workflow for TSA reaction. DIG-labeled probes are hybridized to target mRNA. HRP conjugated anti-DIG antibodies bind to hybridized probes and are detected by TSA. (FIG. 4B) Workflow for HCR reaction. Initiator-labeled probes are hybridized to target mRNA. In a second step, initiator sequences hybridize to toehold of fluorophore bearing hairpins, starting a chain reaction of hairpin assembly. (FIG. 4C-4D) In situ hybridization for somatostatin mRNA in CLARITY tissue. Above, z=100 µm, 200 µm, and 300 µm into CLARITY tissue volume of mouse cortex using traditional ISH (FIG. 4C) or hybridization chain reaction (FIG. 4D). Scale bars, 100 µm. Below, yz-subsections of CLARITY volume and 3D rendering of 1 mm sections. Arrowheads indicate the z-location of the sections above. Arrows indicate the tissue surface. Due to high surface background, the top 130 µm of tissue are not shown for the 3D rendering in (FIG. 4C). Scale bars, 100 µm (left), 300 µm (right). (FIG. 4C) DIG-labeled oligonucleotide probes detected with anti-DIG antibody (2 days) and TSA. Somatostatin expressing cells can be detected, but surface has high background and signal diminishes deeper in the tissue. (FIG. 4D) Initiator-labeled oligonucleotide is detected with HCR reaction (1 day), resulting in more uniform staining. (FIG. 4E) Number of cells as a function of tissue depth after local thresholding and cell segmentation on each imaging plane, 10 µm z-interval. High surface background in TSA reaction yields a large number of putative false positives 0-75 µm into the tissue section. Detection with HCR amplification shows a more uniform labeling of cells, comparable to the distribution of somatostatin cells in a genetically encoded reporter mouse (Sst-TFP). (FIG. 4F) Ratio of signal to background as a function of depth in tissue, calculated from ratio of mean signal intensities segmented in (F) to the mean background intensity. For (FIG. 4E-4F), No Probe, n=3; Scrambled Control, n=3; TSA, n=5; HCR, n=9; Sst-TFP, n=4. P<0.05, Kruskal-Wallis test on mean ratio over entire depth. All error bars indicate SEM. See also FIG. 5A-C.

FIG. 5. Validation of amplification specificity, related to FIG. 4A-4F. (FIG. 5A) EDC-CLARITY sections (1 mm) of tissue from Thy1-YFP mouse cortex. YFP probes were either hybridized at 45° C. (50% formamide, 5×SSC) or at 37° C. (40% formamide, 2×SSC) overnight and amplified using HCR. (Top) Three dimensional rendering of YFP fluorescence after in situ hybridization. (Bottom) Three dimensional rendering of YFP mRNA by HCR-based in situ hybridization. Scale bar, 200 µm (FIG. 5B) YFP fluorescence from EDC-CLARITY tissue after in situ hybridization at 37° C. or 45° C., calculated as the ratio of mean intensity of signal to the mean intensity of the background. Each data point represents one volume. Representative volumes in (FIG. 5A) are indicated in red. (FIG. 5C) EDC-CLARITY sections are hybridized with YFP probes labeled with either DIG or initiator sequences and amplified with TSA or HCR, respectively. Cells identified by YFP protein fluorescence (green) or YFP ISH (black) after local thresholding and cell segmentation are plotted against tissue depth; 10 µm z-interval. High background on tissue surface with TSA amplification produces many false positives 0-50 µm from the tissue surface that are not seen in the YFP protein controls (n=3 for each condition, error bars represent SEM).

Example 4

DNA-Based ISH Signal Amplification

We hypothesized that an all-DNA based amplification system rather than the traditional antibody approach might be an ideal solution. Recent work has capitalized upon the programmable base-pairing of DNA molecules to design DNA structures that amplify signal by several orders of magnitude (Battich et al., 2013; Choi et al., 2010). We explored integrating this approach with EDC-CLARITY tissue chemistry, selecting the hairpin chain reaction amplification system (HCR; Choi et al., 2010) for further development since HCR (a) involves only small DNA oligonucleotides (<150 bases) which self-assemble at the target mRNA, and (b) requires only two hybridization steps (FIG. 4B).

In the first hybridization step, an oligonucleotide probe containing a 36-base initiator sequence binds to target mRNA. In a second step, two fluorophore-tagged oligonucleotides are added, which are kinetically trapped in a hairpin conformation in the absence of the initiator sequence. As they diffuse into the tissue and encounter initiator sequences on hybridized probes, base pairing between the initiator sequences and the single-stranded toehold on Hairpin 1 open the hairpin, revealing a new initiator sequence capable of opening Hairpin 2. In turn, Hairpin 2 opens to reveal the original initiator sequence, starting the cycle anew. As the chain self-assembles, fluorophores accumulate at the target location. It is estimated that the hairpin chain reaction can amplify the signal approximately 200 fold (Choi et al., 2014), and we expected that this degree of amplification might be sufficient to detect RNA in EDC-CLARITY.

To test this approach, we appended initiator sequences to the 3' and 5' ends of the three somatostatin oligonucleotide probes used above, hybridized the probes to EDC-CLARITY tissue, and amplified with HCR hairpins. We found that the combination of EDC-CLARITY and HCR amplification exhibited excellent signal, low background, produced no non-specific surface staining and significantly improved the depth at which we could identify individual cells (FIG. 4D). The signal-to-background ratio was significantly higher than in TSA-based amplification (FIG. 4F) with the characteristic sparse pattern of somatostatin mRNA expression clearly distinguishable from background (FIG. 4D). Moreover, the distribution and cell density detected with HCR amplification mirrors somatostatin expression in transgenic reporter mice, underscoring the specificity of this method (Sst-TFP, FIG. 4E).

Example 5

In Situ Hybridization in Intact Tissue

Linking information on cellular morphology, connectivity, and activity to information on RNA expression will be of substantial value; accordingly, we sought conditions for in situ hybridization in EDC-CLARITY that maintained fluorescence of transgenically expressed proteins. As a proof of concept, we performed in situ hybridization for YFP mRNA on Thy1-YFP transgenic mouse tissue and formulated a hybridization buffer that allowed reduction of hybridization temperature from 45° C. to 37° C., which improved fluorescence in dendrites and axons while maintaining ISH specificity (FIG. 6A, 5A-5C). To provide a generalizable framework for HCR-based RNA detection in EDC-CLARITY, we used these hybridization conditions to design, test, and refine sets of 50mer DNA probes for several representative and broadly-useful target RNAs for molecular phenotyping in nervous system tissue: somatostatin, parvalbumin, neuropeptide Y (NPY), vasoactive intestinal peptide (VIP), tachykinin1, tachykinin2, tyrosine hydroxylase, and Malat1. These targets showed reliable signal in EDC-CLARITY tissue and corresponded to known anatomical distributions in both neural and non-neural tissue (FIG. 6B-6I, FIG. 7A,B).

Figure 8B:
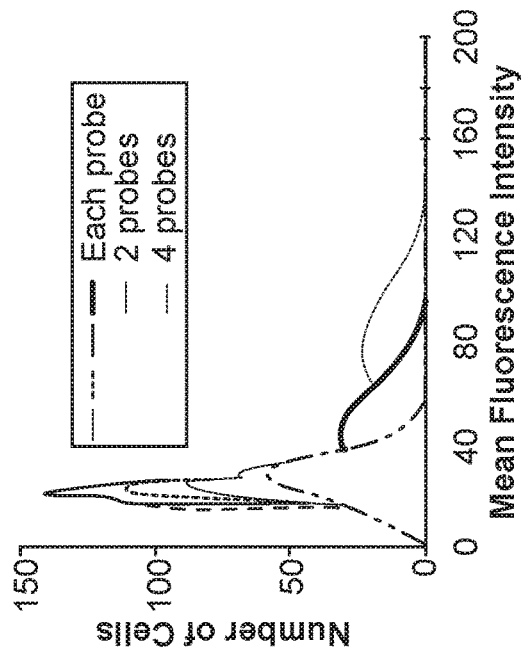
Figure 8C:
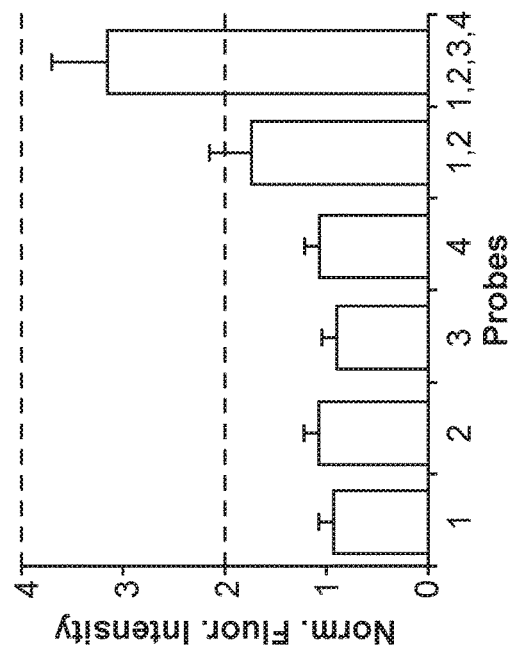
Figure 8A:
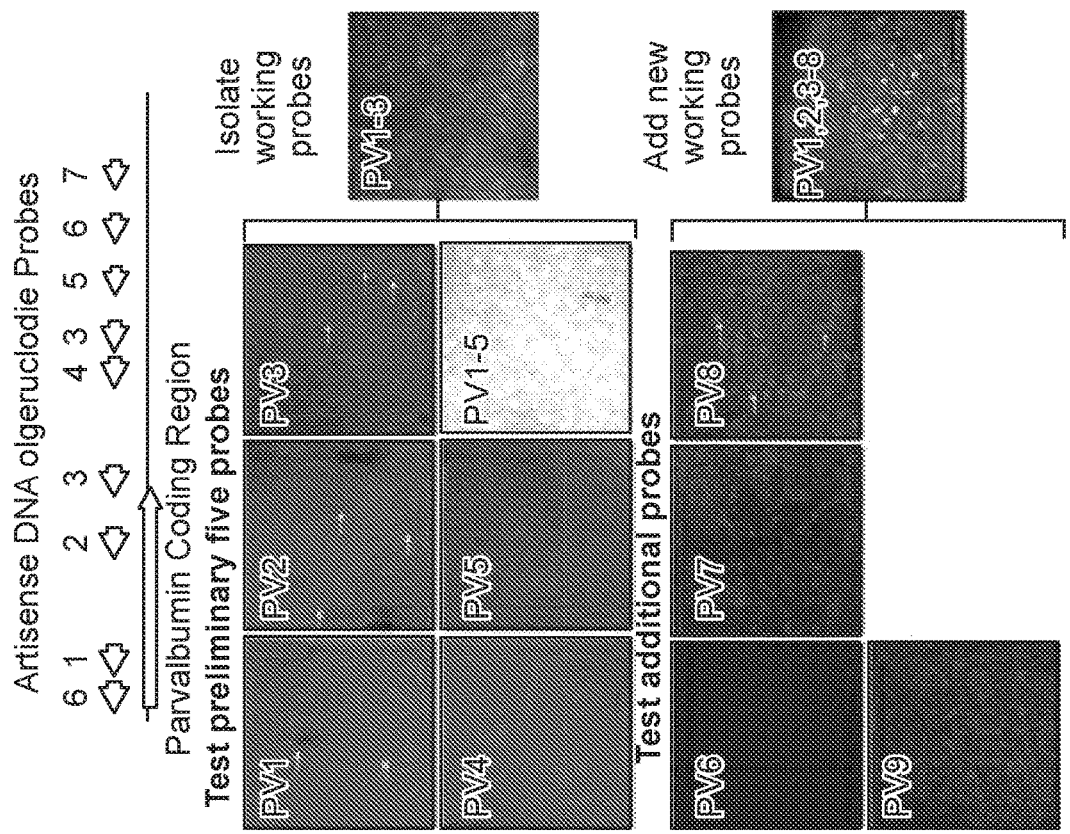

In refining these probe sets, we typically performed initial testing on pools of 5-10 probes; in cases where we observed non-specific staining, we then tested probes individually to identify and discard probes contributing significantly to background, which improved image quality (FIG. 8A). Under these conditions, we estimate that HCR in CLARITY tissue results in ~50 fold amplification per double-initiator-labeled probe (FIG. 8D-8F). In agreement with previous results, increasing the number of initiators, whether by adding initiators to both 5' and 3' ends or by adding more probes, enhances signal substantially. This effect may eventually saturate if limited by slightly sublinear amplification (FIG. 8C), but low copy number transcripts may still benefit from a larger set of probes. In comparing these results to published data from single-cell transcriptomics (Zeisel et al., 2015), we find that our data capture relative differences among gene expression levels across 2 orders of magnitude (FIG. 8G-8H); indeed, with 4 probes per target, this approach allows detection of mRNAs present at as low as ~50 copies/cell (FIG. 8H). Although not as sensitive as RNAseq, probe sets can be expanded as shown below, and the large volumes processed in a single CLARITY experiment enable inclusion of spatial information and sampling from many more cells than would be achieved with RNAseq (particularly important if genes are expressed in sparse subsets within a tissue).

Since low copy-number transcripts may benefit from additional probes, and since it was important to determine if our methodology could be readily adapted to diverse probe design strategies, we tested the feasibility of using a larger set of shorter probes by attaching initiators to the 5' end of probe sets originally designed for single-molecule fluorescent in situ hybridization (smFISH), which typically uses 20mer oligonucleotides (30-50 probes) that tile the mRNA target sequence. As with directly fluorophore-labeled 20mer probes, we expected that with many HCR-labeled 20mers, the on-target signal would accumulate in cells in which many probes bind and amplify (whereas off-target binding would be uniform across the sample); we did not, however, expect that HCR with these probes would provide single-molecule capability. Using this strategy, we were able to detect tyrosine hydroxylase, SERT, and Drd2 mRNA in EDC-CLARITY tissue, demonstrating that the HCR approach is adaptable to other probe types in CLARITY and compatible with larger pools of short probes (FIG. 6J-6L).

Because longer nucleotides are more expensive to synthesize and purify, the strategy of using short probes would reduce overall cost and may enable significantly greater signal amplification. Likely owing to the quick and uniform diffusion of DNA probes and hairpins, we find that tissue blocks up to at least 3 mm thick could be reliably used for intact in situ hybridization (FIG. 6M). Another unique advantage of nucleic acid detection (relative to antibody-based detection) is that once the target sequence is known, it is possible to design probes for the target which are highly specific, permanently renewable, and cost-effective. We therefore anticipate that this methodology for RNA detection in EDC-CLARITY may be versatile for probing a variety of transcriptional products across many tissue-types and species.

Figure 6A:
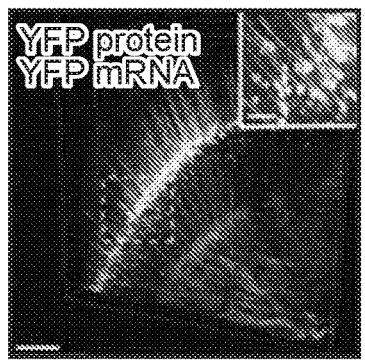
FIG. 6A-6O depict cell-type phenotyping in CLARITY tissue using DNA probes and HCR amplification.
Figure 6B:
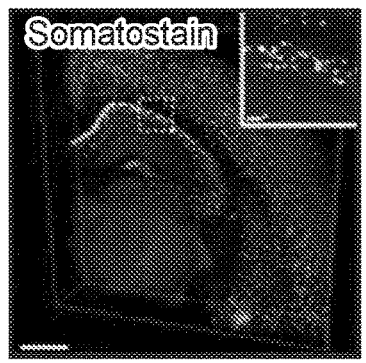
Figure 6C:
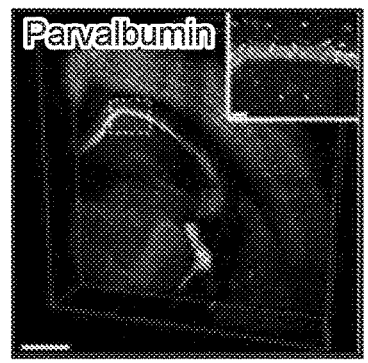
Figure 6D:
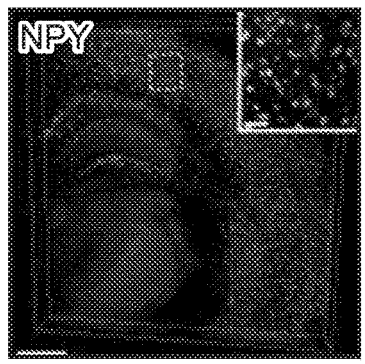
Figure 6E:
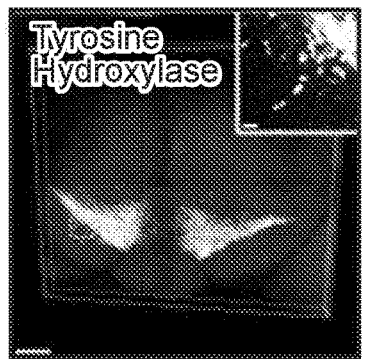
Figure 6F:
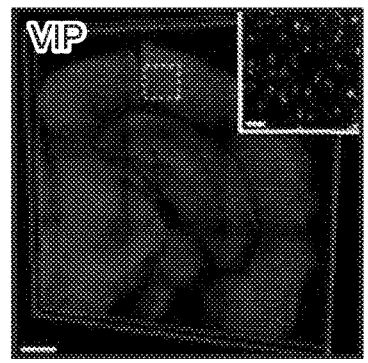
Figure 6G:
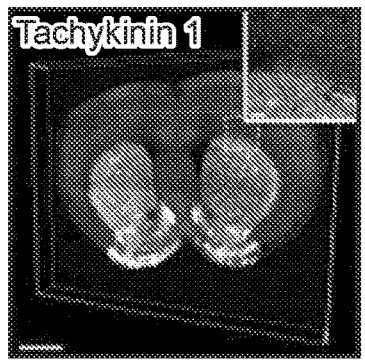
Figure 6H:
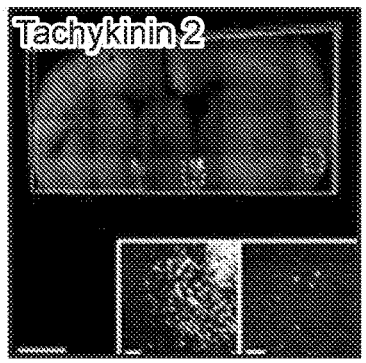
Figure 6I:
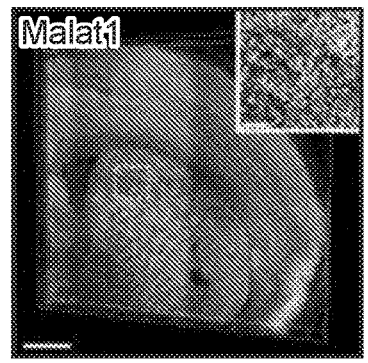
Figure 6J:
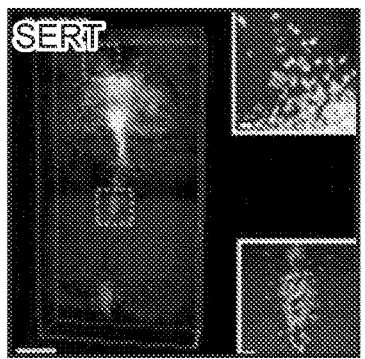
Figure 6K:
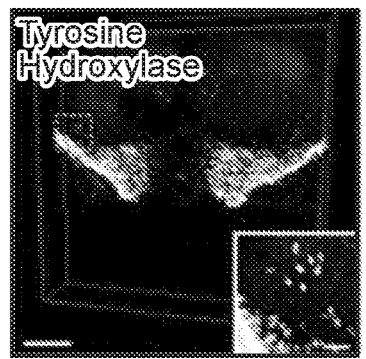
Figure 6L:
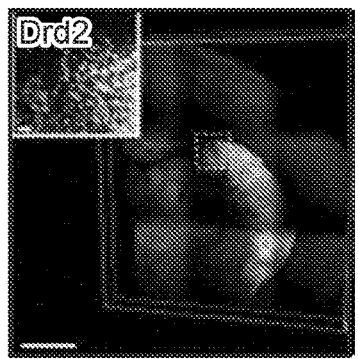
Figure 6M:
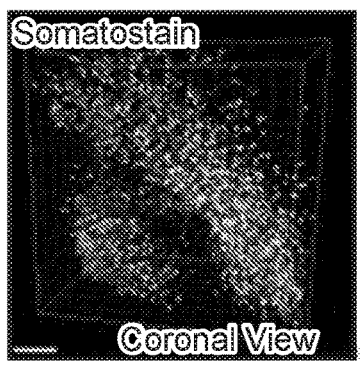
Figure 6N:
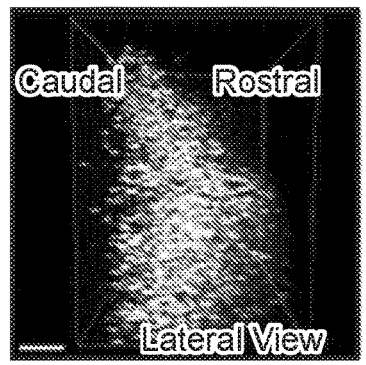
Figure 6O:
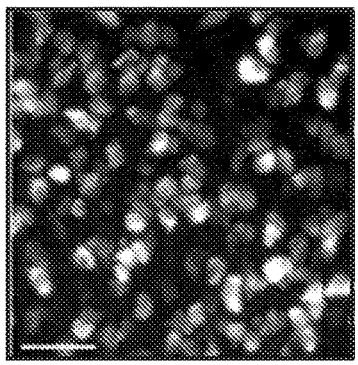

FIG. 6A-6O. Cell-type phenotyping in CLARITY tissue using DNA probes and HCR amplification. (FIG. 6A) 3D rendering of 1-mm-thick coronal section from Thy1-YFP mouse, in situ hybridization for YFP mRNA in red, endogenous YFP fluorescence in green. Scale bar, 200 µm. Inset, 3D rendering of boxed section in cortex. Scale bar, 50 µm. (FIG. 6B-6L) 3D rendering of in situ hybridization performed in 0.5 mm coronal CLARITY sections using 50mer DNA oligonucleotide probes. Scale bars, 500 µm; insets, 50 µm, unless otherwise noted. FIG. 6B) Somatostatin mRNA (4 probes). (FIG. 6C) Parvalbumin mRNA (4 probes). Inset scale bar, 70 µm. (FIG. 6D) Neuropeptide Y mRNA (5 Probes). (FIG. 6E) Tyrosine hydroxylase mRNA (10 probes). (FIG. 6F) Vasoactive Intestinal Peptide (VIP) mRNA (10 probes). (FIG. 6G) Tachykinin1 mRNA (5 probes). Scale bar, 1 mm; inset 100 µm. (FIG. 6H) Tachykinin2 mRNA (4 probes). Scale bar, 1000 µm; inset of BNST and cortex, 50 µm. (FIG. 6I) Malat1 mRNA (4 probes). (FIG. 6J-6L) 3D rendering of in situ hybridization performed in 0.5 mm CLARITY sections using 20mer DNA oligonucleotides. (FIG. 6J) SERT mRNA (47 probes). (FIG. 6K) Tyrosine hydroxylase mRNA (39 probes). (FIG. 6L) Drd2 mRNA (39 probes). Scale bar, 1500 µm, inset; 50 µm. (FIG. 6M) Left, 3D rendering of 2 mm block of mouse cortex, processed with EDC-CLARITY with in situ hybridization for somatostatin using HCR amplification. (Middle) orthogonal view of volume at left, showing signal throughout tissue depth. Scale bars, 200 µm. (Right) magnified view of somatostatin expressing cells in cortex from volume at left. Scale bar, 50 µm. See also FIG. 7A-7, 8A-8H.

Figure 7A:
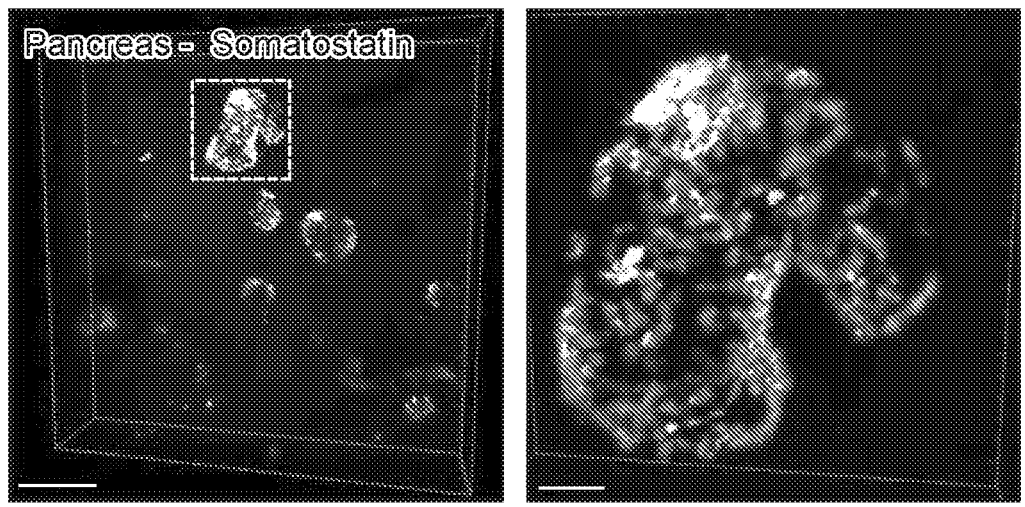
FIG. 7A-7B exemplify application of EDC-CLARITY to non-neural tissue.
Figure 7B:
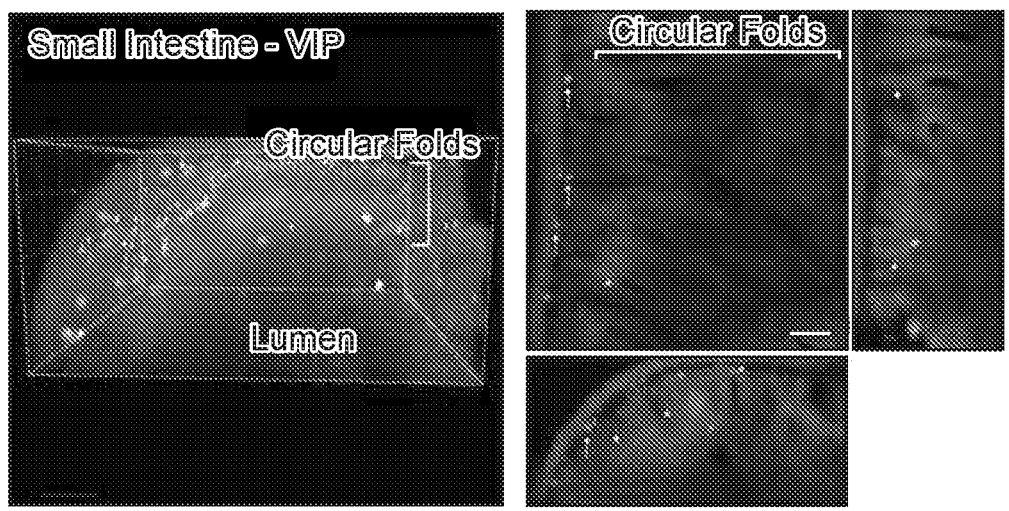

FIG. 7A-7B. Application of EDC-CLARITY to non-neural tissue, related to FIG. 6A-6O. (FIG. 7A) Left, Three-dimensional rendering of a 1 mm thick EDC-CLARITY section of mouse pancreas with in situ hybridization for somatostatin. Scale bar, 300 µm. Right, expanded view of box at right. Delta cells in pancreatic islets are prominently labeled. Scale bar, 50 µm. (FIG. 7B) Left, Three dimensional rendering of an EDC-CLARITY section of mouse small intestine with in situ hybridization for VIP. Scale bar, 100 µm. Right, orthogonal views of tissue at left. Large cells positive for VIP (arrows) are putative peripheral neurons in the submucosal plexus. Smaller puncta in the circular folds correspond well with the distribution of VIP expressing enteroendocrine cells (arrowheads). Scale bar, 200 µm.

FIG. 8A-8H. Characterization of HCR probe design and amplification sensitivity, related to FIG. 6A-6O. (FIG. 8A) In situ hybridization for parvalbumin in 500 µm EDC-CLARITY sections. Confocal images of parvalbumin ISH in cortex. Initial testing of 5 probe cocktail targeting parvalbumin (PV1-5) had high background. Probes were tested individually and probes 1-3 showed specific signal. Omitting probes 4 and 5 decreased background. A second set of 4 probes contains one specific probe (PV8). For parvalbumin, all working probes targeted the coding region of the mRNA. Blue arrows indicated probes tested, red outlines indicate successful probes. All scale bars, 100 µm. (FIG. 8B) Histogram of cell fluorescence intensities for individual somatostatin probes, or combinations of 2 or 4 probes. In situ hybridizations were performed on 500 µm thick CLARITY-EDC sections and amplified with HCR. Cells are segmented, mean fluorescence intensity is plotted, and normal distributions are fit to the data. (n=3 experiments). (FIG. 8C) Average of mean cell intensities per experiment, from data shown in (FIG. 8A), normalized to the average of all individual probes (columns 1-4). Dotted lines represent the linear sum of 2 or 4 probes. (n=3 experiments). Data are means±S.D. (FIG. 8D) Estimation of fold amplification with HCR. 500 μm EDC-CLARITY tissue was hybridized under two conditions. In the first condition, one set of somatostatin probes is labeled with B1 initiators and another set targeting difference sequences is labeled with B5 initiators. Both are amplified with HCR, but with different fluorophores: B1-Alexa647 and B5-Alexa514. In a second condition, one group of probes is labeled with B5 initiators amplified with Alexa514, but the other probes are labeled directly with Alexa647. (FIG. 8E) Somatostatin containing cells were identified using the control Alexa514 channel and the mean fluorescence intensity for both channels was calculated for each cell (average background of each ROI was subtracted from mean intensity). Data for one representative experiment is plotted in (FIG. 8E) as the signal intensity in the Alexa647 channel (for either directly-labeled or HCR-amplified probes) as a function of the control HCR-amplified, Alexa514. Inset highlights low range of y-axis. There is good correlation between the two channels and the relationship is linear, suggesting amplification is proportional to transcript number. (FIG. 8F) Histogram of fluorescence intensities of the Alexa 647 channel for directly labeled or HCR-amplified probes from 4 experiments as in (FIG. 8E). The ratio of the mean HCR value to the mean directly labeled value suggests that there is ~40 fold amplification. (FIG. 8G) Genes with mRNA copy numbers ranging over several orders of magnitude were selected from a published dataset in which single cell RNA-seq data were collected from 1691 cells in mouse cortex (Zeisel et al., 2015). To compare with our dataset, which predominantly uses interneuron cell markers that are highly expressed in one subpopulation but much lower elsewhere, we excluded cells in the RNA-seq data set corresponding to detection of fewer than 5 molecules. Red bars indicate the mean of all cells with >5 transcripts of the gene indicated. (FIG. 8H) In situ hybridizations for 7 different mRNAs were performed in parallel on 500 μm EDC-CLARITY sections of cortex with comparable ROIs taken with identical imaging parameters. To improve cell identification for more weakly expressing mRNA, images were first acquired at the same gain, and then weak signals were imaged again at increased gain. High gain was used to detect cells, but all measurements are from the low gain images, which were the same across all transcripts. Representative cells are shown in the inset and pseudocolored. Below, mean fluorescence intensities are plotted for all cells from three separate experiments, using the same imaging and cell detection parameters for each mRNA. For ease of visualization, a random subset of 1000 cells is shown for Malat1. Red bars indicated the mean intensity for segmented cells; blue bars indicate mean background fluorescence. We are able to detect Npas4 expressing cells, which RNA-seq data from (Zeisel et al., 2015) suggests contain ~50 copies of Npas4 per cell (average molecules detected is ~10, adjusted for a 22% capture rate).

Example 6

Detection of Activity-Dependent Genes and Non-Coding RNAs in Intact Volumes

Many mRNAs are transiently up-regulated by activity, a fact that has been instrumental in identifying cells and circuits recruited during particular behaviors (e.g. Loebrich and Nedivi, 2009). Using such immediate early genes (IEGs), it has been possible to identify neurons involved in complex behaviors (even multiple behaviors separated in time; Guzowski et al., 1999; Reijmers et al., 2007), to visualize behaviorally relevant neurons in transgenic mice, in some cases long after the behavior itself (Barth et al., 2004; Guenthner et al., 2013; Smeyne et al., 1992), and to manipulate these IEG-expressing neurons to modify or recapitulate the observed behavior (Garner et al., 2012; Liu et al., 2012; Ramirez et al., 2013). Yet a major unmet goal is linking form and function: to align these transcriptional activity changes with molecular phenotype and connectivity information in large intact volumes. We therefore next designed HCR probe sets against several canonical activity-regulated transcripts: Arc (Lyford et al., 1995), c-fos (Sheng et al., 1990), and Npas4 (Bloodgood et al., 2014), and tested these probes in a kainic acid seizure model (known to induce robust hippocampal transcription of many activity-regulated genes; Nedivi et al., 1993)). We found that we were able to reliably track changes in expression of all of these activity-regulated genes in EDC-CLARITY. For example, Npas4 is normally expressed in scattered cells in cortex but robustly transcribed in both hippocampal pyramidal cells and interneurons after seizure activity (FIG. 9A). In parallel experiments, increases in c-Fos transcription in hilar neurons and Arc transcription in dentate granule cells were readily detectable (FIG. 9B-9C), as described previously in hippocampal seizure models (Lyford et al., 1995).

Lastly, we assessed detection of small-noncoding RNAs—a major motivation for this entire approach since these are undetectable by antibodies yet also are 1) critical for the modulation of post-transcriptional gene expression; 2) play key roles in human genetic diseases (Esteller, 2011); and 3) represent a wealth of biological information not yet approached by any tissue clearing technique. Indeed, due to small size, microRNAs have fewer amines to react with paraformaldehyde or acrylamide and are easily lost from fixed tissues (Pena et al., 2009; Renwick et al., 2013).

Figure 10A:
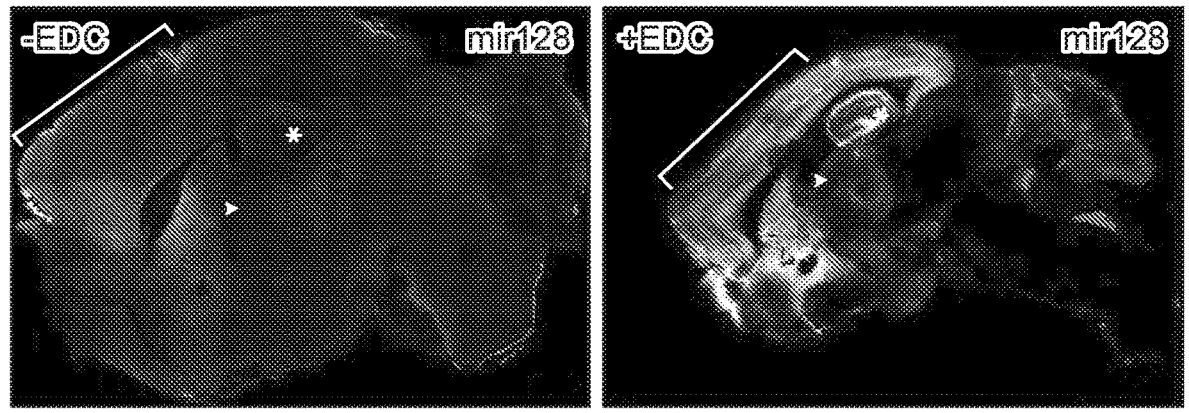
FIG. 10A-10C illustrate detection of microRNAs in CLARITY tissue.
Figure 10B:
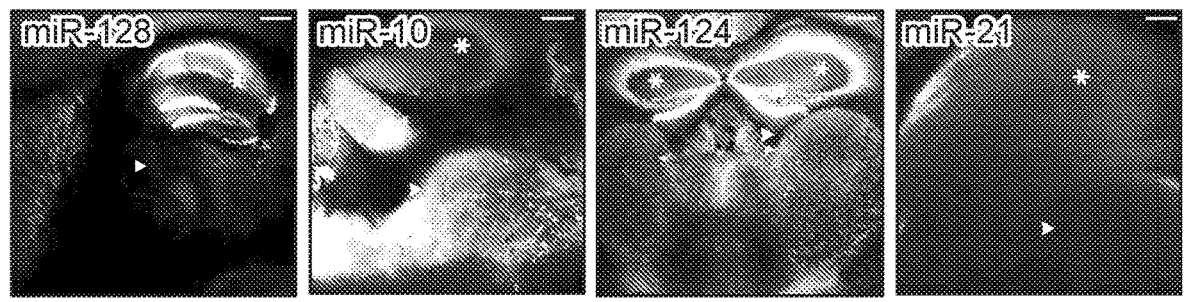
Figure 10C:
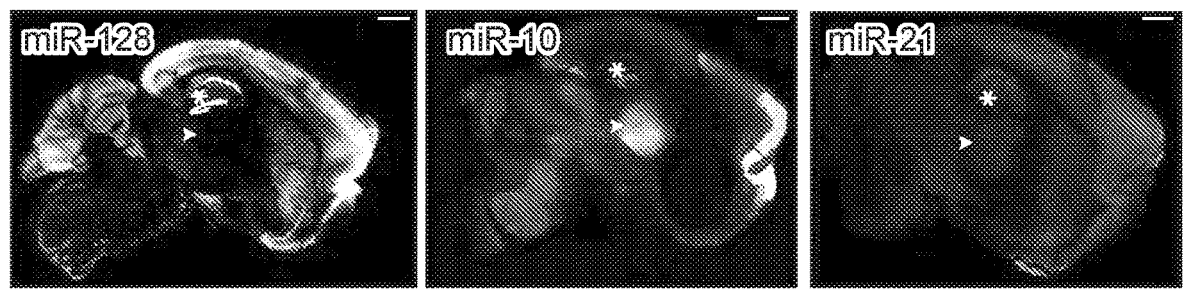

Consistent with this expected challenge, we found that post-treatment with EDC was critical for the retention of miRNAs in EDC-CLARITY (FIG. 10A). Using DIG-labeled locked nucleic acid probes, we targeted several miRNAs with known function in the mammalian brain and in neuropsychiatric disease (miR-10, miR-124, miR-128), as well as a miRNA known to exist only outside the mammalian brain (miR-21) to serve as a negative control (Landgraf et al., 2007). We detected robust expression of these miRNAs in volumes of mouse brain, in a pattern largely limited to areas with anticipated expression (as inferred from miRNA deep sequencing experiments). miR-10 signal (for instance) was almost exclusively recovered in the thalamus, miR-124 was observed to be more ubiquitously present throughout the brain, and miR-128 showed characteristic forebrain and cerebellar enrichment (FIG. 9D, 10B-10C). We observed minimal signal for miR-21 under the same detection and amplification conditions, as expected, highlighting the specificity of the miRNA signals observed.

miR-128 is particularly well-studied in the context of its known disease-relevance for oncogenic suppression (Pang et al., 2009) and predisposition to mood disorders (Zhou et al., 2009) but until now, miR-128 expression has not been visualized volumetrically in the mammalian brain at single cell resolution, which we were readily able to achieve here (FIG. 9D). To further test potential utility of this approach in the study of brain disease, we endeavored to detect miR-128 in human clinical samples to determine if differences in expression might be associated with human glioblastomas (suggested but not directly observed; Ciafrè et al., 2005). We indeed were able to detect miR-128 in human GBM samples processed in EDC-CLARITY hydrogel; moreover, by integrating antibody staining (in this case, GFAP to mark tumor location) with ISH in EDC-CLARITY, we could track the crucial relative relationships of GFAP and miR-128 expression across the tissue volume at cellular resolution (FIG. 9E). Such an approach designed to provide 3D volumetric access to miRNAs in biopsied or post-mortem human brain samples may be valuable in the search for tissue-level disease insights, biomarkers, and therapeutic targets for neurological and psychiatric disease.

FIG. 9A-9B. Detecting activity-induced transcripts and non-coding RNAs in CLARITY volumes. (FIG. 9A-B) 3D rendering of 0.5 mm CLARITY section, HCR in situ hybridization in control saline injected (left) and kainic acid injected (right) animals. Kainic acid, 12 mg/kg, i.p., 2 hours prior to perfusion. (FIG. 9A) Npas4 mRNA (4 probes). Scale bar, 200 µm. Right, magnified view of indicated boxes. Scale bar, 100 µm. (FIG. 9B) Arc mRNA (5 probes). Right, magnified view of indicated boxes. Scale bar, 50 µm. (C) c-fos mRNA (45 probes). Scale bars 500 µm; Right, magnified view of dentate gyrus as indicated by dotted box. Scale bar, 100 µm. (D) Left, projection image of 1 mm mouse brain sagittal section, cleared, and hybridized with DIG-labeled LNA probes for mature miR-128 sequence. Scale bar, 500 µm. Middle, right 10× zoom of hippocampal and striatal volumes respectively. Scale bar, 150 µm. (E) Left, projection images of human brain control (left) and tumor (GBM) (middle) samples, cleared and in situ hybridized for miR-128 (green). Scale: 50 µm (Right). Volume reconstruction of human GBM tumor biopsy sample (200 µm thick; scale: 50 µm) also stained with antibody to GFAP (red). miR-128 and GFAP have orthogonal signal gradients within the tumor preparation. See also FIG. 10A-10C.

FIG. 10A-10C. Detection of microRNAs in CLARITY tissue, related to FIG. 9A-9B. (FIG. 10A) Projection images of 5× confocally acquired and tiled 1 mm mouse brain sagittal sections, cleared, and in situ hybridized with DIG-labeled LNA probes complementary to the mature miR-128 sequence without (left) and with (right) EDC fixation. Brain regions indicated as follows: forebrain (brackets), hippocampus (asterisk), thalamus (arrowhead). Scale: 700 µm (left) and 800 µm (right). (FIG. 10B) Projection images of 10× confocally acquired 1 mm mouse brain coronal sections, cleared and in situ hybridized with DIG-labeled LNA probes complementary to the mature miR-128, miR-10b, miR-124, and miR-21 sequences. miR-128 is preferentially expressed in hippocampus (asterisk), miR-10 in thalamus (arrowhead), and miR-124 in both. There is minimal expression of miR-21 in either structure (consistent with sequencing data suggesting lack of miR-21 expression in adult brain tissue). Scale: 100/100/100/50 µm. (FIG. 10C) Projection images of 5× confocally acquired and tiled 1 mm mouse brain sagittal section, cleared and in situ hybridized with DIG-labeled LNA probes complementary to the mature miR-128, miR-10, and miR-21 sequences. Scale: 150 µm. Brain regions indicated as follows: hippocampus (asterisk), thalamus (arrowhead).

Example 7

Multiplexed Molecular Phenotyping

Figure 12B:
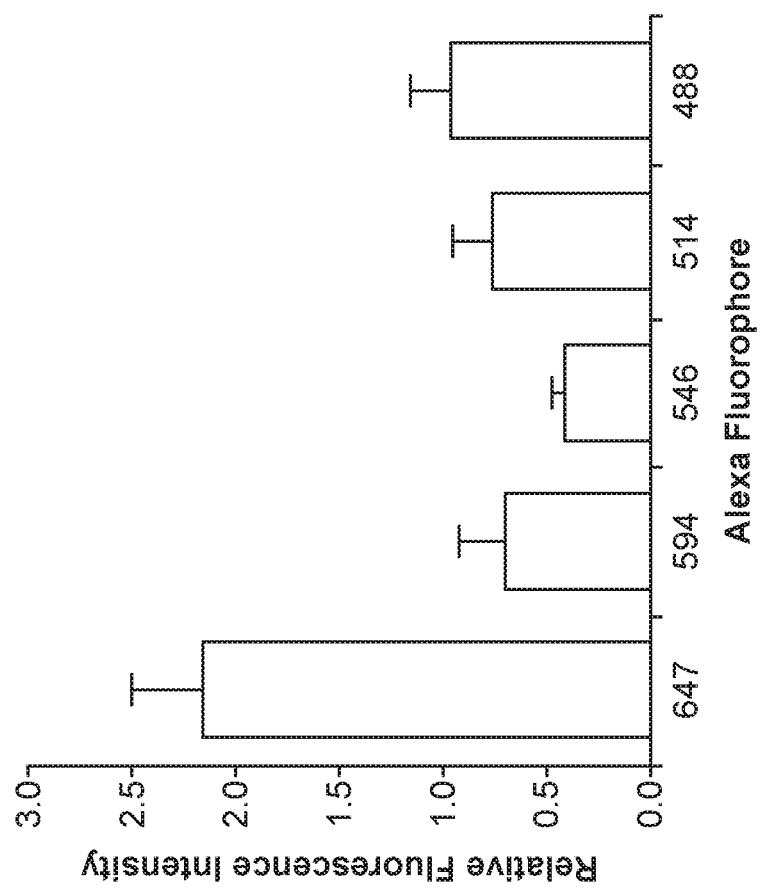
FIG. 12A-12B show characterization of orthogonal hairpins.
Figure 12A:
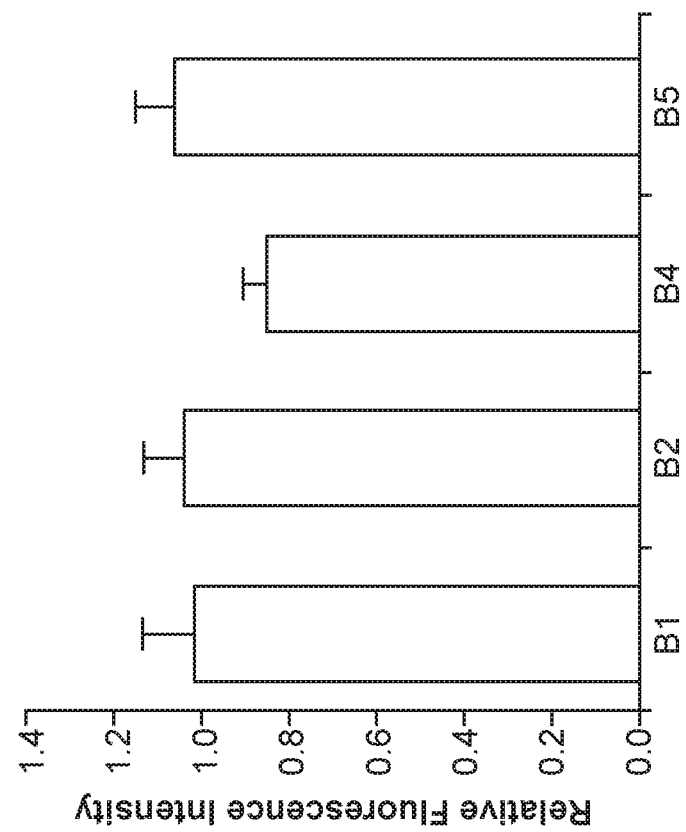

Finally, we sought to develop methods for multiplexed detection of RNA in EDC-CLARITY to address the critical and rapidly-growing need for multiple overlaid markers of cell identity or activity in the native anatomical context. Using multiplexed hybridization and amplification with orthogonal hairpin sets (Choi et al, 2014), we were able to simultaneously label multiple mRNAs in EDC-CLARITY. Of note, although orthogonal hairpins were equivalent in amplification, individual fluorophores varied in fluorescence signal, as may be expected by differences in tissue autofluorescence, fluorophore efficiency, and light transmittance at different wavelengths (FIG. 12A, 12B). Nevertheless, somatostatin, parvalbumin, and tyrosine hydroxylase could be simultaneously hybridized and amplified with sets of orthogonal hairpins carrying Alexa514, Alexa647 and Alexa546 fluorophores, respectively (FIG. 11A). We were also able to combine in situ hybridization for cell-type markers with in situ hybridization for activity markers (FIG. 11B). Taken together, these data demonstrate key steps toward integrated investigation of cellular structure and typology, microRNA expression, and activity-regulated gene transcription within intact tissue volumes.

FIG. 11A-11B. Multiplexed detection of mRNAs in CLARITY. (FIG. 11A) Left, multiplexed in situ hybridization of 0.5 mm coronal CLARITY section treated with kainic acid, using somatostatin (red), parvalbumin (blue) and tyrosine hydroxylase (green) probe sets. Scale bar, 500 µm. Middle, inset of caudal hippocampus showing parvalbumin and somatostatin interneurons in CA1 region. Scale bar, 50 µm. Right, parvalbumin and tyrosine hydroxylase positive cells in midbrain. Scale bar, 100 µm. (FIG. 11B) 3D rendering of 1 mm CLARITY block, HCR in situ hybridization for somatostatin (red) and Arc mRNA (green) in control saline injected (left) and kainic acid injected (right) animals. Right, magnified view of indicated boxes. Scale bar, 100 µm. See also FIG. 12A-12B.

FIG. 12A-12B. Characterization of orthogonal hairpins, related to FIG. 11A-11B. (FIG. 12A) Four orthogonal hairpins sets have equivalent amplification in CLARITY-EDC tissue. In situ hybridizations for somatostatin were performed using the same probe sequences and fluorophore (Alexa647), with 4 different hairpin sets (B1, B2, B4, and B5, as described in (Choi et al., 2014)), and normalized to the mean intensity of all conditions (n=3) Data are means±S.D. (FIG. 12B) Relative fluorescent intensities of different Alexa fluorophores. In situ hybridization for somatostatin was performed on 500 µm CLARITY tissue using B1 hairpins conjugated to the dyes indicated. Fluorescence intensity of somatostatin cells was calculated, background auto fluorescence was subtracted for each channel, and then normalized to the mean intensity of all conditions (n=3) Data are means±S.D.

Although preferred embodiments of the subject invention have been described in some detail, it is understood that obvious variations can be made without departing from the spirit and the scope of the invention as defined herein.

REFERENCES

Barth, A. L., Gerkin, R. C., and Dean, K. L. (2004). Alteration of neuronal firing properties after in vivo experience in a FosGFP transgenic mouse. J. Neurosci. 24, 6466-6475.

Battich, N., Stoeger, T., and Pelkmans, L. (2013). Image-based transcriptomics in thousands of single human cells at single-molecule resolution. Nat Meth 1-10.

Bloodgood, B. L., Sharma, N., Browne, H. A., Trepman, A. Z., and Greenberg, M. E. (2014). The activity-dependent transcription factor NPAS4 regulates domain-specific inhibition. Nature 503, 121-125.

Choi, H. M. T., Beck, V. A., and Pierce, N. A. (2014). Next-Generation in Situ Hybridization Chain Reaction: Higher Gain, Lower Cost, Greater Durability. ACS Nano 8, 4284-4294.

Choi, H. M. T., Chang, J. Y., Le A Trinh, Padilla, J. E., Fraser, S. E., and Pierce, N. A. (2010). Programmable in situ amplification for multiplexed imaging of mRNA expression. Nat. Biotechnol. 28, 1208-1212.

Chung, K., Wallace, J., Kim, S.-Y., Kalyanasundaram, S., Andalman, A. S., Davidson, T. J., Mirzabekov, J. J., Zalocusky, K. A., Mattis, J., Denisin, A. K., et al. (2013). Structural and molecular interrogation of intact biological systems. Nature 497, 332-337.

Ciafrè, S. A., Galardi, S., Mangiola, A., Ferracin, M., Liu, C.-G., Sabatino, G., Negrini, M., Maira, G., Croce, C. M., and Farace, M. G. (2005). Extensive modulation of a set of microRNAs in primary glioblastoma. Biochem. Biophys. Res. Commun. 334, 1351-1358.

Denk, W., and Horstmann, H. (2004). Serial block-face scanning electron microscopy to reconstruct three-dimensional tissue nanostructure. PLoS Biol 2, e329.

Dodt, H.-U., Leischner, U., Schierloh, A., Jährling, N., Mauch, C. P., Deininger, K., Deussing, J. M., Eder, M., Zieglgänsberger, W., and Becker, K. (2007). Ultramicroscopy: three-dimensional visualization of neuronal networks in the whole mouse brain. Nat Meth 4, 331-336.

Ertürk, A., Becker, K., Jährling, N., Mauch, C. P., Hojer, C. D., Egen, J. G., Hellal, F., Bradke, F., Sheng, M., and Dodt, H.-U. (2012). Three-dimensional imaging of solvent-cleared organs using 3DISCO. Nature Protocols 7, 1983-1995.

Esteller, M. (2011). Non-coding RNAs in human disease. Nat Rev Genet 12, 861-874.

Garner, A. R., Rowland, D. C., Hwang, S. Y., Baumgaertel, K., Roth, B. L., Kentros, C., and Mayford, M. (2012). Generation of a synthetic memory trace. Science 335, 1513-1516.

Guenthner, C. J., Miyamichi, K., Yang, H. H., Heller, H. C., and Luo, L. (2013). Permanent genetic access to transiently active neurons via TRAP: targeted recombination in active populations. Neuron 78, 773-784.

Guzowski, J. F., McNaughton, B. L., Barnes, C. A., and Worley, P. F. (1999). Environment-specific expression of the immediate-early gene Arc in hippocampal neuronal ensembles. Nat Neurosci 2, 1120-1124.

Hama, H., Hioki, H., Namiki, K., Hoshida, T., Kurokawa, H., Ishidate, F., Kaneko, T., Akagi, T., Saito, T., Saido, T., et al. (2015). ScaleS: an optical clearing palette for biological imaging. Nat Neurosci 1-14.

Hama, H., Kurokawa, H., Kawano, H., Ando, R., Shimogori, T., Noda, H., Fukami, K., Sakaue-Sawano, A., and Miyawaki, A. (2011). Scale: a chemical approach for fluorescence imaging and reconstruction of transparent mouse brain. Nat Neurosci 14, 1481-1488.

Ke, R., Mignardi, M., Pacureanu, A., Svedlund, J., Boding, J., Wählby, C., and Nilsson, M. (2013). In situ sequencing for RNA analysis in preserved tissue and cells. Nat Meth 10, 857-860.

Kuwajima, T., Sitko, A. A., Bhansali, P., Jurgens, C., Guido, W., and Mason, C.
(2013). ClearT: a detergent- and solvent-free clearing method for neuronal and non-neuronal tissue. Development 140, 1364-1368.

Landgraf, P., Rusu, M., Sheridan, R., Sewer, A., Iovino, N., Aravin, A., Pfeffer, S., Rice, A., Kamphorst, A. O., Landthaler, M., et al. (2007). A mammalian microRNA expression atlas based on small RNA library sequencing. Cell 129, 1401-1414.

Lee, J. H., Daugharthy, E. R., Scheiman, J., Kalhor, R., Yang, J. L, Ferrante, T. C., Terry, R., Jeanty, S. S. F., Li, C., Amamoto, R., et al. (2014). Highly Multiplexed Subcellular RNA Sequencing in Situ. Science 343, 1360-1363.

Li, J., Czajkowsky, D. M., Li, X., and Shao, Z. (2015). Fast immuno-labeling by electrophoretically driven infiltration for intact tissue imaging. Sci Rep 5, 10640.

Lin, D., Boyle, M. P., Dollar, P., Lee, H., Lein, E. S., Perona, P., and Anderson, D. J. (2011). Functional identification of an aggression locus in the mouse hypothalamus. Nature 470, 221-226.

Liu, X., Ramirez, S., Pang, P. T., Puryear, C. B., Govindarajan, A., Deisseroth, K., and Tonegawa, S. (2012). Optogenetic stimulation of a hippocampal engram activates fear memory recall. Nature 484, 381-385.

Loebrich, S., and Nedivi, E. (2009). The Function of Activity-Regulated Genes in the Nervous System. Physiological Reviews 89, 1079-1103.

Lyford, G. L., Yamagata, K., Kaufmann, W. E., Barnes, C. A., Sanders, L. K., Copeland, N. G., Gilbert, D. J., Jenkins, N. A., Lanahan, A. A., and Worley, P. F. (1995). Arc, a growth factor and activity-regulated gene, encodes a novel cytoskeleton-associated protein that is enriched in neuronal dendrites. Neuron 14, 433-445.

Masuda, N., Ohnishi, T., Kawamoto, S., Monden, M., and Okubo, K. (1999). Analysis of chemical modification of RNA from formalin-fixed samples and optimization of molecular biology applications for such samples. Nucleic Acids Research 27, 4436-4443.

Mattson, G., Conklin, E., Desai, S., Nielander, G., Savage, M. D., and Morgensen, S. (1993). A practical approach to crosslinking. Mol. Biol. Rep. 17, 167-183.

Micheva, K. D., and Smith, S. J. (2007). Array tomography: a new tool for imaging the molecular architecture and ultrastructure of neural circuits. Neuron 55, 25-36.

Nedivi, E., Hevroni, D., Naot, D., Israeli, D., and Citri, Y. (1993). Numerous candidate plasticity-related genes revealed by differential cDNA cloning. Nature 363, 718-722.

Oh, S. W., Harris, J. A., Ng, L., Winslow, B., Cain, N., Mihalas, S., Wang, Q., Lau, C., Kuan, L., Henry, A. M., et al. (2014). A mesoscale connectome of the mouse brain. Nature 508, 207-214.

Pang, J. C.-S., Kwok, W. K., Chen, Z., and Ng, H.-K. (2009). Oncogenic role of microRNAs in brain tumors. Acta Neuropathol. 117, 599-611.

Pena, J. T. G., Sohn-Lee, C., Rouhanifard, S. H., Ludwig, J., Hafner, M., Mihailovic, A., Lim, C., Holoch, D., Berninger, P., Zavolan, M., et al. (2009). miRNA in situ hybridization in formaldehyde and EDC-fixed tissues. Nat Meth 6, 139-141.

Ramirez, S., Liu, X., Lin, P.-A., Suh, J., Pignatelli, M., Redondo, R. L, Ryan, T. J., and Tonegawa, S. (2013). Creating a false memory in the hippocampus. Science 341, 387-391.

Reijmers, L. G., Perkins, B. L., Matsuo, N., and Mayford, M. (2007). Localization of a stable neural correlate of associative memory. Science 317, 1230-1233.

Renier, N., Wu, Z., Simon, D. J., Yang, J., Ariel, P., and Tessier-Lavigne, M. (2014). iDISCO: a simple, rapid method to immunolabel large tissue samples for volume imaging. Cell 159, 896-910.

Renwick, N., Cekan, P., Masry, P. A., McGeary, S. E., Miller, J. B., Hafner, M., Li, Z., Mihailovic, A., Morozov, P., Brown, M., et al. (2013). Multicolor microRNA FISH effectively differentiates tumor types. J. Clin. Invest. 123, 2694-2702.

Resch-Genger, U., Grabolle, M., Cavaliere-Jaricot, S., Nitschke, R., and Nann, T. (2008). Quantum dots versus organic dyes as fluorescent labels. Nat Meth 5, 763-775.

Richardson, D. S., and Lichtman, J. W. (2015). Clarifying Tissue Clearing. Cell 162, 246-257.

Shen, G., Anand, M. F. G., and Levicky, R. (2004). X-ray photoelectron spectroscopy and infrared spectroscopy study of maleimide-activated supports for immobilization of oligodeoxyribonucleotides. Nucleic Acids Research 32, 5973-5980.

Sheng, M., McFadden, G., and Greenberg, M. E. (1990). Membrane depolarization and calcium induce c-fos transcription via phosphorylation of transcription factor CREB. Neuron 4, 571-582.

Simard, C., Lemieux, R., and Côté, S. (2001). Urea substitutes toxic formamide as destabilizing agent in nucleic acid hybridizations with RNA probes. Electrophoresis 22, 2679-2683.

Smeyne, R. J., Schilling, K., Robertson, L., Luk, D., Oberdick, J., Curran, T., and Morgan, J. I. (1992). fos-lacZ transgenic mice: mapping sites of gene induction in the central nervous system. Neuron 8, 13-23.

Song, W., Zhu, K., Cao, Z., Lau, C., and Lu, J. (2012). Hybridization chain reaction-based aptameric system for the highly selective and sensitive detection of protein. Analyst 137, 1396-1396.

Spalteholz, W. (1911). Uber das Durchsichtigmachen von menschlichen und tierischen Präparaten und seine theoretischen Bedingungen (Leipzig: S. Hirzel).

Srinivasan, M., Sedmak, D., and Jewell, S. (2002). Effect of fixatives and tissue processing on the content and integrity of nucleic acids. The American Journal of Pathology 161, 1961-1971.

Staudt, T., Lang, M. C., Medda, R., Engelhardt, J., and Hell, S. W. (2007). 2,2'-thiodiethanol: a new water soluble mounting medium for high resolution optical microscopy. Microsc. Res. Tech. 70, 1-9.

Susaki, E. A., Tainaka, K., Perrin, D., Kishino, F., Tawara, T., Watanabe, T. M., Yokoyama, C., Onoe, H., Eguchi, M., Yamaguchi, S., et al. (2014). Whole-brain imaging with single-cell resolution using chemical cocktails and computational analysis. Cell 157, 726-739.

Tainaka, K., Kubota, S. I., Suyama, T. Q., Susaki, E. A., Perrin, D., Ukai-Tadenuma, M., Ukai, H., and Ueda, H. R. (2014). Whole-body imaging with single-cell resolution by tissue decolorization. Cell 159, 911-924.

Tomer, R., Ye, L., Hsueh, B., and Deisseroth, K. (2014). Advanced CLARITY for rapid and high-resolution imaging of intact tissues. Nature Protocols 9, 1682-1697.

Tymianski, M., Bernstein, G. M., Abdel-Hamid, K. M., Sattler, R., Velumian, A., Carlen, P. L., Razavi, H., and Jones, O. T. (1997). A novel use for a carbodiimide compound for the fixation of fluorescent and non-fluorescent calcium indicators in situ following physiological experiments. Cell Calcium 21, 175-183.

Wanner, A. A., Kirschmann, M. A., and Genoud, C. (2015). Challenges of microtome-based serial block-face scanning electron microscopy in neuroscience. J Microsc 259, 137-142.

Wernersson, R., Juncker, A. S., and Nielsen, H. B. (2007). Probe selection for DNA microarrays using OligoWiz. Nature Protocols 2, 2677-2691.

Wilkinson, D. G. (1999). In Situ Hybridization: A Practical Approach. (Oxford University Press).

Yang, B., Treweek, J. B., Kulkarni, R. P., Deverman, B. E., Chen, C.-K., Lubeck, E., Shah, S., Cai, L, and Gradinaru, V. (2014). Single-cell phenotyping within transparent intact tissue through whole-body clearing. Cell 158, 945-958.

Zeisel, A., Munoz-Manchado, A. B., Codeluppi, S., Lonnerberg, P., La Manno, G., Jureus, A., Marques, S., Munguba, H., He, L., Betsholtz, C., et al. (2015). Cell types in the mouse cortex and hippocampus revealed by single-cell RNA-seq. Science 347, 1138-1142.

Zheng, H., and Rinaman, L. (2015). Simplified CLARITY for visualizing immunofluorescence labeling in the developing rat brain. Brain Struct Funct 1-9.

Zhou, R., Yuan, P., Wang, Y., Hunsberger, J. G., Elkahloun, A., Wei, Y., Damschroder-Williams, P., Du, J., Chen, G., and Manji, H. K. (2009). Evidence for selective microRNAs and their effectors as common long-term targets for the actions of mood stabilizers. Neuropsychopharmacology 34, 1395-1405.

What is claimed is:

1. A method of preparing a biological specimen for microscopic analysis of a target RNA analyte, the method comprising:
- fixing the specimen with a plurality of hydrogel subunits;
- polymerizing the hydrogel subunits to form a hydrogel-embedded specimen;
- fixing RNA in the specimen using carbodiimide mediated crosslinking;
- clearing the hydrogel-embedded specimen wherein the RNA is substantially retained in the specimen; and
- contacting the specimen with a nucleic acid probe for a target RNA analyte.

2. The method of claim 1, wherein the carbodiimide comprises 1-Ethyl-3-3-dimethyl-aminopropyl carbodiimide (EDC).

3. The method of claim 1, wherein the nucleic acid probe undergoes a Hybridization Chain Reaction (HCR).

4. The method of claim 1, wherein the nucleic acid probe is a DNA probe.

5. The method of claim 1, wherein the nucleic acid probe is a RNA probe.

6. The method of claim 1, wherein the specimen is stored for at least one week prior to the contacting.

7. The method of claim 1, wherein the specimen is stored at 4° C. for a period of one week to a year prior to the contacting.

8. The method of claim 1, wherein the specimen is stored at 4° C. for a period of one week to six months prior to the contacting.

9. The method of claim 1, wherein the contacting comprises contacting the specimen with a plurality of nucleic acid probes for a plurality of target RNA analytes.

10. The method of claim 1, wherein the clearing comprises substantially removing a plurality of cellular components from the specimen.

11. The method of claim 1, wherein the clearing comprises substantially removing lipids from the specimen.

12. The method of claim 1, wherein the clearing comprises electrophoresing the specimen.

13. The method of claim 12, wherein the electrophoresing comprises using a buffer solution comprising an ionic surfactant.

14. The method of claim 1, wherein the specimen is a biopsy specimen or autopsy specimen.

15. The method of claim 1, wherein the specimen is from a human.

16. The method of claim 1, wherein the method further comprises imaging the specimen using confocal microscopy, two-photon microscopy, light-field microscopy, tissue expansion microscopy, and/or CLARITY™-optimized light sheet microscopy (COLM).

17. The method of claim 1, further comprising amplifying the RNA prior to the contacting.

18. The method of claim 17, wherein the amplifying comprises hybridization chain reaction (HCR).

19. The method of claim 17, wherein the amplifying is a multiplexed amplification identifying multiple RNA analytes.

* * * * *